United States Patent
Faustman

(10) Patent No.: US 10,765,700 B2
(45) Date of Patent: *Sep. 8, 2020

(54) METHODS FOR EXPANSION OR DEPLETION OF T-REGULATORY CELLS

(71) Applicant: The General Hospital Corporation, Boston, MA (US)

(72) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,713

(22) Filed: Nov. 20, 2017

(65) Prior Publication Data

US 2018/0161370 A1 Jun. 14, 2018

Related U.S. Application Data

(63) Continuation of application No. 14/764,325, filed as application No. PCT/US2014/015101 on Feb. 6, 2014, now Pat. No. 9,821,010.

(60) Provisional application No. 61/763,217, filed on Feb. 11, 2013, provisional application No. 61/762,136, filed on Feb. 7, 2013.

(51) Int. Cl.
| | | |
|---|---|---|
| *A61K 39/00* | (2006.01) | |
| *C12N 5/0783* | (2010.01) | |
| *C07K 16/28* | (2006.01) | |
| *A61K 35/17* | (2015.01) | |

(52) U.S. Cl.
CPC .............. *A61K 35/17* (2013.01); *A61K 39/00* (2013.01); *C07K 16/2878* (2013.01); *C12N 5/0637* (2013.01); *A61K 2039/515* (2013.01); *C07K 2317/34* (2013.01); *C07K 2317/73* (2013.01); *C07K 2317/74* (2013.01); *C07K 2317/75* (2013.01); *C07K 2317/76* (2013.01); *C07K 2317/92* (2013.01); *C12N 2501/04* (2013.01); *C12N 2501/2302* (2013.01); *C12N 2501/25* (2013.01); *C12N 2501/51* (2013.01); *C12N 2501/515* (2013.01); *C12N 2501/60* (2013.01)

(58) Field of Classification Search
CPC ................. A61K 35/17; C07K 16/2878; C07K 2317/34; C12N 5/0637
See application file for complete search history.

(56) References Cited

U.S. PATENT DOCUMENTS

| | | | |
|---|---|---|---|
| 4,309,418 A | 1/1982 | Green | |
| 4,457,916 A | 7/1984 | Hayashi et al. | |
| 4,495,282 A | 1/1985 | Ohnishi et al. | |
| 4,677,063 A | 6/1987 | Mark et al. | |
| 4,677,064 A | 6/1987 | Mark et al. | |
| 4,681,760 A | 7/1987 | Fathman | |
| 4,791,101 A | 12/1988 | Adolf | |
| 4,816,567 A | 3/1989 | Cabilly et al. | |
| 4,879,226 A | 11/1989 | Wallace et al. | |
| 4,963,354 A | 10/1990 | Shepard et al. | |
| 4,985,241 A | 1/1991 | Zimmerman et al. | |
| 5,002,876 A | 3/1991 | Sreekrishna et al. | |
| 5,059,530 A | 10/1991 | Oshima et al. | |
| 5,139,481 A | 8/1992 | Faustman et al. | |
| 5,215,743 A | 6/1993 | Singh et al. | |
| 5,283,058 A | 2/1994 | Faustman | |
| 5,288,852 A | 2/1994 | Yamada et al. | |
| 5,370,870 A | 12/1994 | Wong | |
| 5,487,984 A | 1/1996 | Allet et al. | |
| 5,538,854 A | 7/1996 | Faustman | |
| 5,560,908 A | 10/1996 | Satoh et al. | |
| 5,593,698 A | 1/1997 | Weiner et al. | |
| 5,783,216 A | 7/1998 | Faustman | |
| 5,821,337 A | 10/1998 | Carter et al. | |
| 5,843,425 A | 12/1998 | Sachs et al. | |
| 5,843,452 A | 12/1998 | Wiedmann et al. | |
| 5,874,306 A | 2/1999 | Beattie et al. | |
| 5,919,452 A | 7/1999 | Le et al. | |
| 5,939,532 A | 8/1999 | Nakamura et al. | |
| 6,046,031 A | 4/2000 | Ni et al. | |
| 6,056,952 A | 5/2000 | Rosenberg | |
| 6,159,461 A | 12/2000 | Besmer et al. | |
| 6,165,737 A | 12/2000 | Wang et al. | |
| 6,177,076 B1 | 1/2001 | Lattime et al. | |
| 6,284,879 B1 | 9/2001 | Faustman | |
| 6,414,218 B1 | 7/2002 | Faustman et al. | |
| 6,420,139 B1 | 7/2002 | Classen | |
| 6,491,908 B1 | 12/2002 | Rosenberg | |

(Continued)

FOREIGN PATENT DOCUMENTS

| | | |
|---|---|---|
| EP | 0612529 A2 | 8/1994 |
| EP | 2295588 A1 | 3/2011 |

(Continued)

OTHER PUBLICATIONS

Al-Awqati et al., "Stem cells in the kidney," Kidney Int. 61(2):387-95 (2002).

Aldrich et al., "Positive selection of self- and alloreactive CD8+ T cells in Tap-1 mutant mice," Proc Natl Acad Sci USA. 91(14):6525-8 (1994).

Alison et al., "Hepatocytes from non-hepatic adult stem cells," Nature. 406(6793):257 (2000).

(Continued)

*Primary Examiner* — Daniel C Gamett
(74) *Attorney, Agent, or Firm* — Clark & Elbing LLP

(57) ABSTRACT

The invention features methods of producing compositions enriched in Tregs and methods for treating immunological disorders using these compositions. The invention also features methods for producing compositions enriched in lymphocytes and depleted of Tregs and the use of these compositions in the treatment of proliferative disorders.

10 Claims, 14 Drawing Sheets

Specification includes a Sequence Listing.

(56) References Cited

U.S. PATENT DOCUMENTS

| | | | |
|---|---|---|---|
| 6,599,710 B1 | 7/2003 | Faustman | |
| 6,617,171 B2 | 9/2003 | Faustman et al. | |
| 6,660,487 B2 | 12/2003 | Faustman | |
| 6,709,833 B2 * | 3/2004 | Fukui | C07K 16/18 435/326 |
| 6,773,705 B1 | 8/2004 | Faustman et al. | |
| 6,844,011 B1 | 1/2005 | Faustman | |
| 6,866,843 B2 | 3/2005 | Habener et al. | |
| 6,923,959 B2 | 8/2005 | Habener et al. | |
| 6,984,380 B1 | 1/2006 | Faustman | |
| 7,015,037 B1 | 3/2006 | Furcht et al. | |
| 7,438,902 B2 | 10/2008 | Habener et al. | |
| 7,485,293 B2 | 2/2009 | Faustman | |
| 7,510,877 B2 | 3/2009 | Yilmaz et al. | |
| 7,537,756 B2 | 5/2009 | Habener et al. | |
| 7,582,313 B2 | 9/2009 | Faustman | |
| 7,628,988 B2 | 12/2009 | Faustman | |
| 8,173,129 B2 | 5/2012 | Faustman | |
| 8,314,213 B2 * | 11/2012 | Bernett | C07K 16/00 530/388.2 |
| 9,676,862 B2 | 6/2017 | Ellmark et al. | |
| 9,821,010 B2 | 11/2017 | Faustman | |
| 2002/0106689 A1 | 8/2002 | Faustman et al. | |
| 2002/0123472 A1 | 9/2002 | Faustman | |
| 2002/0187548 A1 | 12/2002 | Keller et al. | |
| 2003/0005469 A1 | 1/2003 | Faustman et al. | |
| 2003/0031657 A1 | 2/2003 | Habener et al. | |
| 2004/0028658 A1 | 2/2004 | Faustman | |
| 2004/0031066 A9 | 2/2004 | Faustman et al. | |
| 2004/0229785 A1 | 11/2004 | Faustman | |
| 2005/0043514 A1 | 2/2005 | Fukui et al. | |
| 2005/0158288 A1 | 7/2005 | Faustman | |
| 2005/0158302 A1 | 7/2005 | Faustman et al. | |
| 2005/0244386 A1 | 11/2005 | Habener et al. | |
| 2006/0062769 A1 | 3/2006 | Habener et al. | |
| 2007/0116688 A1 | 5/2007 | Faustman | |
| 2008/0102054 A1 | 5/2008 | Faustman | |
| 2008/0175830 A1 | 7/2008 | Steinman et al. | |
| 2009/0028877 A1 | 1/2009 | Iida et al. | |
| 2010/0068177 A1 | 3/2010 | Faustman | |
| 2010/0298232 A1 | 11/2010 | Liu | |
| 2011/0236374 A1 | 9/2011 | Shitara et al. | |
| 2012/0066777 A1 | 3/2012 | Kawamura et al. | |
| 2012/0115739 A1 | 5/2012 | Schmittling et al. | |
| 2012/0196919 A1 | 8/2012 | Brown et al. | |
| 2014/0096274 A1 | 4/2014 | Quax et al. | |
| 2014/0121123 A1 | 5/2014 | Wang et al. | |
| 2015/0366909 A1 | 12/2015 | Faustman | |

FOREIGN PATENT DOCUMENTS

| | | |
|---|---|---|
| WO | WO-92/04033 A1 | 3/1992 |
| WO | WO-93/02690 A1 | 2/1993 |
| WO | WO-94/09137 A1 | 4/1994 |
| WO | WO-95/24914 A1 | 9/1995 |
| WO | WO-95/25533 A1 | 9/1995 |
| WO | WO-97/08328 A1 | 3/1997 |
| WO | WO-97/13844 A1 | 4/1997 |
| WO | WO-97/21802 A1 | 6/1997 |
| WO | WO-99/53953 A2 | 10/1999 |
| WO | WO-99/59632 A1 | 11/1999 |
| WO | WO-00/53209 A1 | 9/2000 |
| WO | WO-01/44472 A1 | 6/2001 |
| WO | WO-01/91793 A1 | 12/2001 |
| WO | WO-02/26819 A2 | 4/2002 |
| WO | WO-2004/003164 A2 | 1/2004 |
| WO | WO-2005/042727 A2 | 5/2005 |
| WO | WO-2006/109044 A2 | 10/2006 |
| WO | WO-2008/157394 A2 | 12/2008 |
| WO | WO-2010/124259 A1 | 10/2010 |
| WO | WO-2012/122464 A1 | 9/2012 |
| WO | WO-2014/124134 A1 | 8/2014 |
| WO | WO-2015/145360 A1 | 10/2015 |
| WO | WO-2016/187068 A1 | 11/2016 |

OTHER PUBLICATIONS

Allen et al., "Effect of bacillus Calmette-Guerin vaccination on new-onset Type 1 Diabetes," Diabetes Care. 22(10):1703-1707 (1999).

Altomonte et al., "Serum levels of interleukin-1b, tumour necrosis factor-a and interleukin-2 in rheumatoid arthritis. Correlation with disease activity," Clin Rheumatol. 11(2):202-205 (1992).

Anderson et al., "Can stem cells cross lineage boundaries?," Nat Med. 7(4):393-5 (2001).

Anderson et al., "Studies on the cytophilic properties of human beta2 microglobulin," J Immunol. 114(3):997-1000 (1975).

Anderson et al., "The NOD mouse: a model of immune dysregulation," Annu Rev Immunol. 23:447-485 (2005).

Aranda et al., "Analysis of intestinal lymphocytes in mouse colitis mediated by transfer of CD4+, CD45RBhigh T Cells to SCID recipients," J Immunol. 158(7):3464-3473 (1997).

Aristarkhov et al., "E2-C, a cyclin-selective ubiquitin carrier protein required for the destruction of mitotic cyclins," Proc Natl Acad Sci USA. 93(9):4294-9 (1996).

Ashton-Rickardt et al., "Evidence for a differential avidity model of T Cell selection in the thymus," Cell. 76(4):651-63 (1994).

Ashton-Rickardt et al., "Peptide contributes to the specificity of positive selection of CD8+ T Cells in the thymus," Cell. 73(5):1041-9 (1993).

Atkinson et al., "The NOD mouse model of Type 1 Diabetes: As good as it gets?," Nat Med. 5(6):601-604 (1999).

Baeuerle et al., "NF-kappaB: Ten years after," Cell. 87(1):13-20 (1996).

Baeza et al., "Pancreatic regenerating gene overexpression in the nonobese diabetic mouse during active diabetogensis," Diabetes. 45(1):67-70 (1996) (5 pages).

Baeza et al., "Reg protein: a potential beta-cell-specific growth factor?," Diabetes Metab. 22(4):229-234 (1996).

Baeza et al., "Specific reg II gene overexpression in the non-obese diabetic mouse pancreas during active diabetogenesis," FEBS Letters. 416(3):364-8 (1997).

Baik et al., "BCG vaccine prevents insulitis in low dose streptozotocin-induced diabetic mice," Diabetes Res Clin Pract. 46(2):91-97 (1999).

Baldwin, "The NF-$_{kappa}$B and I$_{kappa}$B proteins: new discoveries and insights," Ann Rev Immunol. 14:649-683 (1996).

Ban et al., "Selective death of autoreactive T Cells in human diabetes by TNF or TNF receptor 2 agonism," Proc Natl Acad Sci USA. 105(36):13644-13649 (2008).

Barres, "A new role for glia: generation of neurons!," Cell. 97(6):667-70 (1999).

Baxter et al., "Mycobacteria precipitate an SLE-like syndrome in diabetes-prone NOD mice," Immunology. 83(2):227-231 (1994).

Beg et al., "An essential role for NF-kappaB in preventing TNF-alpha-induced cell death," Science. 274(5288):782-784 (1996).

Bendelac et al., "Syngeneic transfer of autoimmune diabetes from diabetic NOD mice to healthy neonates. Requirement for both L3T4+ and Lyt-2+ T Cells," J Exp Med. 166(4):823-832 (1987).

Bercovici et al., "Systemic administration of agonist peptide blocks the progression of spontaneous CD8-mediated autoimmune diabetes in transgenic mice without bystander damage," J Immunol. 165(1):202-10 (2000).

Bernabeu et al., "Beta2 -microglobulin from serum associates with MHC class I antigens on the surface of cultured cells," Nature. 308:642-645 (1984) (Abstract only) (2 pages).

Bill et al, "Use of soluble MHC class II/peptide multimers to detect antigen-specific T cells in human disease," Arthritis Res. 4:261-265 (2002).

Bjornson et al., "Turning brain into blood: A hematopoietic fate adopted by adult neural stem cells in vitro," Science. 283:534-537 (1999).

Bleumink et al., "Etanercept-induced subacute cutaneous lupus erythematosus" Rheumatology. 40:1317-1319 (2001).

Boches et al, "Role for the adenosine triphosphate-dependent proteolytic pathway in reticulocyte maturation," Science. 215:978-980 (1982).

Brayer et al., "Alleles from chromosomes 1 and 3 of NOD mice combine to influence Sjögren's syndrome-like autoimmune exocrinopathy," J. Rheumatol. 27(8):1896-1904 (2000).

(56) References Cited

OTHER PUBLICATIONS

Brazelton et al., "From marrow to brain: expression of neuronal phenotypes in adult mice," Science. 290:1775-1779 (2000).
Brod et al., "Ingested interferon alpha suppresses Type I diabetes in non-obese diabetic mice," Diabetologia. 41:1227-1232 (1998).
Brod et al., "New clinical trial in newly diagnosed type 1 diabetes," <http://www.diabetesstation.org/articles/brod.htm>, retrieved Jun. 19, 2001 (2 pages).
Brodbeck et al., "Genetic determination of nephrogenesis: the Pax/Eya/Six gene network," Pediatr Nephrol. 19(3):249-255 (2004) (Abstract Only).
Brás et al., "Diabetes-prone NOD mice are resistant to mycobacterium avium and the infection prevents autoimmune disease," Immunology. 89:20-25 (1996).
Bunting et al., "Enforced P-glycoprotein pump function in murine bone marrow cells results in expansion of side population stem cells in vitro and repopulating cells in vivo," Blood. 96(3):902-909 (2000).
Burnham et al., "Oral BCG vaccine in Crohn's disease," Gut. 20:229-233 (1979).
Caetano et al., "Effect of methotrexate (MTX) on NAD(P)+ dehydrogenases of HeLa cells: malic enzyme, 2- oxoglutarate and isocitrate dehydrogenases," Cell Biochem Funct. 15(4):259-264 (1997).
Cairns et al., "New onset systemic lupus erythematosus in a patient receiving etanercept for rheumatoid arthritis," Ann Rheum Dis. 61(11):1031-2 (2002).
Cavallo et al., "BCG vaccine with and without nicotinamide in recent onset IDDM: a multicenter randomized trial," Second Congress of the Immunology of Diabetes Society. 18, A063 (1996).
Charles et al., "Assessment of antibodies to double-stranded DNA induced in rheumatoid arthritis patients following treatment with infliximab, a monoclonal antibody to tumor necrosis factor alpha: findings in open-label and randomized placebo-controlled trials." Arthritis Rheum. 43(11):2383-90 (2000).
Chatenoud et al., "CD3 antibody-induced dominant self tolerance in overtly diabetic NOD mice," J Immunol. 158(6):2947-2954 (1997).
Choi et al., "Prevention of Encephalomyocarditis virus-induced diabetes by live recombinant Mycobacterium bovis Bacillus Calmette-Guérin in susceptible mice," Diabetes. 49:1459-1467 (2000).
Cole et al., "Two ParaHox genes, SpLox and SpCdx, interact to partition the posterior endoderm in the formation of a functional gut," Development. 136(4):541-549 (2009).
Colucci et al., "Programmed cell death in the pathogenesis of murine IDDM: resistance to apoptosis induced in lymphocytes by cyclophosphamide," J Autoimmunity 9:271-276 (1996).
Corbett et al., "Nitric oxide mediates cytokine-induced inhibition of insulin secretion by human islets of langerhans," Proc Natl Acad Sci USA. 90(5):1731-1735 (1993).
Coux et al., "Enzymes catalyzing ubiquitination and proteolytic processing of the p105 precursor of nuclear factor kappaB1," J Biol Chem. 273(15):8820-8828 (1998).
Couzin, "Diabetes studies conflict on power of spleen cells," Science. 311:1694 (2006).
Creasey et al., "Biological effects of recombinant human tumor necrosis factor and its novel muteins on tumor and normal cell lines," Cancer Res. 47(1):145-9 (1987).
Darzynkiewicz et al., "Use of flow and laser scanning cytometry to study mechanisms regulating cell cycle and controlling cell death," Clinics in Laboratory Medicine. 21(4):857-873 (2001).
Dear et al., "The Hox11 gene is essential for cell survival during spleen development," Development. 121:2909-2915 (1995).
Declaration of Dr. Denise Faustman from U.S. Appl. No. 10/358,644, dated on May 13, 2009 (4 pages).
Declaration of Dr. Denise Faustman from U.S. Appl. No. 10/775,487, dated on Jun. 14, 2007 (13 pages).
Declaration of Dr. Denise Faustman from U.S. Appl. No. 10/851,983, dated on Jul. 3, 2007 (7 pages).

Dieguez-Acuna et al., "Characterization of mouse spleen cells by subtractive proteomics," Mol Cell Proteomics. 4(10):1459-1470 (2005).
Dieguez-Acuña et al., "Proteomics identifies multipotent and low oncogenic risk stem cells of the spleen," Int J Biochem Cell Biol. 42(10):1651-1660 (2009) (10 pages).
Dilts et al., "Autoimmune diabetes: The involvement of benign and malignant autoimmunity," J Autoimmun. 12:229-232 (1999).
Dinarello, "Interleukin-1, Interleukin-1 receptors and Interleukin-1 receptor antagonist," Intern Rev Immunol. 16:457-499 (1998).
Driscoll et al., "The proteasome (multicatalytic protease) is a component of the 1500-kDa proteolytic complex which degrades ubiquitin-conjugated proteins," J Biol Chem. 265(9):4789-4792 (1990).
Durand et al., "Mesenchymal lineage potentials of aorta-gonad-mesonephros stromal clones," Heamatologica. 91(9):1172-1179 (2006).
Eglitis et al., "Hematopoietic cells differentiate into both microglia and macroglia in the brains of adult mice," Proc Natl Acad Sci USA. 94:4080-4085 (1997).
Elliott et al., "Effect of Bacille Calmette-Guérin vaccination on C-Peptide secretion in children newly diagnosed with IDDM," Diabetes Care. 21(10):1691-1693 (1998).
Enayati et al., "Association of anti-tumor necrosis factor therapy with the development of multiple sclerosis," J Clin Gastroenterol. 39(4): 303-6 (2005) (Abstract only).
Engleman et al., "Treatment of NZB/NZW F1 hybrid mice with Mycobacterium bovis strain BCG or type II interferon preparations accelerates autoimmune disease," Arthritis Rheum. 24(11):1396-1402 (1981).
EPO Communication Pursuant to Article 94(3) EPC issued in European Patent Application No. 04817543, dated Jan. 22, 2010 (5 pages).
EPO Communication Enclosing Supplementary European Search Report for EP Application No. 03762242, dated May 20, 2009 (8 pages).
EPO Communication for International Application No. PCT/US2014/015101, dated Oct. 15, 2015 (2 pages).
EPO Communication pursuant to 94(3) for European Application No. 12005556.1, dated Jul. 2, 2015 (7 pages).
EPO Communication pursuant to Article 94(3) and Rule 71(1) EPC for European Application No. 00914899.0, dated Mar. 6, 2015 (3 pages).
EPO Communication pursuant to Article 94(3) EPC for European Application No. 00914899.0, dated May 25, 2012 (9 pages).
EPO Communication Pursuant to Article 94(3) EPC issued in European Patent Application No. 03762242, dated Dec. 1, 2011 (4 pages).
EPO Communication Pursuant to Article 94(3) EPC issued in European Patent Application No. 03762242, dated Oct. 30, 2009 (2 pages).
EPO Communication Pursuant to Article 94(3) EPC issued in European Patent Application No. 11008889, dated Mar. 19, 2014 (4 pages).
EPO Communication Pursuant to Article 94(3) EPC issued in European Patent Application No. 11008889, dated Mar. 4, 2013 (4 pages).
EPO Communication Pursuant to Article 94(3) EPC issued in European Patent Application No. 11008889, dated Oct. 27, 2014 (5 pages).
EPO Communication pursuant to Rule 69 EPC for European Application No. 12005556.1, dated Oct. 7, 2014 (2 pages).
EPO Communication under Rule 71(3) EPC for European Application No. 00914899.0, dated Jun. 23, 2015 (6 pages).
EPO Invitation pursuant to Article 94(3) and Rule 71(1) EPC for European Application No. 00914899.0, dated Jun. 2, 2014 (4 pages).
EPO Summons to attend oral proceedings pursuant to Rule 115(1) EPC for European Application No. 00914899.0, dated Nov. 12, 2014 (6 pages).
EPO Summons to attend oral proceedings pursuant to Rule 115(1) EPC for European Application No. 12005556.1, dated Dec. 18, 2015 (4 pages).

(56) References Cited

OTHER PUBLICATIONS

Examination Report issued in Australian Patent Application No. 2003247840, dated Jan. 31, 2008 (4 pages).
Examiner's Report for Canadian Application No. 2,543,745, dated Jul. 15, 2011 (4 pages).
Extended European Search Report for European Application No. 12005556.1, dated Sep. 2, 2014 (8 pages).
Extended European Search Report for European Patent Application No. 11008889, dated Apr. 12, 2012 (10 pages).
Extended European Search Report issued in European Application No. 14189654, dated Feb. 16, 2015 (7 pages).
Eytan et al., "ATP-dependent incorporation of 20S protease into the 26S complex that degrades proteins conjugated to ubiquitin," Proc Natl Acad Sci USA. 86:7751-7755 (1989).
Fan et al., "Generation of p50 subunit of NF-kappaB by processing of p105 through an ATP-dependent pathway," Nature. 354:395-398 (1991).
Faustman et al., "Abnormal T-lymphocyte subsets in Type I Diabetes," Diabetes. 38:1462-1468 (1989).
Faustman et al., "Linkage of faulty major histocompatibility complex class I to autoimmune diabetes," Science. 254:1756-1761 (1991).
Faustman et al., "Murine pancreatic beta-Cells express H-2K and H-2D but not Ia antigens," J Exp Med. 151:1563-1568 (1980).
Faustman et al., "Prevention of xenograft rejection by masking donor HLA class I antigens," Science. 252:1700-1702 (1991).
"Stem cells in the spleen: Therapeutic potential for Sjogren's syndrome, type I diabetes, and other disorders," available in PMC Jul. 21, 2014, published in final edited form as: Int J Biochem Cell Biol. 42(10):1576-9 (2010) (8 pages).
Faustman et al., "T-lymphocyte changes linked to autoantibodies. Association of insulin autoantibodies with CD4+CD45R+ lymphocyte subpopulation in prediabetic subjects," Diabetes. 40:590-597 (1991).
Faustman et al., "TNF receptor 2 pathway: drug target for autoimmune diseases," Nat Rev Drug Discov. 9(6):482-93 (2010).
Feldman et al., "Anti-TNFalpha therapy is useful in rheumatoid arthritis and Crohn's disease: Analysis of the mechanism of action predicts utility in other diseases," Transplant Proc. 30(8):4126-4127 (1998).
Feldman et al., "Role of cytokines in rheumatoid arthritis," Annu Rev Immunol. 14:397-440 (1996) (abstract only).
Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11:Abstract 578 (2002).
Fischer et al., "A TNF receptor 2 selective agonist rescues human neurons from oxidative stress-induced cell death," PloS One. 6(11):e27621 (2011) (11 pages).
Fischer et al., "An improved flow cytometric assay for the determination of cytotoxic T lymphocyte activity," J Immunol Methods. 259:159-169 (2002).
Foulis, "C.L. Oakley lecture (1987). The pathogenesis of beta cell destruction in Type I (insulin-dependent) diabetes mellitus," J Pathol. 152(3):141-148 (1987).
Fu et al., "Antigen processing and autoimmunity: Evaluation of mRNA abundance and function of HLA-Linked genes," Ann NY Acad Sci. 842:138-155 (1998).
Fu et al., "Defective major histocompatibility complex class I expression on lymphoid cells in autoimmunity," J Clin Invest. 91:2301-2307 (1993).
Fukada et al., "Two signals are necessary for cell proliferation induced by a cytokine receptor gp130: Involvement of STAT3 in anti-apoptosis," Immunity. 5:449-460 (1996).
Gage et al., "Multipotent progenitor cells in the adult dentate gyrus," J Neurobiol. 36:249-266 (1998).
Gage, "Mammalian neural stem cells," Science. 287:1433-1438 (2000).
Galaria et al., "Leukocytoclastic vasculitis due to etanercept," J Rheumatol. 27(8):2041-4 (2000) (Abstract only).
Ganoth et al., "A multicomponent system that degrades proteins conjugated to ubiquitin. Resolution of factors and evidence for ATP-dependent complex formation," J Biol Chem. 263(25):12412-12419 (1988).
Gaur et al., "Induction of islet allotolerance in nonhuman primates," Ann NY Acad Sci. 958:199-203 (2002).
Gazda et al., "Diabetes results from a late change in the autoimmune response of NOD mice," J Autoimmun. 10:261-270 (1997).
Gazda et al., "Regulation of autoimmune diabetes: characteristics of non-islet-antigen specific therapies," Immunol Cell Biol. 74: 401-407 (1996).
Genestier et al., "Immunosuppressive properties of methotrexate: Apoptosis and clonal deletion of activated peripheral T Cells," J Clin Invest. 102(2):322-328 (1998).
Gerich et al., "Advances in diabetes for the millenium: Understanding insulin resistance," MedGenMed. 6(3 Suppl):11 (2004) (9 pages).
Ghosh et al., "Activation in vitro of NF-kappaB by phosphorylation of its inhibitor IkappaB," Nature. 344:678-682 (1990).
Glas et al., "The CD8+ T Cell repertoire in beta2-microglobulin-deficient mice is biased towards reactivity against self-major histocompatibility class I," J Exp Med. 179(2):661-672 (1994).
Goldberg, "Functions of the proteasome: The lysis at the end of the tunnel," Science. 268:522-523 (1995).
Goldberg, "The mechanism and functions of ATP-dependent proteases in bacterial and animal cells," Eur J Biochem. 203:9-23 (1992).
Gottlieb et al., "Cell acidification in apoptosis: Granulocyte colony-stimulating factor delays programmed cell death in neutrophils by up-regulating the vacuolar $H^+$-ATPase," Proc Natl Acad Sci USA. 92:5965-5968 (1995).
Graves et al., "Lack of association between early childhood immunizations and beta-Cell autoimmunity," Diabetes Care 22:1694-1697 (1999).
Grewal et al., "Local expression of transgene encoded TNFalpha in islets prevents autoimmune diabetes in nonobese diabetic (NOD) mice by preventing the development of auto-reactive islet-specific T Cells," J Exp Med. 184:1963-1974 (1996).
Grilli et al., "Neuroprotection by aspirin and sodium salicylate through blockade of NF-kappaB activation," Science. 274:1383-1385 (1996).
Gronostajski et al., "The ATP dependence of the degradation of short- and long-lived proteins in growing fibroblasts," J Biol Chem. 260(6):3344-3349 (1985).
Gueckel et al., "Mutations in the yeast proteasome beta-Type subunit Pre3 uncover position-dependent effects on proteasomal peptidase activity and in vivo function," J Biol Chem. 273(31):19443-19452 (1998).
Gupta, "Molecular steps of tumor necrosis factor receptor-mediated apoptosis," Curr Mol Med. 1(3):317-324 (2001).
Haas et al., "Pathways of ubiquitin conjugation," FASEB J. 11:1257-1268 (1997).
Hao et al., "Effect of mycophenolate mofetil on islet allografting to chemically induced or spontaneously diabetic animals," Transplant Proc. 24(6): 2843-2844 (1992).
Harada et al., "Prevention of overt diabetes and insulitis in NOD mice by a single BCG vaccination," Diabetes Res Clin Pract. 8:85-89 (1990).
Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).
Hayashi et al., "Essential role of human leukocyte antigen-encoded proteasome subunits in NF-kappaB activation and prevention of tumor necrosis factor-alpha-induced apoptosis," J Biol Chem. 275(7):5238-5247 (2000).
Hayashi et al., "NOD mice are defective in proteasome production and activation of NF-kappaB," Mol Cell Biol. 19(12):8646-8659 (1999).
Hershko et al., "The ubiquitin system for protein degradation," Annu Rev Biochem. 61: 761-807 (1992).

(56) References Cited

OTHER PUBLICATIONS

Hester et al., "Studies on the cytophilic properties of human beta2-microglobulin. II. The role of histocompatibility antigens," Scand J Immunol. 9(2):125-134 (1979).
Hoffmann et al. "Large-scale in vitro expansion of polyclonal human CD4(+)CD25high regulatory T cells," Blood. 104(3):895-903 (2004).
Horsfall et al., "Characterization and specificity of B-cell responses in lupus induced by Mycobacterium bovis in NOD/Lt mice," Immunology 95:8-17 (1998).
Horwitz et al., "Recombinant baccillus Calmette-Guérin (BCG) vaccines expressing the Mycobacterium tuberculosis 30-kDa major secretory protein induce greater protective immunity against tuberculosis than conventional BCG vaccines in a highly susceptible animal model," Proc Natl Acad Sci USA. 97(35):13853-13858 (2000).
Hostikka et al., "The mouse Hoxc11 gene: genomic structure and expression pattern," Mech Dev. 70(1-2):133-145 (1998) (Abstract Only).
Hsu et al., "TRADD-TRAF2 and TRADD-FADD interactions define two distinct TNF receptor 1 signal transduction pathways," Cell. 84:299-308 (1996).
Humphreys-Beher et al., "New concepts for the development of autoimmune exocrinopathy derived from studies with the NOD mouse model," Arch Oral Biol. 44(Suppl 1):S21-S25 (1999) (Abstract Only) (2 pages).
Hyafil et al., "Dissociation and exchange of the beta2-micoglobulin subunit of HLA-A and HLA-B antigens," Proc Natl Acad Sci USA. 76(11):5834-5838 (1979).
Hymowitz et al., "Toward small-molecule agonists of TNF receptors," Nat Chem Biol. 1(7):353-354 (2005).
International Search Report and Written Opinion for International Patent Application No. PCT/US2014/15101, dated Jun. 24, 2014 (14 pages).
International Search Report for International Application No. PCT/US00/06239 dated Jul. 31, 2000 (2 pages).
International Search Report for International Application No. PCT/US2004/037998, dated Feb. 28, 2008 (2 pages).
International Search Report for International Patent Application No. PCT/US03/20578, dated Apr. 27, 2004 (1 page).
International Search Report for International Patent Application No. PCT/US03/36531, dated Jul. 14, 2004 (1 page).
Jackson et al., "Hematopoietic potential of stem cells isolated from murine skeletal muscle," Proc Natl Acad Sci USA. 96(25):14482-14486 (1999).
Jacob et al., "Monoclonal anti-tumor necrosis factor antibody renders non-obese diabetic mice hypersensitive to irradiation and enhances insulitis development," Int Immunol. 4(5):611-614 (1992).
Jacob et al., "Prevention of diabetes in nonobese diabetic mice by tumor necrosis factor (TNF): Similarities between TNF-alpha and interleukin 1," Proc Natl Acad Sci USA. 87:968-972 (1990).
Jacob et al., "Tumour necrosis factor-alpha in murine autoimmune 'lupus' nephritis," Nature. 331:356-358 (1988).
Jakubowski et al., "Phase I trial of intramuscularly administered tumor necrosis factor in patients with advanced cancer," J Clin Oncol. 7(3):298-303 (1989).
Jarrett et al., "Anti-tumor necrosis factor-alpha therapy-induced vasculitis: case series," J Rheumatol. 30(10):2287-91 (2003) (Absract only).
Jiang et al., "Pluripotency of mesenchymal stem cells derived from adult marrow," Nature. 418:41-49 (2002).
Johansson et al., "Identification of a neural stem cell in the adult mammalian central nervous system," Cell. 96:25-34 (1999).
Juang et al., "Beneficial influence of glycemic control upon the growth and function of transplanted islets," Diabetes 43:1334-1339 (1994).
Kaijzel et al., "Functional analysis of a human tumor necrosis factor alpha (TNF-alpha) promoter polymorphism related to joint damage in rheumatoid arthritis," Mol Med. 4:724-733 (1998).

Kanzler et al., "Hox11 acts cell autonomously in spleen development and its absence results in altered cell fate of mesenchymal spleen precursors," Devel Biol. 234:231-243 (2001).
Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).
Kawasaki et al., "Prevention of type 1 diabetes: from the view point of beta cell damage," Diabetes Res Clin Pract. 66:S27-S32 (2004).
Kieran et al., "The DNA binding subunit of NF- kappaB is identical to factor KBF1 and homologous to the rel oncogene product," Cell. 62:1007-1018 (1990).
Klingensmith et al., "Vaccination with BCG at diagnosis does not alter the course of IDDM," Diabetes 57th Annual Meeting and Scientific Sessions, Jun. 21-24, Boston MA. 40(Suppl 1):193A, 0744 (1997) (3 pages) (Abstract Only).
Klinkhoff, "Biological agents for rheumatoid arthritis: targeting both physical function and structural damage," Drugs. 64(12):1267-83 (2004) (Abstract only).
Koarada et al., "B Cells lacking RP105, A novel B cell antigen, in systemic lupus erythematosus," Arthritis & Rheumatism. 42(12):2593-2600 (1999).
Kodama et al., "Islet regeneration during the reversal of autoimmune diabetes in NOD mice," Science. 302:1223-1227 (2003).
Kodama et al., "Regenerative medicine: A radical reappraisal of the spleen," Trends Mol Med. 11(6):271-276 (2005).
Kodama et al., "The therapeutic potential of tumor necrosis factor for autoimmune disease: A mechanically based hypothesis," Cell Mol Life Sci. 62:1850-1862 (2005).
Kopp et al., "Inhibition of NF-kappaB by sodium salicylate and aspirin," Science. 265:956-959 (1994).
Kouskoff et al., "Organ-specific disease provoked by systemic autoimmunity," Cell. 87(5):811-822 (1996) (Abstract Only).
Koyama et al., "Hox11 genes establish synovial joint organization and phylogenetic characteristics in developing mouse zeugopod skeletal elements," Development. 137(22): 3795-800 (2010) (Abstract Only).
Krause et al., "Multi-organ, multi-lineage engraftment by a single bone marrow-derived stem cell," Cell. 105:369-377 (2001).
Kuehnle et al., "The therapeutic potential of stem cells from adults," BMJ. 325:372-376 (2002).
Kwon et al., "Evidence for involvement of the proteasome complex (26S) and NFkappaB in IL-1beta-induced nitric oxide and prostaglandin production by rat islets and RINm5F Cells" Diabetes. 47:583-591 (1998).
Kwon et al., "Interleukin-1beta -induced nitric oxide synthase expression by rat pancreatic beta-cells: Evidence for the involvement of nuclear factor kappaB in the signaling mechanism," Endocrinology. 136(11):4790-4795 (1995).
Laakko et al., "Versatility of merocyanine 540 for the flow cytometric detection of apoptosis in human and murine cells," J Immunol Methods. 261:129-139 (2002).
Lahav-Baratz et al., "Reversible phosphorylation controls the activity of cyclosome-associated cyclin-ubiquitin ligase," Proc Natl Acad Sci USA 92:9303-9307 (1995).
Lakey et al., "BCG immunotherapy prevents recurrence of diabetes in islet grafts transplanted into spontaneously diabetic NOD mice," Transplantation. 57(8):1213-1217 (1994).
Lammert et al., "Induction of pancreatic differentiation by signals from blood vessels," Science. 294:564-567 (2001).
Lanza et al., "Transplantation of encapsulated canine islets into spontaneously diabetic BB/Wor rats without immunosuppression," Endocrinology. 131(2):637-642 (1992).
Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).
Lawrence et al., "Differential hepatocyte toxicity of recombinant Apo2L/TRAIL versions," Nat Med. 7(4):383-385 (2001).
Lewis et al., "Integrins regulate the apoptotic response to DNA damage through modulation of p53," Proc Natl Acad Sci USA. 99(6):3627-3632 (2002).

(56) References Cited

OTHER PUBLICATIONS

Li et al., "Use of Donor beta2-Microglobulin-Deficient Transgenic Mouse Liver Cells for Isografts, Allografts, and Xenografts," *Transplantation*. 55(4):940-946, 1993.
Li et al., "Abnormal class I assembly and peptide presentation in the nonobese diabetic mouse," Proc Natl Acad Sci USA. 91:11128-11132 (1994).
Li et al., "Reduced expression of peptide-loaded HLA class I molecules on multiple sclerosis lymphocytes," Ann Neurol. 38:147-154 (1995).
Lipsky et al., "Infliximab and methotrexate in the treatment of rheumatoid arthritis," N Eng J Med. 343:1594-1602 (2000).
Ljunggren et al., "MHC class I expression and CD8+ T cell development in TAP1/beta2-microglobulin double mutant mice," Int Immunol. 7(6):975-984 (1995).
Loetscher et al., "Human tumor necrosis factor alpha (TNF alpha) mutants with exclusive specificity for the 55-kDa or 75-kDa TNF receptors," J Biol Chem. 268(35):26350-26357 (1993).
Macchi et al., "Impaired apoptosis in mitogen-stimulated lymphocytes of patients with multiple sclerosis," NeuroReport. 10(25):399-402 (1999).
Mak et al., "Signaling for survival and apoptosis in the immune system," Arthritis Res. 4(Suppl 3):S243-S252 (2002).
Markiewicz et al., "Long-term T cell memory requires the surface expression of self-peptide/major histocompatibility complex molecules," Proc Natl Sci USA. 95:3065-3070 (1998).
Markmann et al., "Indefinite survival of MHC class I-deficient murine pancreatic islet allografts," Transplantation. 54(6):1085-1089 (1992).
Marriott, "TNF-alpha antagonists: Monoclonal antibodies, soluble receptors, thalidomide and other novel approaches," Expert Opin Invest Drugs. 6(8):1105-1108 (1997).
Matsumoto et al., "Liver organogenesis promoted by endothelial cells prior to vascular function," Science. 294:559-563 (2001).
Mayer-Proschel et al., "Isolation of lineage-restricted neuronal precursors from multipotent neuroepithelial stem cells," Neuron. 19:773-785 (1997).
McGuire et al., "An enzyme related to the high molecular weight multicatalytic proteinase, macropain, participates in a ubiquitin-mediated, ATP-stimulated proteolytic pathway in soluble extracts of BHK 21/C13 fibroblasts," Biochim Biophys Acta. 967:195-203 (1988).
McInerney et al., "Prevention of insulitis and diabetes onset by treatment with complete Freund's adjuvant in NOD mice," Diabetes. 40:715-725 (1991).
McKay, "Mammalian deconstruction for stem cell reconstruction," Nat Med. 6(7):747-748 (2000).
Mercurio et al., "p105 and p98 precursor proteins play an active role in NF-Kappa B-mediated signal transduction," Genes Dev. 7:705-718 (1993).
Mestas et al., "Of mice and not men: Differences between mouse and human immunology," J Immunol. 172:2731-2738 (2004).
Mezey et al., "Turning blood into brain: Cells bearing neuronal antigens generated in vivo from bone marrow," Science. 290:1779-1782 (2000).
Miller et al., "Both the Lyt-2+ and L3T4+ T cell subsets are required for the transfer of diabetes in nonobese diabetic mice," J Immunol. 140(3):52-58 (1988).
Mittelman et al., "A phase I pharmacokinetic study of recombinant human tumor necrosis factor administered by a 5-day continuous infusion," Invest New Drugs. 10(3):183-190 (1992).
Miyazaki et al., "Predominance of T lymphocytes in pancreatic islets and spleen of pre-diabetic non-obese diabetic (NOD) mice: A longitudinal study," Clin Exp Immunol. 60:622-630 (1985).
Moreland et al., "Etanercept therapy in rheumatoid arthritis: a randomized, controlled trial," Ann Intern Med. 130(6):478-486 (1999).
Morrison, "Stem cell potential: Can anything make anything?" Curr Biol. 11:R7-R9 (2001).

Murthi et al., "Novel homeobox genes are differentially expressed in placental microvascular endothelial cells compared with macrovascular cells compared with macrovascular cells," Placenta. 29(7):624-630 (2008) (Abstract Only).
Nomikos et al., "Combined treatment with nicotinamide and desferrioxamine prevents islet allograft destruction in NOD mice," Diabetes. 35:1302-1304 (1986).
Offield et al., "PDX-1 is required for pancreatic outgrowth and differentiation of the rostral duodenum," Development. 122:983-995 (1996).
Ono et al., "IDDM in BB rats. Enhanced MHC Class I heavy-chain gene expression in pancreatic islets," Diabetes. 37:1411-1418 (1988).
Orlowski, "The multicatalytic proteinase complex, a major extralysosomal proteolytic system," Biochemistry. 29(45):10289-10297 (1990).
Osorio et al., "Beta-2 microglobulin gene disruption prolongs murine islet allograft survival in NOD mice," Transplant Proc. 26(2):752 (1994).
Palombella et al., "The ubiquitin-proteasome pathway is required for processing the NF-$_{kappa}$B1 precursor protein and the activation of NF-$_{kappa}$B," Cell. 78:773-785 (1994).
Paolillo et al., "The effect of bacille calmette-guérin on the evolution of new enhancing lesions to hypointense T1 lesions in relapsing remitting MS," J Neurol. 250:247-248 (2003).
Pestano et al., "Inactivation of misselected CD8 T cells by CD8 gene methylation and cell death," Science. 284(5417):1187-91 (1999).
Petersen et al., "Bone marrow as a potential source of hepatic oval cells," Science. 284(5417):1168-70 (1999).
Pontesilli et al., "Circulating lymphocyte populations and autoantibodies in non-obese diabetic (NOD) mice: A longitudinal study," Clin Exp Immunol. 70(1):84-93 (1987).
Pozzilli, "BCG vaccine in insulin-dependent diabetes mellitus," Lancet. 349(9064):1520-1 (1997).
Prieto et al., "Apoptotic rate: A new indicator for the quantification of the incidence of apoptosis in cell cultures," Cytometry. 48(4):185-93 (2002).
Qin et al., "BCG vaccination prevents insulin-dependent diabetes mellitus (IDDM) in NOD mice after disease acceleration with cyclophosphamide," J Autoimmun.10:271-278 (1997).
Qin et al., "Complete Freund's adjuvant-induced T cells prevent the development and adoptive transfer of diabetes in nonobese diabetic mice," J Immunol. 150(5):2072-80 (1993).
Quintana et al., "Experimental autoimmune myasthenia gravis in naïve non-obese diabetic (NOD/LtJ) mice: Susceptibility associated with natural IgG antibodies to the acetylcholine receptor," Int Immunol. 15(1):11-16 (2003).
Raab et al., "In vitro evaluation of methotrexate and azathioprine for antipsoriatic activity," Arch Derm Res. 253:77-84 (1975).
Rabinovitch et al., "TNF-alpha down-regulates type 1 cytokines and prolongs survival of syngeneic islet grafts in nonobese diabetic mice," J Immunol. 159(12):6298-6303 (1997).
Rabinovitch et al., "Tumor necrosis factor mediates the protective effect of freund's adjuvant against autoimmune diabetes in BB rats," J Autoimmun. 8(3):357-366 (1995).
Rajagopalan et al., "Pathogenic anti-DNA autoantibody-inducing T helper cell lines from patients with active lupus nephritis: Isolation of CD4-8- T helper cell lines that express the gamma delta T-cell antigen receptor," Proc Natl Acad Sci USA. 87:7020-7024 (1990).
Raju et al., "Characterization and developmental expression of Tlx-1, the murine homolog of HOX11," Mech Dev. 44(1):51-64 (1993).
Ramiya et al., "Reversal of insulin-dependent diabetes using islets generated in vitro from pancreatic stem cells," Nat Med. 6(3):278-282 (2000).
Rath et al., "TNF-induced signaling in apoptosis," J Clin Immunol. 19(6):350-364 (1999).
Rechsteiner, "Ubiquitin-mediated pathways for intracellular proteolysis," Annu Rev Cell Biol. 3:1-30 (1987).
Rietze et al., "Purification of a pluripotent neural stem cell from the adult mouse brain," Nature. 412(6848):736-739 (2001).
Ristori et al., "Use of Bacille Calmette-Guérin (BCG) in multiple sclerosis," Neurology. 53:1588-1589 (1999).

(56) References Cited

OTHER PUBLICATIONS

Roberts et al., "Developmental expression of Hox11 and specification of splenic cell fate," Am J Pathol. 146(5):1089-1101 (1995).
Roberts et al., "Hox11 controls the genesis of the spleen," Nature. 368:747-749 (1994).
Robertson et al., "Preservation of insulin mRNA levels and insulin secretion in HIT cells by avoidance of chronic exposure to high glucose concentrations," J Clin Invest. 90:320-325 (1992).
Robinson et al., "A novel NOD-derived murine model of primary Sjögren's Syndrome," Arth Rheum. 41(1):150-156 (1998).
Robinson et al., "Elevated levels of cysteine protease activity in saliva and salivary glands of the nonobese diabetic (NOD) mouse model for Sjögren Syndrome," Proc Natl Acad Sci USA. 94:5767-5771 (1997).
Rolfe et al., "The ubiquitin-mediated proteolytic pathway as a therapeutic area," J Mol Med. 75:5-17 (1997).
Rosenthal, "Prometheus's vulture and the stem-cell promise," N Engl J Med. 349(3):267-74 (2003).
Ryu et al., "Reversal of established autoimmune diabetes by restoration of endogenous beta cell function," J Clin Invest. 108(1):63-72 (2001).
Sadelain et al., "Prevention of type I diabetes in NOD mice by adjuvant immunotherapy," Diabetes. 39:583-589 (1990).
Sandborn et al., "Antitumor necrosis factor therapy for inflammatory bowel disease: a review of agents, pharmacology, clinical results, and safety," Inflamm Bowel Dis. 5(2):119-33 (1999) (Abstract only).
Sandborn, "Strategies targeting tumor necrosis factor in Crohn's disease," Acta Gastroenterol Belg. 64(2):170-2 (2001) (Abstract only).
Sarin et al., "Cytotoxic effect of TNF and lymphotoxin on T lymphoblasts," J Immunol. 155:3716-3718 (1995).
Satoh et al., "Inhibition of type I diabetes in BB rats with recombinant human tumor necrosis factor-alpha," J Immunol. 145(5):1395-1399 (1990).
Satoh et al., "Recombinant human tumor necrosis factor alpha suppresses autoimmune diabetes in non obese diabetic mice," J Clin Invest. 84:1345-1348 (1989).
Schaible, "Long term safety of infliximab," Can J Gastroenterol. 14(Suppl C):29C-32C (2000) (Abstract only).
Schatz et al., "Defective inducer T-cell function before the onset of insulin-dependent diabetes mellitus," J Autoimmun. 4:125-136 (1991).
Schmidt et al., "Interspecies exchange of beta2-microglobulin and associated MHC and differentiation antigens," Immunogenetics. 13(6):483-91 (1981).
Schuppan, "Current concepts of Celiac Disease pathogenesis," Gastroenterology. 119(1):234-242 (2000).
Sears et al., "NF-kappaB p105 processing via the ubiquitin-proteasome pathway," J Biol Chem. 273(3):1409-1419 (1998).
Serrano et al., "Non-HLA associations with autoimmune diseases," Autoimmun Rev. 5:209-214 (2006).
Serreze et al., "Th1 to Th2 cytokine shifts in nonobese diabetic mice: Sometimes an outcome, rather than the cause, of diabetes resistance elicited by immunostimulation," J Immunol. 166:1352-1359 (2001).
Serup et al., "Islet and stem cell transplantation for treating diabetes," BMJ. 322:29-32 (2001).
Serup, "Panning for pancreatic stem cells," Nat Genet. 25:134-135 (2000).
Shakoor et al., "Drug-induced systemic lupus erythematosus associated with etanercept therapy," Lancet. 359(9306):579-80 (2002) (Abstract only).
Shehadeh et al., "Effect of adjuvant therapy on development of diabetes in mouse and man," Lancet. 343:706-707 (1994).
Shehadeh et al., "Repeated BCG vaccination is more effective than a single dose in preventing diabetes in non-obese diabetic (NOD) mice," Isr J Med Sci. 33(11):711-715 (1997).
Shihabuddin et al., "Adult spinal cord stem cells generate neurons after transplantation in the adult dentate gyrus," J Neurosci. 20(23):8727-8735 (2000).

Shohami et al., "Dual role of tumor necrosis factor alpha in brain injury," Cytokine Growth Factor Rev. 10:119-130 (1999).
Silva et al., "Prevention of autoimmune diabetes through immunostimulation with Q fever complement-fixing antigen," Ann NY Acad Sci. 1005:423-430 (2003).
Singh et al., "Can progression of IDDM be prevented in newly diagnosed patients by BCG immunotherapy?" Diabetes Metab Rev. 13(4):320-321 (1997).
Slack, "Stem cells in epithelial tissues," Science. 287:1431-1433 (2000).
Song et al., "Tumor necrosis factor-related apoptosis-inducing ligand (TRAIL) is an inhibitor of autoimmune inflammation and cell cycle progression," J Exp Med. 191(7):1095-1103 (2000).
Speiser et al., "Loss of ATP-dependent proteolysis with maturation of reticulocytes and erythrocytes," J Biol Chem. 257(23):14122-14127 (1982).
Sreenan et al., "Increased beta-Cell proliferation and reduced mass before diabetes onset in the nonobese diabetic mouse," Diabetes. 48:989-996 (1999).
Stephens et al., "Protection of NIT-1 pancreatic beta-cells from immune attack by inhibition of NF-kappaB," J Autoimmun. 10:293-298 (1997).
Storms et al., "Hoechst dye efflux reveals a novel CD7+CD34- lymphoid progenitor in human umbilical cord blood," Blood. 96(6):2125-2133 (2000).
Sun et al., "MHC class I multimers," Arthritis Res. 3(5):265-269 (2001).
Supplementary Partial European Search Report for European Application No. 04817543, dated Oct. 6, 2009 (4 pages).
Swale et al., "Etanercept-induced systemic lupus erythematosus," Clin Exp Dermatol. 28:604-607 (2003).
Swirski et al., "Identification of splenic reservoir monocytes and their deployment to inflammatory sites," available in PMC Jan. 7, 2010, published in final edited form as: Science. 325(5940):612-616 (2009) (12 pages).
Szodoray et al., "Programmed cell death in rheumatoid arthritis peripheral blood T-cell subpopulations determined by laser scanning cytometry," Lab Invest. 83(12):1839-1848 (2003).
Tamura et al., "In vivo differentiation of stem cells in the aorta-gonad-mesonephros region of mouse embryo and adult bone marrow," Exp Hematol. 30(8):957-966 (2002) (Abstract Only).
Tartaglia et al., "The two different receptors for tumor necrosis factor mediate distinct cellular responses," Proc Natl Acad Sci USA. 88:9292-9296 (1991).
Tavernier et al., "Analysis of the structure-function relationship of tumour necrosis factor. Human/mouse chimeric TNF proteins: general properties and epitope analysis," J Mol Biol. 211(2):493-501 (1990).
Terada et al., "Bone marrow cells adopt the phenotype of other cells by spontaneous cell fusion," Nature. 416:542-545 (2002).
Beers et al. Disorders of Carbohydrate Metabolism: Diabetes Mellitus. *The Merck Manual of Diagnosis and Therapy, 17th Ed*. Merck Research Laboratories, 165-171, 1999.
Thomas et al., "Demyelination during anti-tumor necrosis factor alpha therapy with infliximab for Crohn's disease," Inflamm Bowel Dis. 10(1):28-31 (2004) (Abstract only).
Toma et al., "Isolation of multipotent adult stem cells from the dermis of mammalian skin," Nat Cell Bio. 3:778-784 (2001).
Totpal et al., "TNF and its receptor antibody agonist differ in mediation of cellular responses," J Immunol. 153:2248-2257 (1994).
Townsley et al., "Dominant-negative cyclin-selective ubiquitin carrier protein E2-C/UbcH10 blocks cells in metaphase," Proc Natl Acad Sci USA. 94:2362-2367 (1997).
Tran et al., "Reversal of Sjögren's-like syndrome in non-obese diabetic mice," Ann Rheum Dis. 66:812-814 (2007).
Trowsdale et al., "Sequences encoded in the class II region of the MHC related to the 'ABC' superfamily of transporters," Nature. 348:741-744 (1990).
Ulaeto et al., "A T-cell dormant state in the autoimmune process of nonobese diabetic mice treated with complete Freund's adjuvant," Proc Natl Acad Sci USA. 89:3927-3931 (1992).
Van der Kooy et al., "Why stem cells?," Science. 287:1439-1441 (2000).

(56) References Cited

OTHER PUBLICATIONS

Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).
Van Noort et al., "Cell biology of autoimmune diseases," Int Rev Cytol. 178:127-206 (1998).
Van Zee et al., "A human tumor necrosis factor (TNF) alpha mutant that binds exclusively to the p55 TNF receptor produces toxicity in the baboon," J Exp Med. 179(4):1185-1191 (1994).
Vermeire et al., "Autoimmunity associated with anti-tumor necrosis factor alpha treatment in Crohn's disease: a prospective cohort study," Gastroenterology. 125(1):32-9 (2003) (Abstract only).
Vidal-Puig et al., "Tolerance to peripheral tissue Is transient and maintained by tissue-specific class I expression," Transplant Proc. 26(6):3314-6 (1994).
Vogel, "Stem cell research. Studies cast doubt on plasticity of adult cells," Science. 295:1989,1991 (2002).
Von Herrath et al., "In vivo treatment with a MHC class I-restricted blocking peptide can prevent virus-induced autoimmune diabetes," J Immunol. 161:5087-5096 (1998).
Wang et al., "Prevention of recurrence of IDDM in islet-transplanted diabetic NOD mice by adjuvant immunotherapy," Diabetes. 41:114-117 (1992).
Watt et al., "Out of eden: stem cells and their niches," Science. 287:1427-1430 (2000).
Waxman et al., "Demonstration of two distinct high molecular weight proteases in rabbit reticulocytes, one of which degrades ubiquitin conjugates," J Biol Chem. 262(6):2451-2457 (1987).
Weissman, "Translating stem and progenitor cell biology to the clinic: barriers and opportunities," Science. 287:1442-1446 (2000).
Welborn et al., "A human tumor necrosis factor p75 receptor agonist stimulates in vitro T cell proliferation but does not produce inflammation or shock in the baboon," J Exp Med. 184(1):165-171 (1996).
Wellik et al., "Hox11 paralogous genes are essential for metanephric kidney induction," Genes Dev. 16:1423-1432 (2002).
Wellik, "The role of Hox11 paralogous genes in prostate development," Grant Detail. (2009) (1 page)(Abstract only).
Weringer et al., "Identification of T cell subsets and Class I and Class II antigen expression in islet grafts and pancreatic islets of diabetic BioBreeding/Worcester rats," Am J Pathol. 132(2):292-303 (1988).
Wicker et al., "Transfer of autoimmune diabetes mellitus with splenocytes from nonobese diabetic (NOD) mice," Diabetes. 35:855-860 (1986).
Willis et al., "Type 1 Diabetes in insulin-treated adult-onset diabetic subjects," Diabetes Res Clin Pract. 42:49-53 (1998).
Winston, "Embryonic stem cell research: the case for . . . ," Nat Med. 7(4):396-397 (2001).
Wong et al., "Identification of an MHC class I-restricted autoantigen in Type I Diabetes by screening an organ-specific cDNA library," Nat Med. 5(9):1026-1031 (1999).
Written Opinion for International Application No. PCT/US2004/037998, dated Feb. 28, 2008 (3 pages).
Xu et al., "MHC/peptide tetramer-based studies of T cell function," J Immunol Methods. 268:21-28 (2002).
Yagi et al., "Possible mechanism of the preventive effect of BCG against diabetes mellitus in NOD Mouse. I. Generation of suppressor macrophages in spleen cells of BCG-vaccinated mice," Cell Immunol. 138:130-141 (1991).
Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).
Yan et al., "Reduced expression of Tap1 and Lmp2 antigen-processing genes in the nonobese diabetic (NOD) mouse due to a mutation in their shared bidirectional promoter," J Immunol. 159:3068-3080 (1997).

Yang et al., "Effect of tumor necrosis factor alpha on insulin-dependent diabetes mellitus in NOD Mice. I. The early development of autoimmunity and the diabetogenic process," J Exp Med. 180:995-1004 (1994).
Ying et al., "Changing potency by spontaneous fusion," Nature. 416:545-548 (2002).
Zulewski et al., "Multipotential nestin-positive stem cells isolated from adult pancreatic islets differentiate ex vivo into pancreatic endocrine, exocrine, and hepatic phenotypes," Diabetes. 50:521-533 (2001).
Zöller et al., "Apoptosis resistance in peripheral blood lymphocytes of alopecia areata patients," Retrieved from Science Direct, published in: J Autoimmun. 23(3):241-256 (2004) (30 pages).
Vogel, "Studies cast doubt on plasticity of adult cells," Science. 295:1989&1991 (2002).
Watt et al., "Specific alternative HOX11 transcripts are expressed in paediatric neural tumours and T-cell acute lymphoblastic leukaemia," Gene. 323:89-99 (2003) (Abstract only).
Wilson et al., "Bone-marrow haematopoietic-stem-cell niches," Nat Rev Immunol. 6(2):93-106 (2006).
Kopp et al., "Inhibition of NF-kappaB by sodium salicylate and aspirin," Science. 265(5174):956-959 (1994).
Kuehnle et al., "The therapeutic potential of stem cells from adults," BMJ. 325(7360):372-6 (2002).
Li et al., "Use of Donor beta2-Microglobulin-Deficient Transgenic Mouse Liver Cells for Isografts, Allografts, and Xenografts," *Transplantation*. 55(4):940-6 (1993).
Dieguez-Acuna et al., "Proteomics identifies multipotent and low oncogenic risk stem cells of the spleen," Int J Biochem Cell Biol. 42(10):1651-60 (2010) (10 pages).
Benkler et al., "Parkinson's disease, autoimmunity, and olfaction," Int J Neurosci. 119(12):2133-43 (2009) (Abstract only) (1 page).
Cebrián et al., "MHC-I expression renders catecholaminergic neurons susceptible to T-cell-mediated degeneration," Nat Commun. 5:3633 (2014) (Abstract only) (1 page).
D'Andrea, "Add Alzheimer's disease to the list of autoimmune diseases," Med Hypotheses. 64(3):458-63 (2005) (Abstract only) (2 pages).
International Preliminary Report on Patentability for International Application No. PCT/US2014/015101, dated Aug. 20, 2015 (9 pages).
Technical Data Sheet for Purified Rat Anti-Human CD120b, BD Pharmingen™ (2011) (2 pages).
Extended European Search Report for European Application No. 14748807.6, dated Jul. 15, 2016 (10 pages).
Communication pursuant to Rules 70(2) and 70a(2) EPC for European Application No. 14748807.6, dated Aug. 2, 2016 (1 pages).
Chopra et al., "Exogenous TNFR2 activation protects from acute GvHD via host T reg cell expansion", J Exp Med 213(9):1881-1900 (2016) (21 pages).
Christen et al., "A dual role for TNF-alpha in type 1 diabetes: islet-specific expression abrogates the ongoing autoimmune process when induced late but not early during pathogenesis," J Immunol. 166(12):7023-32 (2001).
Communication pursuant to Article 94(3) EPC for European Patent Application No. 14189654.8, dated Oct. 19, 2016 (5 pages).
Product Data Sheet for TNF RII/TNFRSF1B Inhibition of TNP-alpha-induced Cyototoxicity and Neutralization by Human TNF RII/TNFRSF1B Antibody. Retrieved Aug. 1, 2017. R&D Systems Inc. (3 pages).
Pillay et al., "Antibodies in oncology," N Biotechnol. 28(5):518-529 (2011).
International Search Report and Written Opinion for International Application No. PCT/US17/32513, dated Oct. 25, 2017 (17 pages).
Kretschmer et al., "Strong antigenic selection shaping the immunoglobulin heavy chain repertoire of B-1a lymphocytes in lambda 2(315) transgenic mice," Eur J Immunol. 32(8):2317-27 (2002).
Sedger et al., "Poxvirus tumor necrosis factor receptor (TNFR)-like T2 proteins contain a conserved preligand assembly domain that inhibits cellular TNFR1-induced cell death," J Virol. 80(18):9300-9 (2006).

(56) References Cited

OTHER PUBLICATIONS

Wagner, "Making and using antibodies," <http://www-users.med.cornell.edu/~jawagne/Antibody_Approaches.html>, accessed Aug. 8, 2016 (7 pages).

Diaw et al., "Structural and affinity studies of IgM polyreactive natural autoantibodies," J Immunol. 158(2):968-76 (1997).

Trad et al., "Clonal Progression during the T Cell-Dependent B Cell Antibody Response Depends on the Immunoglobulin DH Gene Segment Repertoire," Front Immunol. 5(385):1-11 (2014).

International Search Report and Written Opinion for International Application No. PCT/US16/32547, dated Aug. 31, 2016 (24 pages).

Yu et al., "Complex Interplay between Epitope Specificity and Isotype Dictates the Biological Activity of Antihuman CD40 Antibodies," Cancer Cell. 33:1-12 (2018) (17 pages).

International Preliminary Report on Patentability for International Application No. PCT/US2016/032547, dated Nov. 21, 2017 (16 pages).

Chen et al., "The phenotypic and functional consequences of tumour necrosis factor receptor type 2 expression on CD4(+) FoxP3(+) regulatory T cells," Immunology. 133(4):426-33 (2011).

Ji et al., "Cutting Edge: The Natural Ligand for Glucocorticoid-Induced TNF Receptor-Related Protein Abrogates Regulatory T Cell Suppression," J Immunol. 172(10):5823-7 (2004).

Torrey et al., "Targeting TNFR2 With Antagonistic Antibodies Inhibits Proliferation of Ovarian Cancer Cells and Tumor-Associated Tregs," Sci Signal. 10(462):eaaf8608 (2017) (13 pages).

Okubo et al., "Homogeneous Expansion of Human T-regulatory Cells via Tumor Necrosis Factor Receptor 2," Sci Rep. 3:3153 (11 pages).

Faustman et al., "TNF Receptor 2 and Disease: Autoimmunity and Regenerative Medicine," Front Immunol. 4:478 (2013) (8 pages).

Ban et al., "Strategic Internal Covalent Cross-Linking of TNF Produces a Stable TNF Trimer With Improved TNFR2 Signaling," Mol Cell Ther. 3:7 (2015) (6 pages).

\* cited by examiner

SEQUENCE LISTING

```
<160> NUMBER OF SEQ ID NOS: 1

<210> SEQ ID NO 1
<211> LENGTH: 268
<212> TYPE: PRT
<213> ORGANISM: Homo sapiens

<400> SEQUENCE: 1

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Pro Arg Cys Ser Pro Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125
```

-continued

```
Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Ala Ser Leu Ala Cys Arg
            260                 265
```

METHODS FOR EXPANSION OR DEPLETION OF T-REGULATORY CELLS

BACKGROUND OF THE INVENTION

T-regulatory cells (Tregs) are a small subset of T-lymphocytes with diverse clinical applications in transplantation, allergy, asthma, infectious diseases, graft versus host disease (GVHD), and autoimmunity. Tregs are also involved in immunotolerance in conditions such as cancer. The use of Tregs in clinical applications has been challenging because of their rarity in blood and the difficulty of expanding them ex vivo into homogeneous populations. Naturally occurring Tregs constitute only 1-5% of total CD4+ T cells in blood and they remain largely dormant until activated. Therefore, the harvesting of sufficient quantities of Tregs in order to investigate their role in basic biology and for clinical medical applications relies on the ability to expand Tregs ex vivo. More than a dozen protocols have been developed worldwide to expand Tregs ex vivo for reinfusion into patients, but all of these protocols produce heterogeneous progeny consisting of phenotypically and functionally mixed populations of CD4+ T cells. Heterogeneous CD4+ T cell populations hold risk because they are capable of releasing pro-inflammatory cytokines and they possess cells with diverse, sometimes antagonistic functions.

Heterogeneous populations of CD4+ T cells are deemed by regulatory agencies to be impure and irreproducible, so no clinical trials have proceeded beyond Phase I studies. Thus, a key research and clinical goal has been to find methods to selectively expand Tregs without stimulating expansion of other CD4+ T cell populations. A parallel goal in this field has been to find methods to selectively deplete Tregs and to expand lymphocyte populations. Such lymphocyte populations would be useful to upregulate the immune response in therapies for proliferative disorders, such as cancers.

SUMMARY OF THE INVENTION

The invention features a composition enriched in CD4+ CD25$^{hi}$ T regulatory cells (Tregs) in which at least 60% (e.g., 70%, 80%, 90%, or 100%) of the cells in the composition are Tregs. Preferably, the composition includes a homogeneous population of Tregs with desirable immune modulating properties, e.g., expression of forkhead box P3 (FOXP3) protein. The composition also includes at least $5 \times 10^6$ (e.g., $5 \times 10^7$, $5 \times 10^8$, $5 \times 10^9$, $5 \times 10^{10}$, $5 \times 10^{11}$, or $5 \times 10^{12}$) Tregs. The Tregs in the composition can be characterized as positive for the expression of one or more proteins selected from the group consisting of CTLA4, TNFR2, FOXP3, CD62L, Fas, HLA-DR, and CD45RO, and as low or negative for the expression of one or more proteins selected from the group consisting of CD127, CCR5, CCR6, CCR7, CXCR3, IFN-gamma, IL10, and ICOS.

The invention also features a method for producing a composition enriched in CD4+CD25$^{hi}$ Tregs, such as the composition described above. This method generally includes contacting in vitro a population of human cells that include T lymphocytes (e.g., CD4+ cells, CD25+ cells, or CD4+CD25+ cells) with a tumor necrosis factor receptor 2 (TNFR2) agonist and/or an NF-κB activator (e.g., during one or more culturing steps), thereby producing a composition that is enriched in the CD4+CD25$^{hi}$ Tregs. The population of human cells can be obtained from a human blood sample or a human bone marrow sample from a patient. The population of human cells from the sample are, or can include, CD4+ cells, CD25+ cells, or CD4+CD25+ cells, which can be isolated or enriched from the blood or bone marrow sample prior to contacting with the TNFR2 agonist and/or the NF-κB activator. The TNFR2 agonist and/or the NF-κB activator promote enrichment of the CD4+CD25$^{hi}$ Tregs, according to the method, by promoting an increase in the proliferation of CD4+CD25$^{hi}$ Tregs present in the population of human cells and/or by increasing the development of CD4+CD25$^{hi}$ Tregs from T lymphocytes (e.g., CD4+ cells, CD25+ cells, or CD4+CD25+ cells) present in the population of human cells (e.g., by differentiation or activation). The method described above preferably produces a homogenous population of Tregs, e.g., where at least 60% (e.g., 70%, 80%, 90%, or substantially 100%) of the cells in the composition are Tregs.

The TNFR2 agonist that can be used in the methods of the invention can be an agent selected from the group consisting of an antibody (e.g., a monoclonal anti-TNFR2 antibody), a peptide, a small molecule, and a protein. Because TNFR2 signaling can proceed via the downstream NF-κB pathway, an NF-κB activator can be used to contact the population of human cells in order to produce the composition enriched in Tregs. The NF-κB activator can be selected from the group consisting of a small molecule (e.g., betulinic acid, topoisomerase poison VP16, and doxorubicin), a peptide, a protein, a virus, and a small non-coding RNA.

In addition to a TNFR2 agonist and/or a NF-κB activator, the method of producing a composition enriched in Tregs can include contacting the population of human cells (e.g., CD4+ cells, CD25+ cells, or CD4+CD25+ cells) with one or more of interleukin-2 (IL2), rapamycin, anti-CD3 (e.g., an anti-CD3 antibody), and/or anti-CD28 (e.g., an anti-CD28 antibody). After in vitro proliferation, the above described methods of the invention can produce at least $5 \times 10^6$ (e.g., $5 \times 10^6$, $5 \times 10^7$, $5 \times 10^8$, $5 \times 10^9$, $5 \times 10^{10}$, $5 \times 10^{11}$, or $5 \times 10^{12}$) Tregs in which at least 60% (e.g., 70%, 80%, 90%, or substantially 100%) of the cells in the composition are Tregs.

The invention also features methods for treating an immunological disorder (e.g., an allergy, asthma, an autoimmune disorder, GVHD, or transplantation graft rejection) or an infectious disease (e.g., a bacterial infection, a viral infection, a fungal infection, and/or a parasitic infection) in a patient (e.g., a human patient) by administering to the patient any one or more of a composition enriched in Tregs, a TNFR2 agonist (e.g., a monoclonal anti-TNFR2 antibody), and a NF-κB activator. For example, the method of treatment can include administering the composition enriched in Tregs by itself or in combination with a NF-κB activator. The composition enriched in Tregs can be produced by any method known in the art. One method of producing a composition enriched in Tregs is by using the methods of the invention described above. The TNFR2 agonist and the NF-κB activator for use in the method of treating an immunological disorder can be any one or more of those described above.

Allergies that can be treated by the methods of the invention can be selected from the group consisting of food allergy, seasonal allergy, pet allergy, hives, hay fever, allergic conjunctivitis, poison ivy allergy oak allergy, mold allergy, drug allergy, dust allergy, cosmetic allergy, and chemical allergy. Autoimmune disorders that can be treated by the methods of the invention can be selected from the group consisting of type I diabetes, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, and Wegener's Granulomatosis.

The above described methods of treatment can include administering a composition enriched in Tregs that includes at least $5 \times 10^6$ (e.g., $5 \times 10^6$, $5 \times 10^7$, $5 \times 10^8$, $5 \times 10^9$, $5 \times 10^{10}$, $5 \times 10^{11}$, or $5 \times 10^{12}$) Tregs. Tregs having desirable immune-modulating properties include those expressing, e.g., FOXP3.

The invention also features an isolated antibody or antigen-binding fragment thereof that selectively binds to a first epitope of TNFR2, the first epitope includes positions 48-67 of SEQ ID NO: 1. The antibody or antigen-binding fragment thereof has an antagonistic effect on TNFR2 upon binding. The antibody or antigen-binding fragment thereof can further bind to a second epitope of TNFR2. The second epitope includes position 135 of SEQ ID NO: 1. The second epitope can include positions 135-147 of SEQ ID NO: 1 (e.g., positions 130-149 of SEQ ID NO: 1, positions 128-147 of SEQ ID NO: 1, or positions 135-153 of SEQ ID NO: 1). The antibody or antigen-binding fragment thereof can be a monoclonal antibody or antigen-binding fragment thereof, a polyclonal antibody or antigen-binding fragment thereof, an Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')$_2$) molecule, a domain antibody, a diabody, a triabody, an affibody, a domain antibody, a SMIP, a nanobody, a Fv fragment, a Fab fragment, a F(ab')$_2$ molecule, or a tandem scFv (taFv) fragment. The equilibrium dissociation constant ("$K_D$") for binding of the antibody or antigen-binding fragment thereof to TNFR2 can be less than about 50 nM (e.g., less than about 30 nM, less than about 20 nM, less than about 10 nM, less than about 5 nM, less than about 2 nM, less than about 1 nM, less than about 900 pM, less than about 800 pM, or less than about 700 pM). The equilibrium dissociation constant ("$K_D$") for binding of the antibody or antigen-binding fragment thereof to TNFR2 can be in the range of about 10 pM to about 50 nM (e.g., about 20 pM to about 30 nM, about 50 pM to about 20 nM, about 100 pM to about 5 nM, about 150 pM to about 1 nM, or about 200 pM to about 800 pM).

The invention also features a composition enriched in lymphocytes and depleted of Tregs, in which less than 10% (e.g., less than 9%, 8%, 7%, 5%, or 2% or substantially none) of the cells in the composition are Tregs. This composition can be produced by any method known in the art.

Furthermore, the invention also features methods for producing a composition enriched in lymphocytes and depleted of Tregs. This method generally includes contacting in vitro a population of human cells that include Tregs with a tumor necrosis factor receptor 2 (TNFR2) antagonist and/or an NF-κB inhibitor. The TNFR2 antagonist and/or the NF-κB inhibitor is used to suppress the proliferation of Tregs, thereby producing a composition that is substantially depleted of Tregs. The population of human cells can be obtained from a human blood sample or a human bone marrow sample from a patient. The population of human cells can include, e.g., CD4+ cells, CD25+ cells, or CD4+ CD25+ cells, which can be isolated or enriched from the blood or bone marrow sample prior to contacting with a TNFR2 antagonist and/or an NF-κB inhibitor. The method described above can be used to produce a composition enriched in lymphocytes (e.g., in which substantially 100% of the cells in the composition are lymphocytes) and in which less than 10% (e.g., less than 9%, 8%, 7%, 5%, or 2% or substantially none) of the cells in the composition are Tregs.

The TNFR2 antagonist that can be used in the above method for producing a composition enriched in lymphocytes and depleted of Tregs can be an agent that is selected from the group consisting of an antibody (e.g., a monoclonal anti-TNFR2 antibody), a peptide, a small molecule, and a protein. The NF-κB inhibitor that can be used in the above method can be an agent selected from the group consisting of a small molecule, a peptide (e.g., a cell penetrating inhibitory peptide), a protein, a virus, and a small non-coding RNA. For example, the NF-κB inhibitor can be a small molecule selected from the group consisting of 2-(1, 8-naphthyridin-2-yl)-Phenol, 5-Aminosalicylic acid, BAY 11-7082, BAY 11-7085, CAPE (Caffeic Acid Phenethylester), Diethylmaleate, Ethyl 3,4-Dihydroxycinnamate, Helenalin, Gliotoxin, NF-κB Activation Inhibitor II JSH-23, NFκB Activation Inhibitor III, Glucocorticoid Receptor Modulator, CpdA, PPM-18, Pyrrolidinedithiocarbamic acid ammonium salt, (R)-MG-132, Rocaglamide, Sodium Salicylate, QNZ, MG-132 [Z-Leu-Leu-Leu-CHO], Astaxanthin, (E)-2-Fluoro-4'-methoxystilbene, CHS-828, disulfiram, olmesartan, triptolide, withaferin, celastrol, tanshinone IIA, Ro 106-9920, cardamonin, BAY 11-7821, PSI, HU 211, ML130, PR 39, honokiol, CDI 2858522, andrographolide, and dithiocarbamates.

The TNFR2 antagonist can be a TNFR2 antagonist antibody that binds to a first epitope of TNFR2. The first epitope includes the positions 48-67 of SEQ ID NO: 1. The antibody or antigen-binding fragment thereof can bind to a second epitope of TNFR2. The second epitope includes the position 135 of SEQ ID NO: 1 (e.g., positions 135-147 of SEQ ID NO: 1). The antibody or antigen-binding fragment thereof can be a monoclonal antibody or antigen-binding fragment thereof, a polyclonal antibody or antigen-binding fragment thereof, an Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')$_2$) molecule, a domain antibody, a diabody, a triabody, an affibody, a domain antibody, a SM IP, a nanobody, a Fv fragment, a Fab fragment, a F(ab')$_2$ molecule, or a tandem scFv (taFv) fragment. The equilibrium dissociation constant ("$K_D$") for binding of the antibody or antigen-binding fragment thereof to TNFR2 can be less than about 50 nM (e.g., less than about 30 nM, less than about 20 nM, less than about 10 nM, less than about 5 nM, less than about 2 nM, less than about 1 nM, less than about 900 pM, less than about 800 pM, or less than about 700 pM). The equilibrium dissociation constant ("$K_D$") for binding of the antibody or antigen-binding fragment thereof to TNFR2 can be in the range of about 10 pM to about 50 nM (e.g., about 20 pM to about 30 nM, about 50 pM to about 20 nM, about 100 pM to about 5 nM, about 150 pM to about 1 nM, or about 200 pM to about 800 pM).

The invention features a method of treating a proliferative disorder (e.g., a cancer or a solid tumor) in a patient (e.g., a human patient) by administering to the patient any one or more of a composition enriched in lymphocytes and depleted of Tregs, a TNFR2 antagonist (e.g., a monoclonal anti-TNFR2 antibody), or an NF-κB inhibitor. For example, the method of treating proliferative disorders can include administering the composition enriched in lymphocytes (and depleted of Tregs) by itself or in combination with a NF-κB inhibitor. The composition enriched in lymphocytes can be produced by any method known in the art. Preferably, the composition enriched in lymphocytes can be produced by the methods of the invention as described above. The TNFR2 antagonist and the NF-κB inhibitor for use in the method of treating a proliferative disorder can be any one or more of those described above.

The invention features a method of treating an infectious disease (e.g., a bacterial infection, a viral infection, a fungal infection, or a parasitic infection) in a patient by administering to the patient the composition enriched in lymphocytes and depleted of Tregs, a TNFR2 antagonist (e.g., a monoclonal anti-TNFR2 antibody), or an NF-κB inhibitor. For example, the method of treating an infectious disease can include administering the composition enriched in lymphocytes (and depleted of Tregs) by itself or in combination with a NF-κB inhibitor. The composition enriched in lymphocytes can be produced by any method known in the art. Preferably, the composition enriched in lymphocytes can be produced by the methods of the invention as described above. The TNFR2 antagonist and the NF-κB inhibitor for use in the method of treating a proliferative disorder can be any one or more of those described above.

The invention features a method of treating an infectious disease in a patient by administering to the patient an effective amount of the antibody or antigen-binding fragment thereof as described herein. The invention also features a method of treating a proliferative disease (e.g., a cancer) in a patient by administering to the patient an effective amount of the antibody or antigen-binding fragment thereof as described herein.

Cancers that can be treated according to the methods of the invention (e.g., by administering any one or more of a composition enriched in lymphocytes (and depleted of Tregs), a TNFR2 antagonist and/or an NF-κB inhibitor) can be selected from the group consisting of Acute Lymphoblastic Leukemia, Acute Lymphoblastic Leukemia, Acute Myeloid Leukemia, Adrenocortical Carcinoma; AIDS-Related Lymphoma, AIDS-Related Malignancies, Anal Cancer, Astrocytoma, Bile Duct Cancer, Bladder Cancer; Bone Cancer, Osteosarcoma/Malignant Fibrous Histiocytoma, Brain Stem Glioma, Visual Pathway and Hypothalamic Glioma, Breast Cancer, Bronchial Adenomas/Carcinoids, Chronic Lymphocytic Leukemia, Chronic Myelogenous Leukemia, Chronic Myeloproliferative Disorders, Clear Cell Sarcoma of Tendon Sheaths, Colon Cancer, Colorectal Cancer, Cutaneous T-Cell Lymphoma, Endometrial Cancer, Epithelial Cancer, Esophageal Cancer, Ewing's Family of Tumors, Extracranial Germ Cell Tumor, Extragonadal Germ Cell Tumor, Extrahepatic Bile Duct Cancer, Eye Cancer, Intraocular Melanoma, Retinoblastoma, Gallbladder Cancer, Gastric (Stomach) Cancer, Hairy Cell Leukemia, Head and Neck Cancer, Hepatocellular (Liver) Cancer, Hodgkin's Lymphoma, Hypopharyngeal Cancer, Kaposi's Sarcoma, Kidney Cancer, Laryngeal Cancer, Pituitary Cancer, Plasma Cell Neoplasm/Multiple Myeloma, Pleuropulmonary Blastoma, Skin Cancer, Small Cell Lung Cancer, Small Intestine Cancer, Soft Tissue Sarcoma, Squamous Neck Cancer, Testicular Cancer, Thyroid Cancer, Urethral Cancer, Uterine Sarcoma, and Vaginal Cancer. The solid tumors that can be treated with the methods of the invention can include solid tumors of the brain, lung, breast, lymphoid, gastrointestinal tract, genitourinary tract, pharynx, prostate, or ovary.

Definitions

The term "about" is used herein to mean a value that is ±10% of the recited value.

The term "antibody," as used herein, includes whole antibodies or immunoglobulins and any antigen-binding fragment or single chains thereof. Antibodies, as used herein, can be mammalian (e.g., human or mouse), humanized, chimeric, recombinant, synthetically produced, or naturally isolated. In most mammals, including humans, whole antibodies have at least two heavy (H) chains and two light (L) chains connected by disulfide bonds. Each heavy chain consists of a heavy chain variable region (abbreviated herein as $V_H$) and a heavy chain constant region. The heavy chain constant region consists of three domains, $C_H1$, $C_H2$, and $C_H3$ and a hinge region between $C_H1$ and $C_H2$. Each light chain consists of a light chain variable region (abbreviated herein as $V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Antibodies of the present invention include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

The term "antigen-binding fragment," as used herein, refers to one or more fragments of an antibody that retain the ability to specifically bind to a specific antigen (e.g., CD21 receptor). The antigen-binding function of an antibody can be performed by fragments of a full-length antibody. The antibody fragments can be a Fab, Fab'2, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., *Nature* 341:544-546, 1989), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., *Science* 242: 423-426, 1988, and Huston et al., *Proc. Natl. Acad. Sci. USA* 85: 5879-5883, 1988). These antibody fragments are obtained using conventional techniques known to those of skill in the art, and the fragments are screened for utility in the same manner as intact antibodies. Antigen-binding fragments can be produced by recombinant DNA techniques or by enzymatic or chemical cleavage of intact immunoglobulins.

The term "chimeric antibody" refers to an immunoglobulin or antibody whose variable regions derive from a first species and whose constant regions derive from a second species. Chimeric antibodies can be constructed, for example, by genetic engineering, from immunoglobulin gene segments belonging to different species (e.g., from a mouse and a human).

The term "human antibody," as used herein, is intended to include antibodies, or fragments thereof, having variable regions in which both the framework and CDR regions are derived from human germline immunoglobulin sequences as described, for example, by Kabat et al (*Sequences of proteins of Immunological Interest, Fifth Edition*, U.S. Department of Health and Human Services, NIH Publication No. 91-3242, 1991). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences (i.e., a humanized antibody or antibody fragment).

The term "humanized antibody" refers to any antibody or antibody fragment that includes at least one immunoglobulin domain having a variable region that includes a variable framework region substantially derived from a human immunoglobulin or antibody and complementarity determining regions (e.g., at least one CDR) substantially derived from a non-human immunoglobulin or antibody.

The term "TNF-α mutein," as used herein, refers to a polypeptide having an amino acid sequence that differs from the amino acid sequence of TNF-α by one or more amino acids, while retaining the ability to activate or inhibit TNFR2. For example, a TNF-α mutein may have an amino acid sequence with greater than 90% but less than 100% sequence identity relative to the amino acid sequence of a reference polypeptide (TNF-α).

The term "substantially 100%" or "substantially homogeneous" as used herein with respect to a Treg enriched composition of the invention means at least 90%, 95%, 96%, 97%, 98%, or 99% or more (e.g., all) of the cells in the composition are Tregs.

The term "treating" as used herein means stabilizing or reducing an adverse symptom associated with a condition; reducing the severity of a disease symptom; slowing the rate of the progression of a disease; inhibiting or stabilizing the progression of a disease condition; or changing a metric that is associated with the disease state in a desirable way.

DETAILED DESCRIPTION OF THE INVENTION

Figure 1A:
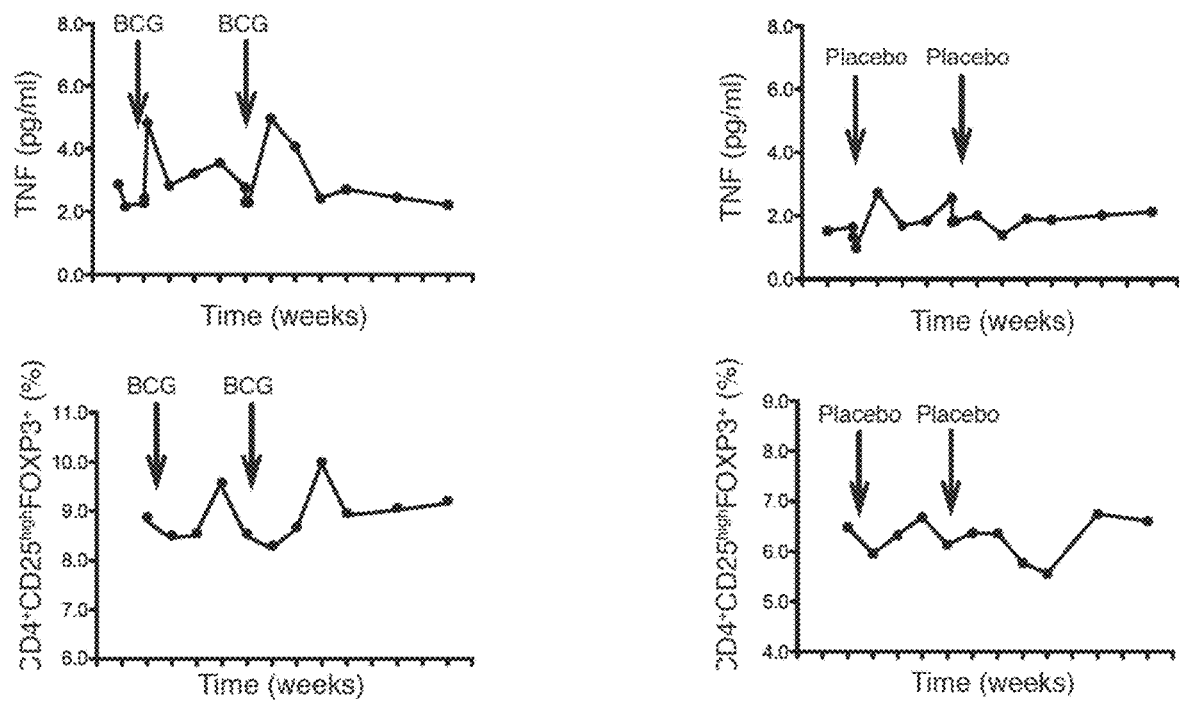
FIG. 1A is a set of graphs showing that in a small double-blinded, placebo-controlled trial of human subjects, BCG treatment induces TNF-α (top left graph) and shortly thereafter Tregs appear in the treated subject (bottom left graph) versus placebo (right hand side graphs).

The invention features methods for the production of a composition enriched in Tregs (e.g., CD4+,CD25$^{hi}$ Tregs). The invention also features methods for treating immunological disorders and infectious diseases using a composition enriched in Tregs, e.g., a composition enriched in Tregs prepared by the methods described below. The invention also features methods for producing a composition enriched in lymphocytes (and depleted of Tregs) and methods of treating proliferative disorders using this composition.

Tregs and TNFR2

T regulatory cells (Tregs) are a small subset of T-lymphocytes with diverse clinical applications in transplantation, allergy, asthma, infectious diseases, GVHD, and autoimmunity. The Tregs can be used to suppress the abnormal immune response in patients in need thereof. Tregs are also known to be involved in immunotolerance in conditions such as cancer. Naturally occurring Tregs constitute only 1-5% of total CD4+ T cells in blood, and remain largely dormant until activated. In humans, Tregs are defined by co-expression of CD4+ and high expression of the interleukin-2 (IL-2) receptor alpha chain CD25$^{hi}$. Tregs also feature inducible levels of intracellular transcription factor FOXP3 and the expression of FOXP3 can be used to identify Tregs. TNF-α has two receptors, TNFR1 and TNFR2, each of which controls different signaling pathways. Unlike TNFR1, which has ubiquitous cellular expression, TNFR2 is expressed in a more limited manner, restricted primarily to subpopulations of T cells (in particular, Tregs), endothelial cells, and neurons. Research in primates suggests that TNFR2-specific ligands are likely to have minimal systemic toxicity because of the restricted cellular distribution of TNFR2. Naturally occurring Tregs appear to express TNFR2 at a higher density than TNFR1. These features make TNFR2 an advantageous molecular target on Tregs.

Methods for Producing an Enriched Treg Composition

The invention features methods for expanding Tregs in a sample isolated from a patient (e.g., a human), such as a peripheral blood sample or a bone marrow sample, to produce a composition enriched in Tregs that are characterized as CD4+ and CD25$^{hi}$. Methods for promoting the proliferation of Tregs are known in the art, e.g., as described in Brunstein, C. G. et al., Infusion of ex vivo expanded T regulatory cells in adults transplanted with umbilical cord blood: safety profile and detection kinetics, *Blood* 117, 1061-1070 (2011); Saas, P. & Perruche, S., (F1000 Immunology, 2012), Tresoldi, E. et al., Stability of human rapamycin-expanded CD4+CD25+ T regulatory cells, *Haematologica* 96, 1357-1365 (2011); Nadig, S. N. et al., In vivo prevention of transplant arteriosclerosis by ex vivo-expanded human regulatory T cells. *Nat Med* 16, 809-813 (2010); Battaglia, M., Stabilini, A. & Tresoldi, E., Expanding human T regulatory cells with the mTOR-inhibitor rapamycin, *Methods Mol Biol* 821, 279-293 (2012); Pahwa, R. et al., Isolation and expansion of human natural T regulatory cells for cellular therapy, *Journal of immunological methods* 363, 67-79 (2010); Hoffmann, P., Eder, R., Kunz-Schughart, L. A., Andreesen, R. & Edinger, M. , Large-scale in vitro expansion of polyclonal human CD4(+) CD25high regulatory T cells, *Blood* 104, 895-903 (2004); Lin, C. H. & Hunig, T., Efficient expansion of regulatory T cells in vitro and in vivo with a CD28 superagonist, *European journal of immunology* 33, 626-638 (2003); Lan, Q. et al., Induced FOXP3(+) regulatory T cells: a potential new weapon to treat autoimmune and inflammatory diseases? *Journal of molecular cell biology* 4, 22-28 (2012); Sagoo, P. et al., Human regulatory T cells with alloantigen specificity are more potent inhibitors of alloimmune skin graft damage than polyclonal regulatory T cells, *Science Translational Medicine* 83, 1-10 (2011); Edinger, M. & Hoffmann, P., Regulatory T cells in stem cell transplantation: strategies and first clinical experiences, *Current opinion in immunology* 23, 679-684 (2011); Trzonkowski, P. et al., First-in-man clinical results of the treatment of patients with graft versus host disease with human ex vivo expanded CD4+CD25+ CD127-T regulatory cells, *Clinical Immunology* 133, 22-26 (2009); Di Ianni, M. et al., Tregs prevent GVHD and promote immune reconstitution in HLA-haploidentical transplantation, *Blood* 117, 3921-3928 (2011); Hippen, K. L. et al, Massive ex vivo expansion of human natural regulatory T cells (T(regs)) with minimal loss of in vivo functional activity. *Sci Transl Med* 3, 83ra41 (2011); Kim, Y. C. et al., Oligodeoxynucleotides stabilize Helios-expressing Foxp3+ human T regulatory cells during in vitro expansion, *Blood* 119, 2810-2818 (2012); Bacchetta, R. et al., Interleukin-10 Anergized Donor T Cell Infusion Improves Immune Reconstitution without Severe Graft-Versus-Host-Disease After Haploidentical Hematopoietic Stem Cell Transplantation. *ASH Annual Meeting Abstracts* 114, 45-(2009); Desreumaux, P. et al., Safety and efficacy of antigen-specific regulatory T-cell therapy for patients with refractory Crohn's disease, *Gastroenterology* 143, 1207-1217 e1202 (2012); Clerget-Chossat, N. et al., in International Society for Cell Therapy Seattle, Wash., (2012); and Cardenas, P. A., Huang, Y. & Ildstad, S. T., The role of pDC, recipient T(reg) and donor T(reg) in HSC engraftment: Mechanisms of facilitation, *Chimerism* 2, 65-70 (2011). Each of these publications, and their methods for expanding Tregs, is incorporated herein by reference.

The protocols for promoting the proliferation of Tregs that are described in the above publications generally include obtaining fresh sample (e.g., a blood sample) from a patient (e.g., a human patient) that includes a population of CD4+ cells. The CD4+ cells can be further purified or enriched in one or more steps prior to the expansion of Tregs. The CD4+ cells can be separated from the sample using techniques known in the art (e.g., using magnetic beads conjugated to anti-CD4+ antibodies such as Dynabeads® CD4 Positive Isolation kit (Invitrogen)). During culturing, the CD4+ cells can be contacted with one or more reagents to stimulate their proliferation. For example, one or more of anti-CD3 antibody, anti-CD28 antibody, human IL-2, and rapamycin can be added. However, this method alone produces a heterogeneous population of cells, some of which are capable of releasing pro-inflammatory cytokines that can be detrimental to the patient. This heterogeneous population is not useful for treatment of immunological disorders or infectious diseases and Tregs cannot be easily isolated from this heterogeneous population without damaging them. The present invention improves upon these protocols by using a TNFR2 agonist that preferentially promotes proliferation of Tregs and produces a homogeneous population of Tregs with desirable traits, e.g., a sub-population of Tregs that express FOXP3. The TNFR2 agonist and/or the NF-κB activator promote enrichment of the CD4+CD25$^{hi}$ Tregs, according to the method, by promoting an increase in the proliferation of CD4+CD25$^{hi}$ Tregs present in the population of human cells and/or by increasing the development of CD4+CD25$^{hi}$ Tregs from T lymphocytes (e.g., CD4+ cells, CD25+ cells, or CD4+CD25+ cells) present in the population of human cells (e.g., by differentiation or activation). The invention produces a population of cells enriched in Tregs that can be used for treatment of immunological disorders or infectious diseases as described herein.

In vitro Expansion of Tregs Using a TNFR2 Agonist

In general, the present method includes obtaining a starting population of T lymphocytes (e.g., CD4+ cells, CD25+ cells, or CD4+CD25+ cells) from a human sample, e.g., blood or bone marrow sample. When blood sample is used, typically 3-4 tubes of blood (~2-10 mL in each tube) can be used in the protocol described below. One skilled in the art can adjust the amount of the blood sample that is used depending on the scale of the cell-culture protocol.

In general, anti-CD4 and/or anti-CD25 antibodies attached to a bead matrix, e.g., a magnetic bead (such as Dynabeads®), can be used for isolating the CD4+ cells, CD25+ cells, or CD4+CD25+ cells. For example, the CD4+ T cells can be isolated by using commercially available reagents, e.g., Dynabeads® CD4 Positive Isolation kit, and the CD25+ cells can be isolated using commercially available reagents, e.g., Dynabeads CD25 and/or DETACHa-BEAD CD4/CD8 (Invitrogen). When CD4+CD25+ cells are used as the starting population, the cells can be isolated using both anti-CD4 and anti-CD25 beads in a single step or in a two step method by isolating the CD4+ cells first followed by isolation of the CD25+ cells, or vice versa.

The isolated CD4+ cells, CD25+ cells, or CD4+CD25+ cells can then be expanded in cell culture for about 16 days (e.g., about 5, 6, 7, 8, 9, 10, 11, 12, 13, 14, 15, 16, 17, or 18 or more days) in a suitable cell culture vessel, e.g., a 96 well round-bottom plate ($2\times10^4$ cells/well), in the presence of one or more of anti-CD3 and/or anti-CD28 antibodies. The amount of cells to be used in the starting culture will depend on the volume of the cell culture vessel. The anti-CD3 and anti-CD28 antibodies can be present throughout the course of cell culture, e.g., for each days of culture or only during a portion of the cell culture (one or several days during culturing). Typically the anti-CD3 and anti-CD28 antibodies can be added in the form of commercially available Dynabead Human Treg Expander (Invitrogen) at a bead to cell ratio of 2:1.

Human IL-2 and/or rapamycin can also be added to the cell culture media, e.g., one or more times during the course of cell culture. For example, human IL-2 can be added every two days, e.g., at day 2, 4, 7, 9, 11, and 14 of a 16 day cell culture period. Rapamycin can be added at day 0, 2, 4, and 7 of a 16 day-cell culture period. Human IL-2 and rapamycin can be added together or on alternating days. Typically, human IL-2 is added two days after the start of cell culture. Human IL-2 and/or rapamycin can also remain in the cell culture for the entire period of the expansion protocol. The cell culture media can be changed every 2-3 days by changing half of the media with fresh media; the fresh media may also contain human IL-2 and/or rapamycin. For example, half of the media can be changed every 2-3 days containing rapamycin (until day 7) and IL-2. Typically rapamycin can be used at a concentration of 0.5 nM to 100 µM (e.g., 0.5 nM, 1 nM, 10 nM, 50 nM, 100 nM, 200 nM, 0.5 µM, 0.75 µM, 1 µM, 1.2 µM, or 2 µM). and human IL-2 can be used at a concentration of 0.05 to 6,000 U/ml (e.g., 0.05 U/ml, 1 U/ml, 2 U/ml, 10 U/ml, 20 U/ml, 50 U/ml, 100 U/ml, 150 U/ml, 200 U/ml, 250 U/ml, or 300 U/ml). During the course of the cell culture, as described above, the cells can be passaged as necessary. Protocols for passaging of cells are known in the art.

A TNFR2 agonist can be added at the start of culture at day 0 or at later time points after initiation of the culture (e.g., on any one of the days after initiation of culturing, so long as at least one or more days (e.g., at least 2, 3, 4, 5, 6, 7, 8, 9, 10, 11, 12, 13, 14, 15, or 16, or more days) of culturing includes contacting the cells with a TNFR2 agonist). Additional TNFR2 agonist can be added at several points during the course of cell culture, e.g., at one or more of days 7, 8, 9, 10, 11, or 12. Typically a TNFR2 agonist is added on day 0 and additional TNFR2 agonist can be added on day 9 of a 16 day-cell culture period (see, e.g., FIG. 3A). The TNFR2 agonist that can be typically used is an anti-TNFR2 monoclonal antibody. Additional TNFR2 agonists that can be used in this method are described below. In general, the anti-TNFR2 antibody can be used at a concentration in the range of 0.05 µg/ml to 500 µg/ml, or more if necessary (e.g., 0.05 µg/ml, 0.1 µg/ml, 0.25 µg/ml, 0.5 µg/ml, 1 µg/ml, 1.5 µg/ml, 2 µg/ml, 2.5 µg/ml, 3 µg/ml, 3.5 µg/ml, 4 µg/ml, 4.5 µg/ml, or 5 µg/ml, 10 µg/ml, 50 µg/ml, 100 µg/ml, 200 µg/ml, 300 µg/ml, 400 µg/ml, or 500 µg/ml). The anti-TNFR2 antibody can be attached to a matrix, e.g., a bead, such as a magnetic bead, for removal at the end of the cell culture period.

The cells can be harvested and the anti-CD3 and anti-CD28 regents can be removed, e.g., by removal of the Treg Expander beads by the Detach-a-bead reagent or by multiple rounds of proliferation that permits bead detachment. Cells can then be washed in an appropriate medium and rested. Cells can then be analyzed for expression of various protein markers, stored appropriately, and/or used in methods for treating various disorders as described below.

After in vitro proliferation, the Tregs in the enriched composition comprise at least 60% (e.g., 70%, 80%, 90%, or 100%) of the cells in the composition. The method described above preferably produces a homogenous population of Tregs, e.g., where substantially 100% (e.g., at least 90%, 95%, 96%, 97%, 98%, or 99% or more (e.g., all)) of the cells in the composition are Tregs.

The method described above can result in an approximately 2 fold (e.g., 1.5-fold, 2-fold, 2.5-fold, 3-fold, 3.5-fold, or 4-fold or more) expansion of Tregs. The Tregs produced by this expansion protocol are characterized as expressing FOXP3, e.g., preferably at least 80% (e.g., 85%, 90%, 95%, 98%, 99%, or substantially 100%) of the cells in the expanded population of Tregs express FOXP3. In addition, it is preferable that the Tregs expanded by the methods of the invention express high levels of FOXP3. The Treg population also includes a low percentage of cells expressing IFNγ. The Treg population also exhibits increased capacity for suppressing activation of CD8+ cells.

In previously described Treg expansion protocols, a disadvantage was that the identification of the expanded Tregs in a heterogeneous population of cells required post-expansion sorting, often multiple rounds of sorting, of the Tregs. These multi-sorting procedures severely and adversely affected the viability, function, and yield of the Tregs and therefore limited the subsequent use of the sorted cells in therapeutic applications. Furthermore, this sorting could only enrich for Tregs expressing cell surface markers and not for Tregs expressing FOXP3, which is an intracellular marker. The present invention features the proliferation of Tregs by contacting a population of human cells that is, or that includes, T lymphocytes (e.g., human CD4+ cells, CD25+ cells, or CD4+CD25+ cells) with a TNFR2 agonist to produce a substantially homogenous population of Tregs that express FOXP3, CD4+, and $CD25^{hi}$. The Tregs produced by the present method require no post-expansion sorting prior to use in therapeutic applications. This is a significant advantage over previously described Treg expansion protocols. The Tregs produced by the present invention are also more potent than previously described Treg cell populations, which may be a result of their homogeneity or the subset of Tregs produced by the present method, or both. The present enriched Treg populations exhibit highly desirable qualities similar to those of immune-modulating Tregs.

TNFR2 Agonists

The TNFR2 agonist that can be used in the methods of the invention include agents, such as an antibody, a peptide, a small molecule, and a protein. The TNFR2 agonist is an agent that can bind to TNFR2 and activate TNFR2 signaling. The TNFR2 agonist can be any agent that, when contacted with CD4+ T cells, can stimulate the expression of any one or more proteins selected from the group consisting of FOXP3, TNF, TRAF2, TRAF3, and cIAP2.

In particular, the TNFR2 agonist can be a monoclonal antibody that binds TNFR2, such as Clone MR2-1 (Cell Sciences) or Clone MAB2261 (R&D Systems, Inc.). The TNFR2 agonist can also be a TNF-α mutein that binds only to TNFR2 as an agonist. TNF-α muteins that can be used as TNFR2 agonists include those described in, e.g., U.S. Patent Application Publication No. 2008/0176796 A1; U.S. Pat. Nos. 5,486,463 and 5,422,104; PCT Publication Nos. WO 86/02381; WO 86/04606; and WO 88/06625; and European Patent Nos. 155,549; 168,214; 251,037; 340,333; and 486,908. Each of these publications is incorporated herein by reference.

In addition, anti-TNFR2 antibodies that are capable of acting as TNFR2 agonists are described in Galloway et al. (Eur. J. Immunol. 22:3045-3048, 1992), Tartaglia et al. (J. Biol. Chem. 268:18542-18548, 1993), Tartaglia et al. (J. Immunol. 151:4637-4641, 1993), Smith et al. (J. Biol. Chem. 269:9898-9905, 1994), and Amrani et al. (Am. J. Respir. Cell. Mol. Biol. 15:55-63, 1996); each of which is incorporated herein by reference.

Peptides that are capable of acting as a TNFR2 agonist can include an 11 amino acid TNF receptor agonist peptide ($TNF_{70-80}$) described in Laichalk et al. (Infection & Immunity 66:2822-2826, 1998), incorporated herein by reference.

Since activation of the NF-κB pathway is a downstream effect of TNFR2 agonism, the Treg expansion method can instead, or in addition, include contacting the T lymphocyte population (e.g., CD4+ cells, CD25+ cells, or CD4+CD25+ cells) with one or more activators of the NF-κB pathway in place of a TNFR2 agonist. The NF-κB activator can be a small molecule, a peptide, a protein, a virus, or a small non-coding RNA. For example, the NF-κB activator any one of the small molecules described in Manuvakhova et al., J. Neurosci. Res. 89: 58-72, 2011 (incorporated herein by reference). Alternatively, the NF-κB activator can be betulinic acid. The NF-κB activator can also be the topoisomerase poison VP16. Additionally the NF-κB activator can be doxorubicin.

Characterization of Tregs

The Tregs in the enriched composition produced by the above described methods are CD4+ and CD25$^{hi}$ and can be characterized by the presence or absence of one or more additional molecular markers. For example, the Tregs produced by the methods of the invention may express one or more proteins selected from the group consisting of FOXP3, CTLA4, TNFR2, CD62L, Fas, HLA-DR, and CD45RO and are considered to be "positive" for these markers. Alternatively, the Tregs may not express, or may express in low to near undetectable amounts, one or more proteins selected from the group consisting of CD127, CCR5, CCR6, CCR7, CXCR3, IFN-gamma, 11_10, and ICOS and may be considered to be considered "negative" for these markers. Preferably, the method produces a composition enriched in Tregs, in which at least 90% of Tregs express H LA-DR and less than 5% of Tregs express ICOS.

Treatment Using an Enriched Treg Composition of the Invention

The invention features methods for treating a variety of diseases, e.g., immunological disorders and conditions, such as allergies, asthma, autoimmune diseases, GVHD, transplantation graft rejection, and infectious diseases by administering a composition enriched in Tregs to a patient (e.g., a human) in need thereof. The composition enriched in Tregs can be produced by the methods described above, for example, by contacting a human sample, e.g., a blood or bone marrow sample, containing T lymphocytes (e.g., CD4+ cells, CD25+ cells, or CD4+CD25+ cells) with a TNFR2 agonist (e.g., a TNFR2 agonist antibody) and/or an NF-κB activator to produce the composition enriched in Tregs (e.g., a substantially homogenous population of Tregs). The TNFR2 agonist and/or the NF-κB activator promote enrichment of the CD4+CD25$^{hi}$ Tregs, according to the method, by promoting an increase in the proliferation of CD4+CD25$^{hi}$ Tregs present in the population of human cells and/or by increasing the development of CD4+CD25$^{hi}$ Tregs from T lymphocytes (e.g., CD4+ cells, CD25+ cells, or CD4+CD25+ cells) present in the population of human cells (e.g., by differentiation or activation).

A patient in need of treatment for an immunological disorder or condition, such as an allergy, asthma, an autoimmune disease, GVHD, or a transplantation graft rejection, or for an infectious disease can be administered an enriched composition of Tregs (e.g., CD4+CD25$^{hi}$ Tregs or CD4+CD25$^{hi}$FOXP3+ Tregs) produced from their own blood or bone marrow using the following steps: i) obtaining a cell sample, e.g., a blood or bone marrow sample, from the human patient; ii) isolating T lymphocytes (e.g., CD4+ cells, CD25+ cells, or CD4+CD25+ cells) from the sample as described in the method above; iii) subjecting these cells to the Tregs expansion method described above (e.g., contact and/or culturing of the CD4+ cells, CD25+ cells, or CD4+CD25+ cells with anti-CD3 antibody, anti-CD28 antibody, and a TNFR2 agonist in combination with IL-2 and/or rapamycin, and/or contact or culturing of the CD4+ cells, CD25+ cells, or CD4+CD25+ cells with an NF-κB activator) to produce a composition enriched in Tregs (e.g., a substantially homogenous population of Tregs in which the Tregs comprise, e.g., >90% of cells in the composition); and iv) introducing the composition enriched in Tregs into the patient without any (or with limited) post-expansion sorting of the enriched Tregs in order to treat the disease or disorder. The above steps of the method of treatment can be performed in iterative cycles, where the number of cycles of treatment provided to the patient can be determined by the disorder being treated, the severity of the disorder, and/or the outcome of each treatment cycle (i.e., a change in the disease state). For example, changes in efficacy markers and/or in clinical outcomes can be used for determining the frequency with which blood or bone marrow should be obtained from a patient, Tregs enriched from that blood or bone marrow, and/or the enriched Tregs administered to the patient. The enriched Treg composition can also be stored (e.g., frozen) for future administration.

Preferably, the Tregs are obtained from a patient's own blood or bone marrow (i.e., autologous cells), although the following methods of treatment may also include the use of allogeneic Tregs with possible best fit HLA matching or from unrelated donors that have been expanded according to the above methods. Allogeneic Tregs preferentially share at least 4/6 HLA markers in common with the patient receiving the enriched Treg composition.

Treatment of an Immunological Disorder or Condition Using an Enriched Treg Composition of the Invention The enriched Treg composition produced by the methods described above can be administered to a patient suffering from an immunological disorder or condition, such as an allergy, asthma, an autoimmune disorder, GVHD, or a transplantation graft rejection, to treat the immunological disorder or condition.

1) Allergies:

An enriched Treg composition of the invention can be used to treat one or more allergic conditions in a patient, such as an allergy selected from the group consisting of food allergy, seasonal allergy, pet allergy, hives, hay fever, allergic conjunctivitis, poison ivy allergy oak allergy, mold allergy, drug allergy, dust allergy, cosmetic allergy, and chemical allergy. Administration and dosage of the Treg composition are discussed herein below.

2) Asthma:

An enriched Treg composition of the invention can be used to treat asthma by administering the composition to a patient in need thereof.

3) Autoimmune Disorders:

An enriched Treg composition of the invention can be used to treat one or more autoimmune disorder selected from the group consisting of type I diabetes, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, and Wegener's Granulomatosis. Additional autoimmune diseases that can be treated with the methods of the invention are disclosed in U.S. Pat. No. 8,173,129, incorporated herein by reference. Administration and dosage of the Treg composition are discussed herein below.

4) Transplantation Graft Rejection or GVHD:

An enriched Treg composition of the invention can be used to reduce or inhibit transplantation graft rejection or GVHD that occurs when transplanted tissue is rejected by the recipients immune system. The transplantation graft rejection can be a chronic rejection, an acute rejection, or a hyperacute rejection. Administration and dosage of the Treg composition are discussed herein below.

In addition to the composition enriched in Tregs, other treatments that can be administered to the patient can include, e.g., steroid treatment, antibody-based treatment, immosuppressive drugs, blood transfer, and marrow transplant, according to techniques known in the art.

Treatment of an Infectious Disease Using an Enriched Treg Composition of the Invention The invention also features methods of treating infectious diseases caused any one or more of a virus, a bacteria, a fungus, or a parasite by administering a composition enriched in Tregs. The composition enriched in Tregs can be produced by the methods described above. The methods of the invention can be used for treating viral infections caused by, e.g., a member of the Flaviviridae family (e.g., a member of the *Flavivirus, Pestivirus,* and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus; a member of the Bunyaviridae family (e.g., a member of the *Hantavirus, Nairovirus, Orthobunyavirus,* and *Phlebovirus* genera), which includes the Hantaan virus, Sin Nombre virus, Dugbe virus, Bunyamwera virus, Rift Valley fever virus, La Crosse virus, California encephalitis virus, and Crimean-Congo hemorrhagic fever (CCHF) virus; a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxviridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively)).

The methods of the invention can also be used for treating bacterial infections. Examples of bacterial infections that may be treated include, but are not limited to, those caused by bacteria within the genera *Salmonella, Streptococcus, Bacillus, Listeria, Corynebacterium, Nocardia, Neisseria, Actinobacter, Moraxella, Enterobacteriacece, Pseudomonas, Escherichia, Klebsiella, Serratia, Enterobacter, Proteus, Salmonella, Shigella, Yersinia, Haemophilus, Bordatella, Legionella, Pasturella, Francisella, Brucella, Bartonella, Clostridium, Vibrio, Campylobacter,* and *Staphylococcus.*

The methods of the invention can also be used for treating parasitic infections caused by a protozoan parasite (e.g., an intestinal protozoa, a tissue protozoa, or a blood protozoa) or a helminthic parasite (e.g., a nematode, a helminth, an adenophorea, a secementea, a trematode, a fluke (blood flukes, liver flukes, intestinal flukes, and lung flukes), or a cestode). Exemplary protozoan parasites include *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis,* and *Histomonas meleagridis.* Exemplary helminthic parasites include *Richuris trichiura, Ascaris lumbricoides, Enterobius vermicularis, Ancylostoma duodenale,*

*Necator americanus, Strongyloides stercoralis, Wuchereria bancrofti*, and *Dracunculus medinensis, Schistosoma mansoni, Schistosoma haematobium, Schistosoma japonicum, Fasciola hepatica, Fasciola gigantica, Heterophyes heterophyes*, and *Paragonimus westermani, Taenia solium, Taenia saginata, Hymenolepis nana*, and *Echinococcus granulosus*.

The methods of the invention can also be used for treating fungal infections. Examples of fungal infections that may be treated include, but are not limited to, those caused by, e.g., *Aspergillus, Candida, Malassezia, Trichosporon, Fusarium, Acremonium, Rhizopus, Mucor, Pneumocystis*, and *Absidia*.

Administration and dosage of the Treg composition in methods for treating an infectious disease are discussed herein below.

Treatment Using an NF-κB Activator

Because TNFR2 signaling is transduced via activation of the NF-κB pathway, activators of NF-κB signaling can also be used in place of, or in combination with, administration of an enriched Treg composition for treating immunological disorders or conditions and infectious diseases according to the methods described above. For example, any one of the NF-κB activators described above can be used in the methods of treatment described above. The NF-κB activator can be used by itself or in combination with the composition enriched in Tregs.

Methods for Producing an Enriched Lymphocyte Composition Depleted of Tregs

The invention also features methods for producing a composition enriched in lymphocytes (and depleted of Tregs) in vitro. Preferably the method produces a composition in which less than 10% of the cells (e.g., less than 10%, 5%, 3%, 1%, or 0.5%, or none of the cells) in the composition are Tregs. The method is similar to the method for producing a composition enriched in Tregs except a TNFR2 antagonist, such as an anti-TNFR2 monoclonal antibody, is used in place of a TNFR2 agonist. Additional TNFR2 antagonists that can be used in this method are described below.

The method generally involves the separation of T lymphocytes (e.g., CD4+ cells, CD25+ cells, or CD4+CD25+ cells) from human samples, e.g., human blood or bone marrow sample, followed by expansion of the cells during culturing by incubation of the cells with anti-CD3 and anti-CD28 antibodies. During the expansion step, the cells are contacted with a TNFR2 antagonist. The TNFR2 antagonist suppresses the proliferation of Tregs in the culture, thereby producing a composition that is enriched in lymphocytes and depleted of Tregs. Human-IL-2 and/or rapamycin may optionally be added to the cell culture during the expansion of cells.

After in vitro enrichment of lymphocytes (and depletion of Tregs), less than 10% (e.g., less than 10%, 9%, 8%, 7%, 5%, or 2% or substantially none) of the cells in this composition are Tregs. The method described above can result in approximately 2 fold (e.g., 2.5-fold, 3-fold, 3.5-fold, or 4-fold or more) enrichment of non-Treg lymphocytes (e.g., CD4+ T cells, CD8+ T cells, CD4+ CD8+ T cells, B cells, natural killer cells, etc.). The enriched lymphocyte population may also include dendritic cells, monocytes, macrophages, and neutrophils.

TNFR2 Antagonists

The TNFR2 antagonist that can be used in this method of the invention can include agents, such as an antibody, a peptide, a small molecule, and a protein that can bind to TNFR2 and suppress TNFR2 signaling. The TNFR2 antagonist can be an agent that, when contacted with CD4+ T cells, can stimulate the expression of cIAP but not the expression of TRAF2, TRAF3, or FOXP3.

The TNFR2 antagonist can be a monoclonal antibody that binds TNFR2. There are two epitopes of TNFR2 that the TNFR2 antagonist antibody can bind. The first epitope includes positions 48-67 (QTAQMCCSKCSPGQHAK-VFC) of SEQ ID NO: 1 (amino acid sequence of human TNFR2). The second epitope includes position 135 (R) of SEQ ID NO: 1 (e.g., positions 135-153 (RLCAPLRKCR-PGF) of SEQ ID NO: 1). For example, the TNFR2 antagonist antibody can be any one of Clone MAB726 (R&D Systems, Inc.) or Clone M1 (BD Biosciences). While each MAB726 and M1 binds the second epitope, an antibody of the invention may bind the first epitope or both epitopes. The TNFR2 antagonist antibody or antigen-binding fragment thereof can bind TNFR2 with a $K_D$ of less than about 50 nM (e.g., less than about 30 nM, less than about 20 nM, less than about 10 nM, less than about 5 nM, less than about 2 nM, less than about 1 nM, less than about 900 pM, less than about 800 pM, or less than about 700 pM). The TNFR2 antagonist antibody or antigen-binding fragment thereof can bind TNFR2 with a $K_D$ in the range of about 10 pM to about 50 nM (e.g., about 20 pM to about 30 nM, about 50 pM to about 20 nM, about 100 pM to about 5 nM, about 150 pM to about 1 nM, or about 200 pM to about 800 pM). The TNFR2 antagonist antibody avidity can be determined using methods known in the art (e.g., surface plasmon resonance. For example, MAB 726 binds TNFR2 with a $K_D$ of 621 pM (determined by surface plasmon resonance (Pioneer SensiQ®, Oklahoma City, Okla.)). The TNFR2 antagonist can also be a TNF-α mutein that is capable of binding to TNFR2 and suppressing downstream signaling.

The TNFR2 antagonist can function via downstream signaling by inhibition of the NF-κB pathway. Thus, the method of the invention can also include contacting the human sample e.g., a blood or bone marrow sample, with one or more inhibitors of the NF-κB pathway in order to achieve the same effect as that of using a TNFR2 antagonist. The NF-κB inhibitor can be a small molecule, a peptide, a protein, a virus, or a small non-coding RNA. In one embodiment, the NF-κB inhibitor that can be used in the methods to produce a composition enriched in lymphocytes can be any one of 2-(1,8-naphthyridin-2-yl)-Phenol, 5-Aminosalicylic acid, BAY 11-7082, BAY 11-7085, CAPE (Caffeic Acid Phenethylester), Diethylmaleate, Ethyl 3,4-Dihydroxycinnamate, Helenalin, Gliotoxin, NF-κB Activation Inhibitor II JSH-23, NFκB Activation Inhibitor III, Glucocorticoid Receptor Modulator, CpdA, PPM-18, Pyrrolidinedithiocarbamic acid ammonium salt, (R)-MG-132, Rocaglamide, Sodium Salicylate, QNZ, MG-132 [Z-Leu-Leu-Leu-CHO], Astaxanthin, (E)-2-Fluoro-4'-methoxystilbene, CHS-828, disulfiram, olmesartan, triptolide, withaferin, celastrol, tanshinone IIA, Ro 106-9920, cardamonin, BAY 11-7821, PSI, HU 211, ML130, PR 39, honokiol, CDI 2858522, andrographolide, and dithiocarbamates. The NF-κB inhibitor can also be a peptide inhibitor, e.g., a cell penetrating inhibitory peptide as described in May et al., *Science*, 2000 Sep. 1 ; 289(5484):1550-4 and in Orange and May, *Cell Mol. Life Sci.*, 2008 November; 65(22):3564-91, each of which is incorporated herein by reference. Additional NF-κB inhibitors are also described in Gilmore and Herscovitch, *Oncogene* (2006) 25, 6887-6899; Nam, *Mini Rev. Med. Chem.*, 2006 August; 6(8):945-51; and in U.S. Pat. No. 6,410,516, each of which is incorporated herein by reference.

Methods of Treatment Using a Treg-Depleted, Lymphocyte-Enriched Composition and/or Antagonist of the TNFR2 Signaling Pathway The invention features methods for treating proliferative disorders, e.g., cancers, by administering a composition enriched in lymphocytes and depleted of Tregs to a patient in need thereof. The composition enriched in lymphocytes can be produced by the methods described above, for example, by contacting cells obtained from a human sample, e.g., blood or bone marrow sample, with a TNFR2 antagonist, e.g., a TNFR2 antagonist antibody, and/or an NF-κB inhibitor to produce a composition enriched in lymphocytes and depleted of Tregs. An NF-κB inhibitor may be used in methods of treating proliferative disorders, e.g., cancers, instead of the composition enriched in lymphocytes and depleted of Tregs or in combination with this composition. The invention also features methods for treating proliferative disorders, e.g., cancers, by administering a composition containing a TNFR2 antagonist (e.g., an anti-TNFR2 antagonist antibody) to a patient in need thereof.

The invention features methods for treating infectious diseases, by administering a composition enriched in lymphocytes and depleted of Tregs to a patient in need thereof. The composition enriched in lymphocytes can be produced by the methods described above, for example, by contacting cells obtained from a human sample, e.g., blood or bone marrow sample, with a TNFR2 antagonist, e.g., a TNFR2 antagonist antibody, and/or an NF-κB inhibitor to produce a composition enriched in lymphocytes and depleted of Tregs. An NF-κB inhibitor may be used in methods of treating infectious diseases, instead of the composition enriched in lymphocytes and depleted of Tregs or in combination with this composition. The invention also features methods for treating infectious diseases, by administering a composition containing a TNFR2 antagonist (e.g., an anti-TNFR2 antagonist antibody) alone to a patient in need thereof.

Treatment of Proliferative Disorders Using an Enriched Lymphocyte Composition of the Invention Non-Treg lymphocytes in a patient's blood can be expanded and administered back to the patient in order to treat a proliferative disorder (e.g., a cancer). The enriched lymphocyte composition can be administered alone or in combination with one or more anti-cancer agents known in the art. The enriched lymphocyte composition can be prepared as follows: i) obtaining a sample e.g., a blood or bone marrow sample, from a human patient and isolating nucleated cells (e.g., lymphocytes, such as T lymphocytes, e.g., CD4+ cells, CD25+ cells, or CD4+CD25+ cells) present therein; ii) subjecting these cells to the lymphocyte expansion method described above to produce a composition enriched in lymphocytes and depleted of Tregs (e.g., a substantially homogenous population of lymphocytes in which Tregs comprise less than 10% of cells in the composition, preferably less than 5% of the cells in the composition or are absent in the expanded composition); and iii) introducing the composition enriched in lymphocytes into the patient without any post-expansion sorting of the lymphocytes. The above steps of the method of treatment can be performed in iterative cycles, where the number of cycles of treatment provided to a patient can be determined by the proliferative disorder being treated, the severity of the disorder, and/or the outcome of each treatment cycle, i.e., a change in the disease state. For example, changes in efficacy markers and/or in clinical outcomes can be used for determining the frequency with which blood or bone marrow should be drawn from a patient, the lymphocytes enriched (and Tregs depleted) from that blood, and the enriched lymphocytes administered to the patient. The enriched lymphocyte composition may also be prepared and stored for later use (e.g., frozen).

Preferably, the lymphocytes are obtained from a patient's own blood or bone marrow (i.e., autologous cells), although the following methods of treatment may also include the use of allogeneic lymphocytes with possible best fit HLA matching or from unrelated donors that have been expanded according to the above methods. Allogeneic lymphocytes preferentially share at least 4/6 HLA markers in common with the patient receiving the enriched lymphocyte composition.

Treatments for proliferative disorders according to the present invention may include inhibiting the NF-κB signaling pathway in combination with the administration of an enriched lymphocyte composition depleted of Tregs. Because TNFR2 signaling is transduced via the NF-κB pathway, the treatment of proliferative disorders according to the present invention can also include administering to a patient an inhibitor of the NF-κB pathway. For example, any one of the NF-κB inhibitors described above can be administered for treating a proliferative disorder. The NF-κB inhibitor can be administered by itself or in combination with the composition enriched in lymphocytes. The NF-κB inhibitor can also function independently of the TNFR2 signaling pathway.

Proliferative disorders that can be treated by administering the enriched lymphocyte/Treg depleted composition include one or more cancers selected from the group consisting of Acute Lymphoblastic Leukemia, Acute Lymphoblastic Leukemia, Acute Myeloid Leukemia, Adrenocortical Carcinoma; AIDS-Related Lymphoma, AIDS-Related Malignancies, Anal Cancer, Astrocytoma, Bile Duct Cancer, Bladder Cancer; Bone Cancer, Osteosarcoma/Malignant Fibrous Histiocytoma, Brain Stem Glioma, Visual Pathway and Hypothalamic Glioma, Breast Cancer, Bronchial Adenomas/Carcinoids, Chronic Lymphocytic Leukemia, Chronic Myelogenous Leukemia, Chronic Myeloproliferative Disorders, Clear Cell Sarcoma of Tendon Sheaths, Colon Cancer, Colorectal Cancer, Cutaneous T-Cell Lymphoma, Endometrial Cancer, Epithelial Cancer, Esophageal Cancer,Ewing's Family of Tumors, Extracranial Germ Cell Tumor, Extragonadal Germ Cell Tumor, Extrahepatic Bile Duct Cancer, Eye Cancer, Intraocular Melanoma, Retinoblastoma, Gallbladder Cancer, Gastric (Stomach) Cancer, Hairy Cell Leukemia, Head and Neck Cancer, Hepatocellular (Liver) Cancer, Hodgkin's Lymphoma, Hypopharyngeal Cancer, Kaposi's Sarcoma, Kidney Cancer, Laryngeal Cancer, Pituitary Cancer, Plasma Cell Neoplasm/Multiple Myeloma, Pleuropulmonary Blastoma, Skin Cancer, Small Cell Lung Cancer, Small Intestine Cancer, Soft Tissue Sarcoma, Squamous Neck Cancer, Testicular Cancer, Thyroid Cancer, Urethral Cancer, Uterine Sarcoma, and Vaginal Cancer. The proliferative disorders can also include solid tumors including malignancies (e.g., sarcomas, adenocarcinomas, and carcinomas) of the various organ systems, such as those of brain, lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Administration and dosage of the enriched lymphocyte composition in the method for treating a proliferative disease are discussed herein below.

Treatment of an Infectious Disease Using an Enriched Lymphocyte Composition of the Invention The invention also features methods of treating infectious diseases caused by any one or more of a virus, bacteria, a fungus, or a parasite. The methods involve administering a composition enriched in lymphocytes (e.g., CD8+ T cells, B cells, or natural killer cells) and depleted of Tregs. This composition can be produced by the methods described above. The methods of the invention can be used for treating viral infections caused by, e.g., a member of the Flaviviridae family (e.g., a member of the *Flavivirus, Pestivirus,* and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Paraná virus, Pichinde virus, Pirital virus, Sabiá virus, Tacaribe virus, Tamiami virus, Whitewater Arroyo virus, Chapare virus, and Lujo virus; a member of the Bunyaviridae family (e.g., a member of the *Hantavirus, Nairovirus, Orthobunyavirus,* and *Phlebovirus* genera), which includes the Hantaan virus, Sin Nombre virus, Dugbe virus, Bunyamwera virus, Rift Valley fever virus, La Crosse virus, California encephalitis virus, and Crimean-Congo hemorrhagic fever (CCHF) virus; a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxviridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1 N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively)).

The methods of the invention can also be used for treating bacterial infections. Examples of bacterial infections that may be treated include, but are not limited to, those caused by bacteria within the genera *Salmonella, Streptococcus, Bacillus, Listeria, Corynebacterium, Nocardia, Neisseria, Actinobacter, Moraxella, Enterobacteriacece, Pseudomonas, Escherichia, Klebsiella, Serratia, Enterobacter, Proteus, Salmonella, Shigella, Yersinia, Haemophilus, Bordatella, Legionella, Pasturella, Francisella, Brucella, Bartonella, Clostridium, Vibrio, Campylobacter,* and *Staphylococcus*.

The methods of the invention can also be used for treating parasitic infections caused by a protozoan parasite (e.g., an intestinal protozoa, a tissue protozoa, or a blood protozoa) or a helminthic parasite (e.g., a nematode, a helminth, an adenophorea, a secementea, a trematode, a fluke (blood flukes, liver flukes, intestinal flukes, and lung flukes), or a cestode). Exemplary protozoan parasites include *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis,* and *Histomonas meleagridis*. Exemplary helminthic parasites include *Richuris trichiura, Ascaris lumbricoides, Enterobius vermicularis, Ancylostoma duodenale, Necator americanus, Strongyloides stercoralis, Wuchereria bancrofti,* and *Dracunculus medinensis, Schistosoma mansoni, Schistosoma haematobium, Schistosoma japonicum, Fasciola hepatica, Fasciola gigantica, Heterophyes heterophyes,* and *Paragonimus westermani, Taenia solium, Taenia saginata, Hymenolepis nana,* and *Echinococcus granulosus.*

The methods of the invention can also be used for treating fungal infections. Examples of fungal infections that may be treated include, but are not limited to, those caused by, e.g., *Aspergillus, Candida, Malassezia, Trichosporon, Fusarium, Acremonium, Rhizopus, Mucor, Pneumocystis,* and *Absidia.*

Administration and dosage of the lymphocyte-enriched composition in methods for treating an infectious disease are discussed herein below.

Dosage

The composition enriched in Tregs can be administered to a patient in need thereof one or more times per day, week, month (e.g., one or more times every 2 weeks), or year depending on the severity of the disease and change in disease state of the patient during the treatment. Generally it is expected that a typical dosage would include $5\times10^5$ to $5\times10^{12}$ (e.g., $5\times10^5$, $5\times10^6$, $5\times10^7$, $5\times10^8$, $5\times10^9$, $5\times10^{10}$, $5\times10^{11}$, or $5\times10^{12}$) Tregs. Disease metrics, such as severity of symptoms, change in symptoms, patient response to treatment, any adverse effects of treatment, and/or effect of any additional treatment(s), can be used to determine the frequency of treatment and the dosage, i.e., the number of Tregs to be administered to a patient.

The composition enriched in lymphocytes (and depleted of Tregs) can be administered one or more times per day, week, month (e.g., one or more times every 2 weeks), or year depending on the severity of the disease and change in disease state of the patient during the treatment. Preferably, less than 10% of the cells (e.g., less than 9%, 8%, 7%, 5%, %, 1% or none of the cells) in this composition enriched in lymphocytes are Tregs. Generally it is expected that a typical dosage would include $5\times10^5$ to $5\times10^{12}$ (e.g., $5\times10^5$, $5\times10^6$, $5\times10^7$, $5\times10^8$, $5\times10^9$, $5\times10^{10}$, $5\times10^{11}$, or $5\times10^{12}$) cells in the enriched lymphocyte composition. Disease metrics, such as severity of symptoms, change in symptoms, patient response to treatment, any adverse effects of treatment, and/or effect of any additional treatment(s), can be used to determine the frequency of treatment and the dosage, i.e., the number of lymphocytes to be administered to a patient.

Administration

Generally, the compositions of the invention (e.g., the composition enriched in Tregs or the composition enriched in lymphocytes and depleted of Tregs) can be administered in any medically useful form. For example, such compositions may include the addition of compounds, e.g., adjuvants, preservatives, carriers, excipients, diluents, anti-bacterial or anti-mycotic agents, anti-inflammatory agents, and/or anti-cancer agents, where appropriate. The compositions of the invention can be administered intravenously, intramuscularly, orally, by inhalation, parenterally, intraperitoneally, intraarterially, transdermally, sublingually, nasally, transbuccally, liposomally, adiposally, ophthalmically, intraocularly, subcutaneously, intrathecally, orally, or locally, and they are formulated, as appropriate, depending on the chosen route of administration.

Administration of Antibodies of the Invention

Pharmaceutical compositions containing an anti-TNFR2 antibody of the invention (e.g., an anti-TNFR2 antagonist antibody) are prepared for storage by mixing the antibody having the desired degree of purity with optional physiologically acceptable carriers, excipients or stabilizers in the form of aqueous solutions, lyophilized or other dried formulations. The acceptable excipient or carrier is selected on the basis of the mode and route of administration. Suitable pharmaceutical carriers, as well as pharmaceutical necessities for use in pharmaceutical formulations, are described in *Remington: The Science and Practice of Pharmacy, 21st* edition, Ed. Gennaro; Lippincott, Williams & Wilkins (2005), a well-known reference text in this field, and in the USP/NF (United States Pharmacopeia and the National Formulary). Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Other exemplary excipients are described in *Handbook of Pharmaceutical Excipients, 6th* Edition, Rowe et al., Eds., Pharmaceutical Press (2009).

The compositions of the invention may be prepared in a pharmaceutically acceptable carrier or excipient. Such suitable carriers or excipients may be selected from, for example, water, saline (e.g., phosphate-buffered saline (PBS) or acetate-buffered saline (ABS), or Ringer's solution), dextrose, glycerol, ethanol, or the like and combinations thereof. In addition, if desired, a composition for administration to a mammal can contain minor amounts of auxiliary substances, such as wetting or emulsifying agents, or pH buffering agents that enhance the effectiveness of the composition. The compositions of the invention may also be prepared in any acceptable salt formulation. Other agents that may be used in preparation of the compositions of the invention include, e.g., adjuvants, preservatives, diluents, anti-bacterial or anti-mycotic agents, anti-inflammatory agents, and/or anti-cancer agents, where appropriate.

The compositions may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy, 21st* edition, Ed. Gennaro; Lippincott, Williams & Wilkins (2005).

The compositions to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

The compositions containing one or more anti-TNFR2 antibodies (e.g., anti-TNFR2 antagonist antibody) may be administered to a patient prior to the development of symptoms of a proliferative disease or an infectious disease or the compositions may be administered to the patient after diagnosis with a proliferative disease or an infectious disease after presentation with one or more (e.g., 1, 2, 3, 4, or 5) symptoms of the disease. The dosage of the anti-TNFR2 antibodies depends on the patient's state of health, but generally ranges from about 0.1 mg to about 400 mg of an antibody per dose (e.g., 1 mg, 5 mg, 10 mg, 20 mg, 50 mg, 100 mg, 200 mg, 300 mg, or 400 mg or more per dose).

The compositions may be administered to a patient in one or more doses (e.g., 2, 3, 4, 5, 6, 7, 8, 9, or 10 or more doses). If more than one dose is administered, the doses may be administered via the same mode of administration (e.g., intravenous administration) or by different modes of administration (e.g., intravenous and intramuscular administration). The patient may also be administered different doses at different times. For example, the patient may be administered a higher initial dose and lower subsequent doses over the course of treatment or vice versa.

The compositions may be administered daily, weekly, monthly, or yearly. For example, a dose of the composition may be administered twice daily, biweekly, bi-annually, tri-annually, or quarterly. The dose of the composition may be determined by a skilled physician upon consideration of a subject's clinical symptoms and/or physical condition (e.g., weight, sex, height, and severity of the proliferative or infectious disease). The composition may be administered by intravenous, intradermal, parenteral, intra-arterial, subcutaneous, intramuscular, intraorbital, topical, intraventricular, intraspinal, intraperitoneal, intranasal, intracranial, or oral administration.

Kits of the Invention

The invention features a kit for the production of a composition enriched in Tregs. The kit can include a TNFR2 agonist (e.g., a TNFR2 agonist antibody) or an NF-κB activator (e.g., one or more of the NF-κB activators described above), reagents and/or devices for isolating a human sample, e.g., a blood or bone marrow sample, reagents and/or devices for isolating blood or bone marrow cells (e.g., CD4+CD25+ cells) from the sample, and reagents for culturing the blood or bone marrow cells (e.g., anti-CD3 antibody, anti-CD28 antibody, interleukin-2, and/or rapamycin). Additionally the kit of the invention can also include instructions for performing the method of the invention, e.g., instructions for isolating a blood or bone marrow sample and blood or bone marrow cells therefrom, instructions for contacting blood or bone marrow cells with a TNFR2 agonist, and/or instructions for culturing, harvesting and/or storing the enriched Tregs. The kit of the invention can also include reagents and instructions for assaying the expression of various marker genes that can be used to characterize the Tregs. For example, these can include reagents and instructions for detecting the mRNA or protein levels of one or more of FOXP3, CTLA4, TNFR2, CD62L, Fas, HLA-DR, CD45RO, CD127, CCR5, CCR6, CCR7, CXCR3, IFN-gamma, IL10, and ICOS.

The invention features a kit for the production of a composition enriched in lymphocytes and depleted of Tregs. The kit can include a TNFR2 antagonist (e.g., a TNFR2 antagonist antibody) or an NF-κB inhibitor (e.g., one or more of the NF-κB inhibitors described above), reagents and/or devices for isolating a human blood or bone marrow sample, reagents and/or devices for isolating blood or bone marrow cells (e.g., T lymphocytes, such as CD4+ cells, CD25+ cells, or 004+0025+ cells) from the sample, and reagents for culturing the blood cells (e.g., anti-CD3 antibody, anti-CD28 antibody, interleukin-2, and/or rapamycin). Additionally the kit of the invention can also include instructions for performing the method of the invention, e.g., instructions for isolating a blood or bone marrow sample and blood or bone marrow cells therefrom, instructions for contacting blood cells with a TNFR2 antagonist, and/or instructions for culturing, harvesting and/or storing the enriched lymphocytes. The kit of the invention can also include reagents and instructions for assaying the expression of various marker genes that can be used to characterize the lymphocytes. For example, these can include reagents and instructions for detecting the mRNA or protein levels of one or more of FOXP3, TRAF2, TRAF3, and cIAP.

The invention also features kits that include a composition containing an anti-TNFR2 antibody (e.g., an anti-TNFR2 antagonist antibody), a pharmaceutically-acceptable carrier or excipient, and, optionally, other agents as described herein; the composition contains an effective amount of the anti-TNFR2 antibody for treating a proliferative disease or an infectious disease. The kits may include instructions explaining how a practitioner (e.g., a physician, nurse, or patient) may administer the composition contained therein. Furthermore, the kits may also include additional components, such as one or more additional components described above, instructions or administration schedules for a patient suffering from a proliferative disease or an infectious disease, and, optionally, a device(s) for administering the composition (e.g., a syringe).

The following examples are meant to illustrate the invention. They are not meant to limit the invention in any way.

EXAMPLES

Materials and Methods

Human Subjects and TNF-α Induction with BCG Vaccine

Two BCG vaccinations were used to induce TNF-α. Administration of BCG was approved by the Human Studies Committee at Massachusetts General Hospital and by the FDA (NCT00607230).

For the double-blinded placebo-controlled trial, one subject was injected with BCG at a dose of $1.6\text{-}3.2\times10^6$ cfu and the placebo subject was injected with saline. The BCG or saline injection was administered intradermally on two occasions four-weeks apart. All blood samples were blinded and simultaneously sent to the laboratory for monitoring TNF-α and Treg levels.

Reagents and Flow Cytometry

Recombinant human TNF-α was purchased from Leinco Technologies (St. Louis, Mo.), and recombinant human IL-2 was purchased from Sigma-Aldrich (St. Louis, Mo.). Monoclonal antibodies against TNFR1 and TNFR2 used for screening purposes were from internal sources and external vendors (Table 1). External vendors included R&D Systems, Inc., Hycult-Biotechnology, BD-Pharmingen, Accurate, Abcam and Sigma. All other antibodies were purchased from BD-Biosciences. Intracellular staining of FOXP3 and CD152 were performed using either FOXP3 Fix/Perm Buffer set (Biolegend) or Human FOXP3 Buffer set (BD Biosciences). The avidities of MAB726 and M1 antibodies for TNFR2 were determined using surface plasmon resonance on Pioneer SensiQ (SensiQ Technologies, Oklahoma City, Okla.).

TABLE 1

| Clone | MR2-1 | 80M2 | MAB726 | M1 | MAB2261 |
|---|---|---|---|---|---|
| Isotype | Mouse IgG1 | Mouse IgG1 | Mouse IgG1 | Rat IgG2b | Mouse IgG2A |
| Properties | Agonist | Neutral | Antagonist | Antagonist | Agonist |
| Vendor | Cell Sciences | Cell Sciences | R&D | BD Biosciences | R&D |

CD4+ Cell isolation, induction of FOXP3, and expansion of CD4+CD25+ cells

CD4+ T cells were isolated using Dynal CD4 Positive Isolation Kit (Invitrogen). Extraction of CD25 positive cells was subsequently performed after CD4+ isolation using Dynabeads CD25 and DETACHaBEAD CD4/CD8 (Invitrogen). After isolation, $2\times10^4$ cells were cultured in 96-round-bottom well plate. Dynabeads for human Treg Expander (Invitrogen) (Dynabeads coupled with anti-CD3 and anti-CD28 monoclonal antibodies) was added at a beads-to-cell ratio of 2:1. In selected wells, TNF-α (20ng/ml), TNFR2 mAbs (2.5 µg/ml), rapamycin (1 µM, EMD Biosciences, San Diego, Calif.) were added. After two days, IL-2 (200 U/ml) was added to the culture. Half of the media was changed every 2 to 3 days containing rapamycin (until day 7) and 100 U/ml of IL-2. On day 9, additional TNF-α or TNFR2 mAbs were supplied into the media. On day 16, cells were harvested, Dynabeads Human Treg Expander was removed, washed and rested. On the following day, cells were analyzed.

Intracellular Staining

Expanded CD4+CD25+ cells were stimulated with phorbol myristate acetate (PMA) (2 ng/ml) and ionomycin (500 ng/ml) (Sigma) for 24 hours. Monensin (GolgiStop, BD Biosciences) was added for the last 4 hours of incubation. Cells were fixed and permeabilized using Human FOXP3 Buffer Set, followed by staining with fluorochrome-conjugated IFNγ and IL-10 mAbs.

mRNA Isolation

Isolated CD4+ cells were incubated in presence of IL-2 (50 U/ml) with or without TNFR2 mAbs (2.5 µg/ml). After 3 hours, cells were collected and total RNA was isolated using RNAqueous-4PCR kit (Ambion, Austin, Tex.). The extracted RNA was reverse transcribed using High Capacity cDNA Reverse Transcription Kit (Applied-Biosystems, Foster City, Calif.).

Cell Proliferation and Suppression Assays

For CD4 proliferation experiments, CD4+ cells were stained with 1 µM carboxyfluorescein diacetate succinimidyl ester (CFSE). Cells were plated at the density of $2\times10^5$ cells/well in 96-well plate with anti-CD3mAbs. Four days later, cells were collected and analyzed.

For Treg suppression assay, autologous PBMCs were used as responders. PBMC were collected using Ficoll-Paque, cryopreserved at −80° C., and thawed the day before mixing with Tregs and rested overnight in RPMI 1640 and 10 U/ml IL-2. The next day, responder cells were stained with CFSE (1 µM). Responder cells ($5\times10^4$ cells) and expanded Tregs were mixed at various ratios, and stimulated with anti-CD3mAb and IL-2. After 4 days, cells were collected and analyzed.

Statistical Analysis

All data analyses were performed by the paired Student t test using GraphPad Prism-5 software (GraphPad Software, La Jolla, Calif.). I considered two-sided p value 0.05 as significant.

Example 1

Clinical Trial Induction of Human Tregs

Unexpanded, naturally occurring human Tregs are heterogeneous and rare in blood. Homogeneous populations of Tregs are difficult to expand in vitro even with multiple ligand mixtures. With the goal of expanding sufficient numbers of homogeneous populations of human Treg cells TNF-α, I first sought to confirm or refute an increase in Treg concentrations by induction with native TNF-α. Because an FDA-approved version of TNF-α does not exist and manufacturing of a stable form is difficult, I administered a well-known, strong inducer of TNF-α, Bacillus Calmette Guérin (BCG), a generic vaccine already on the market for decades for tuberculosis and bladder cancer. This method of inducing endogenous TNF-α eliminated the manufacturing problems of TNF-α that forms unnatural monomers, dimers and trimers with differential cellular effects.

The small, double-blinded placebo-controlled clinical trial enrolled two subjects. One human subject received BCG injections ($1.6-3.2\times10^6$ cfu/injection) and the placebo received saline, twice, 4-weeks apart. Both were monitored weekly for 20-weeks to study the pharmacokinetics of TNF-α and Treg induction. After each injection TNF-α induced Tregs in a bi-modal fashion with slightly delayed kinetics (FIG. 1A, left panels). After 20 weeks of observation, saline injections induced neither TNF-α nor Tregs. The total CD4+ cell counts did not change in BCG and placebo patients other than in the percentages of CD4+CD25$^{hi}$FOXP3+ depicted in FIG. 1A. This in vivo evidence confirms endogenous TNF-α in vivo increases the numbers of Tregs but since TNF-α binds to both the TNFR1 and TNFR2 receptors, it does not clarify which receptor was more central for the Tregs effect.

Example 2

Functional Effects of TNFR Monoclonal Antibodies and Signaling Pathways

Figure 1B:
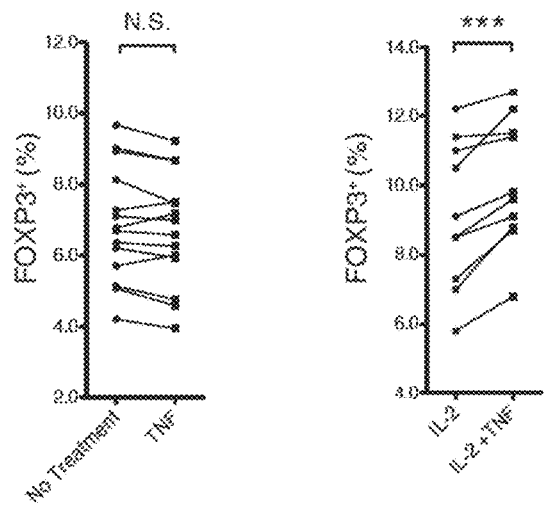
FIG. 1B is a set of graphs showing that in freshly isolated CD4+ cells from fresh human blood, TNF-α alone does not induce FOXP3 in culture (left graph), but does induce it to higher levels when co-incubated with IL-2, compared to IL-2 alone (right graph). The data are from 14 subjects (left panel) and 10 subjects (right panel).
Figure 1C:
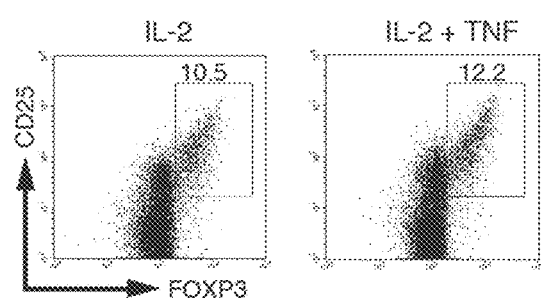
FIG. 1C is a set of representative flow cytometry histograms that confirm greater intracellular induction of FOXP3 in CD4+CD25$^{hi}$ Tregs after co-incubation with TNF-α and IL-2 than with IL-2 alone. Figures in flow diagrams are %. [*P<0.05 or **P<0.01, by paired t-test].

I cultured freshly isolated human CD4+ cells from 14 human subjects only with TNF-α for 16 hours (FIG. 1 B). While finding no induction of Tregs, assessed by inducible FOXP3, I observed a significant increase in Tregs after adding IL-2. Co-incubation of TNF-α and IL-2 produced a significant increase in Tregs over IL-2 alone (FIG. 1 B). IL-2 is important for Tregs induction and maintenance in mice. Findings were confirmed by flow cytometry, in which co-incubation increased the percentage of CD4+CD25$^{hi}$FOXP3 cells in human cultured cells from blood (FIG. 1 C). Thus, the data in FIGS. 1B and 1C confirm that TNF-α can induce a homogeneous population of Tregs in vitro.

Figure 2A:
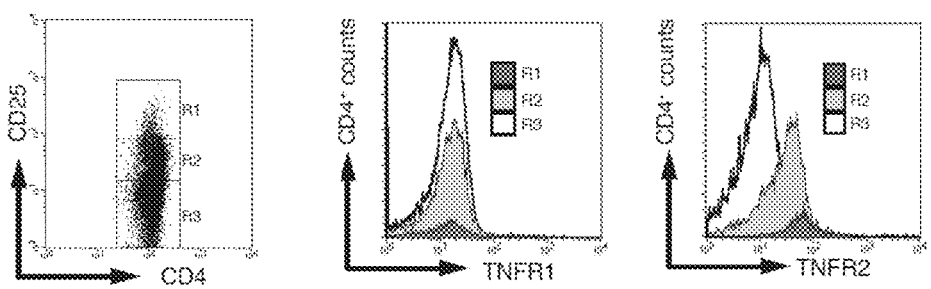
FIG. 2A is a set of graphs showing that TNFR2 is preferentially expressed on CD4+CD25$^{hi}$ T cells.

In freshly isolated CD4+ cells, I examined expression levels of each TNFR in relation to CD25+ expression. TNFR1 expression on CD4+ cells, regardless of CD25+ expression levels, was unchanged using flow cytometry (FIG. 2A, middle panel), whereas TNFR2 preferentially expressed CD4+CD25$^{hi}$ Tregs by nearly a factor of 10 (FIG. 2A, right panel). This confirms earlier studies that TNFR2 is more densely expressed on Tregs.

Figure 2B:
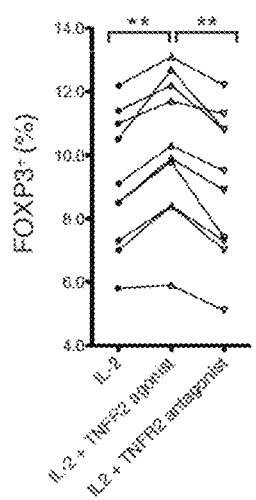
FIG. 2B is a graph showing that one TNFR2 antibody induced FOXP3, acting as an agonist, and the other TNFR2 antibody suppressed FOXP3+ expression, acting as antagonist.
Figure 7:
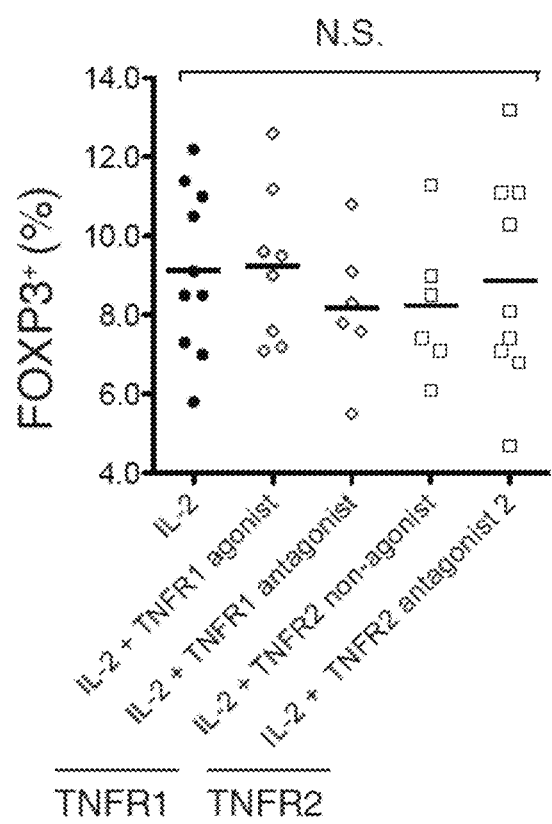
FIG. 7 is a graph showing the induction of FOXP3 expression by different TNFR agonists and antagonist antibodies. Screening anti-TNFR1 and anti-TNFR2 mAbs reveals that not all of the antibodies tested induce or inhibit FOXP3+ expression.

Screening several TNFR1 and TNFR2 monoclonal antibodies (mAbs) on isolated CD4+ cells sampled from fresh human blood enabled selective study of each TNF receptor, unlike studying TNF-α, which acts through both receptors and can have manufacturing problems from the use of E. coli and yeast systems. Although most of the screened TNFR1 or TNFR2 mAbs failed to induce or suppress FOXP3+ Tregs after stimulation by presence of IL-2 for 16 hours (FIGS. 7 and 8), I found two types of TNFR2 mAbs with significant, and opposing, effects on FOXP3 induction (FIG. 2b). Studying freshly cultured cells from 10 subjects, one TNFR2 antibody significantly induced FOXP3 expression in CD4+ human T cells (which I designated the "TNFR2 agonist"), whereas the other TNFR2 monoclonal suppressed intracellular FOXP3 expression (which I designated the "TNFR2 antagonist") (FIG. 2B). Thus, I have identified M1 and MAB726 as TNFR2 antagonists.

Figure 2C:
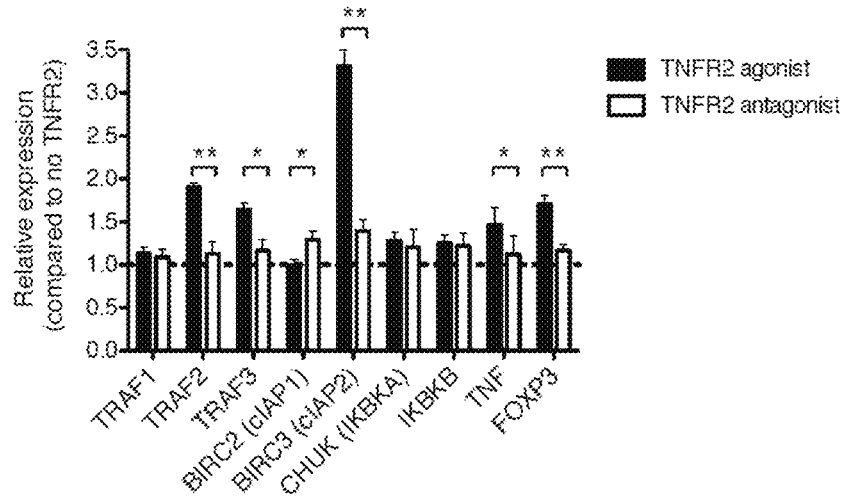
FIG. 2C is a graph showing that in a signaling pathway assay, purified CD4+ cells, incubated with IL-2, the TNFR2 agonist and antagonist trigger differences in relative downstream expression of mRNA, especially in signaling proteins TRAF2, TRAF3 and apoptosis inhibitor cIAP2 that were preferentially induced by TNFR2 agonism. Data represented are means±SEM from 4 subjects.

Having identified two functionally-opposing types of TNFR2 mAbs, I measured their effects on isolated CD4+ T cells by examining downstream mRNA expression in signaling proteins specific to TNFR2 activation. After 24 h stimulation by the TNFR2 agonist or antagonist, relative mRNA expression was significantly different. The TNFR2 agonist stimulated expression of TNF, TRAF2, TRAF3, cIAP2 and FOXP3. In contrast, the TNFR2 antagonist stimulated expression of cIAP1, but not TRAF2, TRAF3 or FOXP3 (FIG. 2C).

Figure 2D:
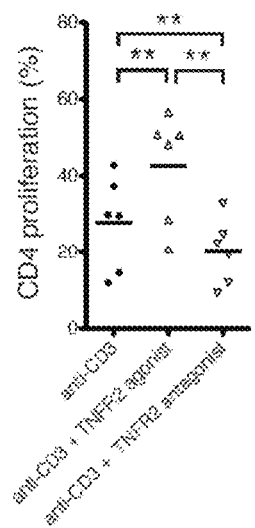
FIG. 2D is a set of graphs showing that TNFR2 agonist triggers greater % increase in proliferation in samples from 6 subjects measured by flow cytometry (left panel) and with carboxyfluorescein diacetate succinimidyl ester (CFSE) measurements (right panels) and representative results from a typical experiment is presented with CFSE measurements (right panels). The numbers in a bar represent the percentage of cells that went into division. The TNFR2 antagonist suppressed CD4+ proliferation (left panel) and inhibited expansion AS measured by CFSE dilution (right panel). *P<0.05 or ***P<0.01, by paired t-test.
Figure 2D:
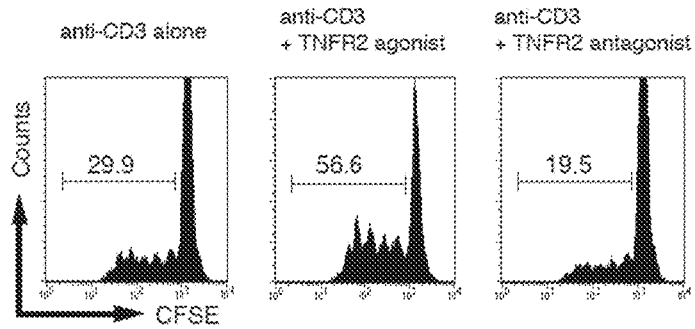

The effects of the TNFR2 agonist and antagonist were studied on purified human CD4+ T cells co-cultured with anti-CD3 or IL-2. When CD4+ proliferation was studied with anti-CD3 combined with the TNFR2 agonist, the highest degree of proliferation was shown by the agonist. In contrast, the TNFR2 antagonist (e.g., M1 or MAB726) suppressed CD4+ proliferation even relative to the control, anti-CD3 alone (FIG. 2D, left-most panel). The same findings were observed after 4 days by directly measuring CD4+ proliferation by flow cytometry and measuring CD4+ proliferation by CFSE dilution (FIG. 2D, three right-most panels). Thus, the opposing effects of TNFR2 agonist treatment versus TNFR2 antagonist treatment on Tregs have been demonstrated, as shown in FIGS. 2B-2D.

Figure 8:
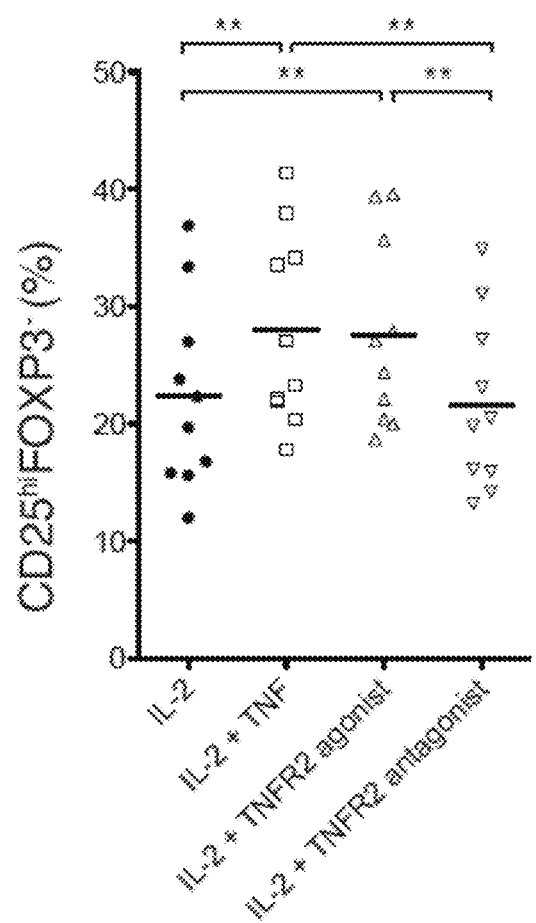
FIG. 8 is a graph showing the proportion of CD25+ FOXP3− cells after IL-2 overnight incubation with and without the TNFR2 agonist or antagonist. Significant percentage increases were observed if the treatment group was incubated in the presence of TNF or TNFR2 agonist. (**; $p<0.001$). Data are of samples from 10 subjects.

Despite high expression of TNFR2 on Tregs, some TNFR2 expression is also observable on CD4+ T cells that are not true Tregs because they only express intermediate levels of CD25, i.e., $CD4^+CD25^{mid}$ cells. I therefore studied the impact of overnight incubation on $CD25^{mid}$ cell subpopulations of IL-2 alone, IL-2 and TNF-α, or IL-2 and TNFR2 agonist, or IL-2 and TNFR2 antagonist. I found a rise in the proportion of $CD25^{hi}FOXP3^-$ cells similar to effector cells with IL-2 and TNF-α stimulation alone, or IL-2 and TNFR2 agonist alone (FIG. 8). However, I observed suppression with IL-2 and TNFR2 antagonist relative to the other three groups. Therefore, the TNFR2 agonist and antagonist, studied by the same assay, showed opposing trends on the same CD25+FOXP3− cell population. Thus, the addition of a TNFR2 antagonist (e.g., M1 or MAB726) inhibited expression of Foxp3 on CD4+CD25+ T cells.

Figure 3A:
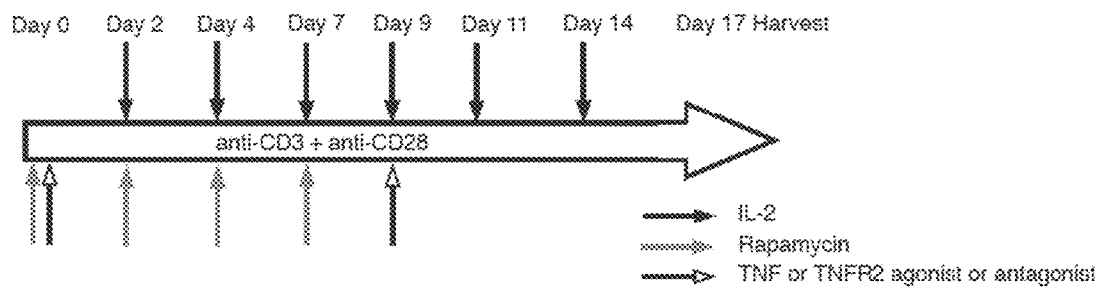
FIG. 3A is a schematic showing the protocol for purifying CD4+CD25$^{hi}$ cells from CD4+ cells from fresh blood and expanding for 16 days by incubation in 96 well round-bottom plate ($2\times10^4$ cells/well) with anti-CD3 and anti-CD28 antibodies, human IL-2, and rapamycin.
Figure 3B:
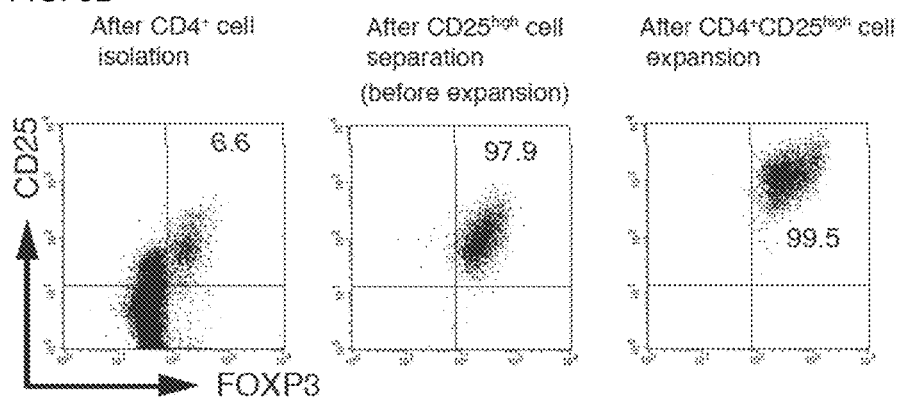
FIG. 3B is a set of graphs showing representative CD25 and FOXP3 flow diagrams of CD4+ cells before versus after CD25$^{hi}$ purification and expansion, indicating purity of populations.
Figure 3C:
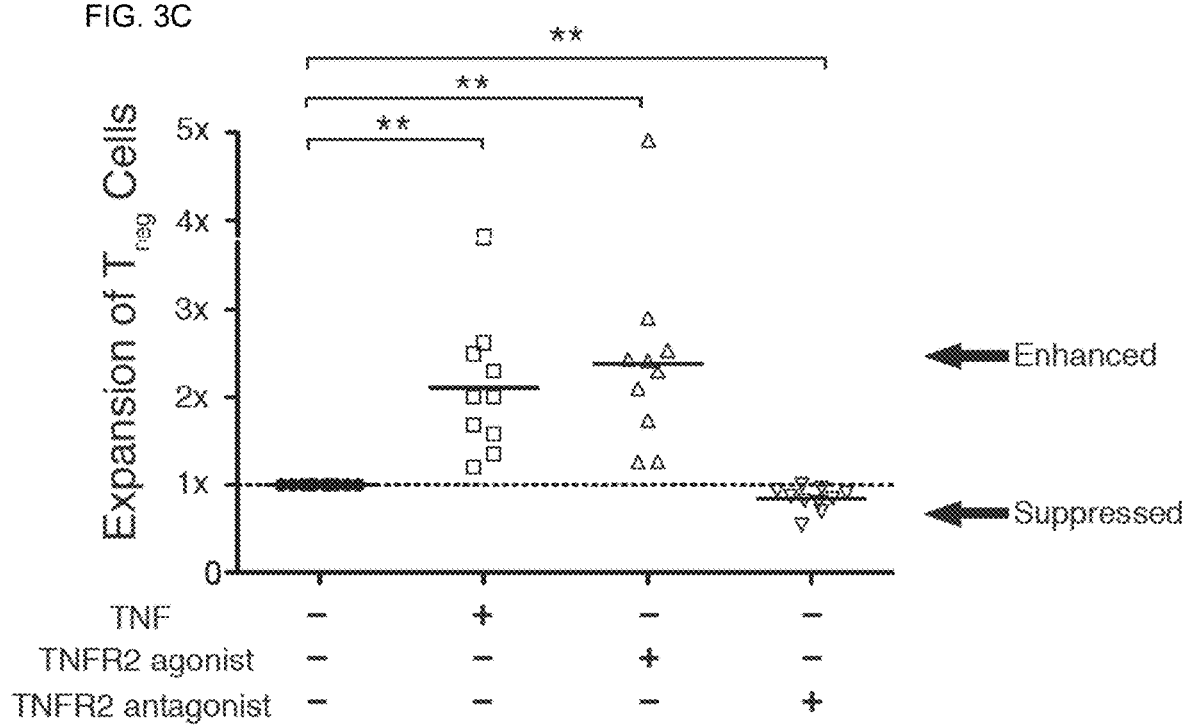
FIG. 3C is a graph showing cell counts of purified Tregs, by treatment group, reveal that TNFR2 agonist induced more expansion than any other group. *p<0.05, **p<0.01, by paired t-test. The TNFR2 antagonist suppressed expansion versus no treatment. Data in FIG. 3C are samples from 10 subjects.
Figure 9A:
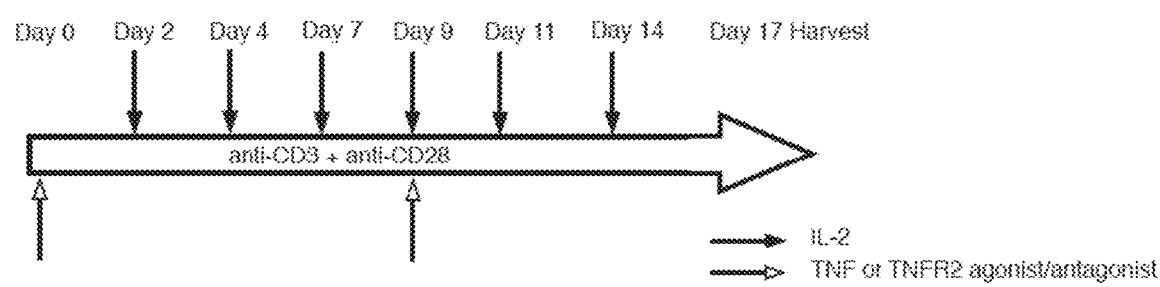
FIG. 9A is a schematic showing the expansion protocol. After 16 days of expansion, Tregs Expander Beads were removed and rested overnight for cell counting.
Figure 9B:
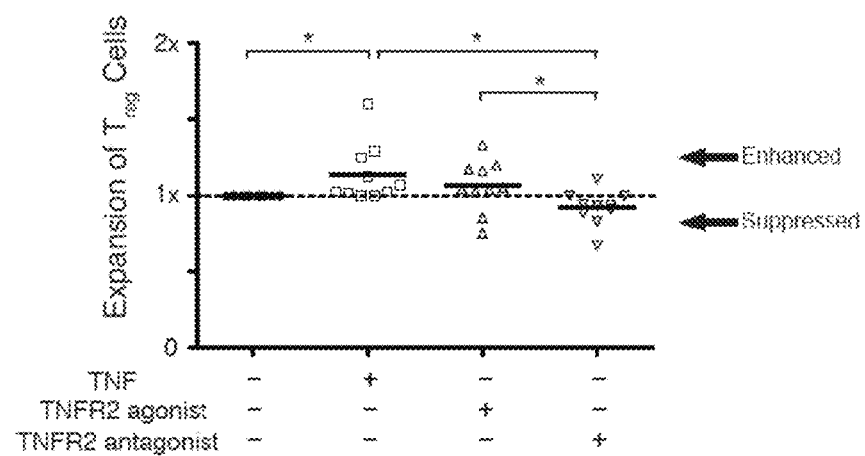
FIG. 9B is a graph showing the magnitude of expansion by each treatment group. (*; $p<0.05$, by paired t-test). Data in FIG. 9B are of samples from 10 subjects.

I separated fresh human blood to obtain pure CD4+ and $CD25^{hi}$ co-expressing Tregs (FIG. 3). I purified and expanded these Tregs in vitro using standard protocols of anti-CD3 anti-CD28 plus IL-2 for 16 days (FIG. 3A), then rested them overnight before counting. I added rapamycin (until day 7) because it selectively expands the highest number of Tregs with greatest capacity for suppressing CD8+ cells. This process successfully produced CD4+ $CD25^{hi}$ Tregs (FIG. 3B). I assessed $T_{reg}$ expansion by treatment group: no treatment, treatment with TNF-α, TNFR2 agonist, or TNFR2 antagonist. The TNFR2 agonist outperformed every other group, expanding Tregs at least twofold higher than no treatment or antagonist treatment. The latter suppressed expansion because its effect was less than that of no treatment. Because rapamycin is known to inhibit proliferation, I examined the effects of treatment without rapamycin, yet found similarly opposing effects between agonist versus antagonist treatment, albeit at smaller mean absolute values (FIG. 9B). The yields of expanded cells tended to be less without rapamycin, but the agonist still expanded Tregs.

Example 3

TNFR2 Agonist Expansion and Homogeneity of Tregs

Figure 4A:
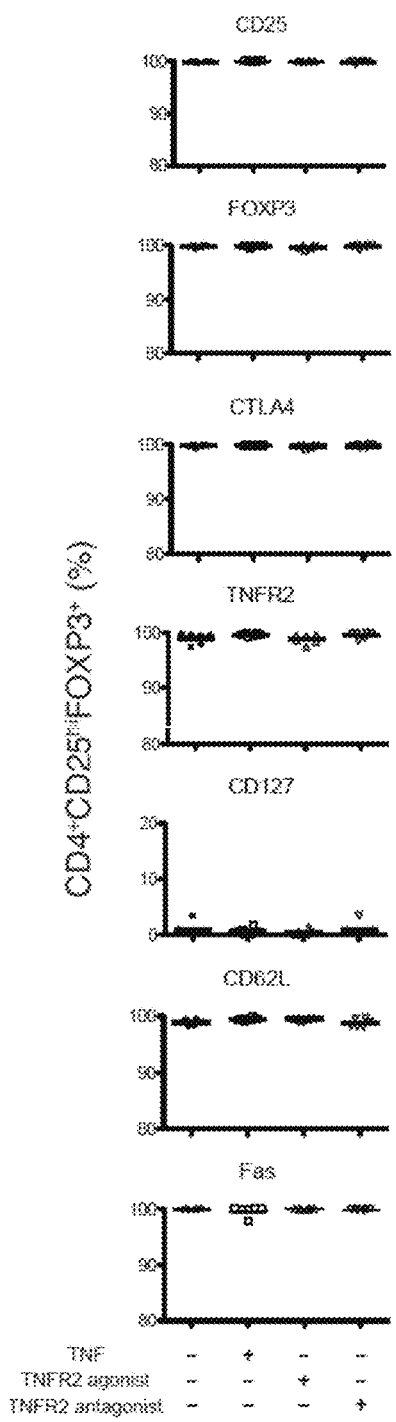
FIG. 4A is a set of graphs showing that all treatment groups are highly positive for Treg markers such as CD25, FOXP3, CTLA4, TNFR2, CD62L, and Fas and negative for CD127.
Figure 4B:
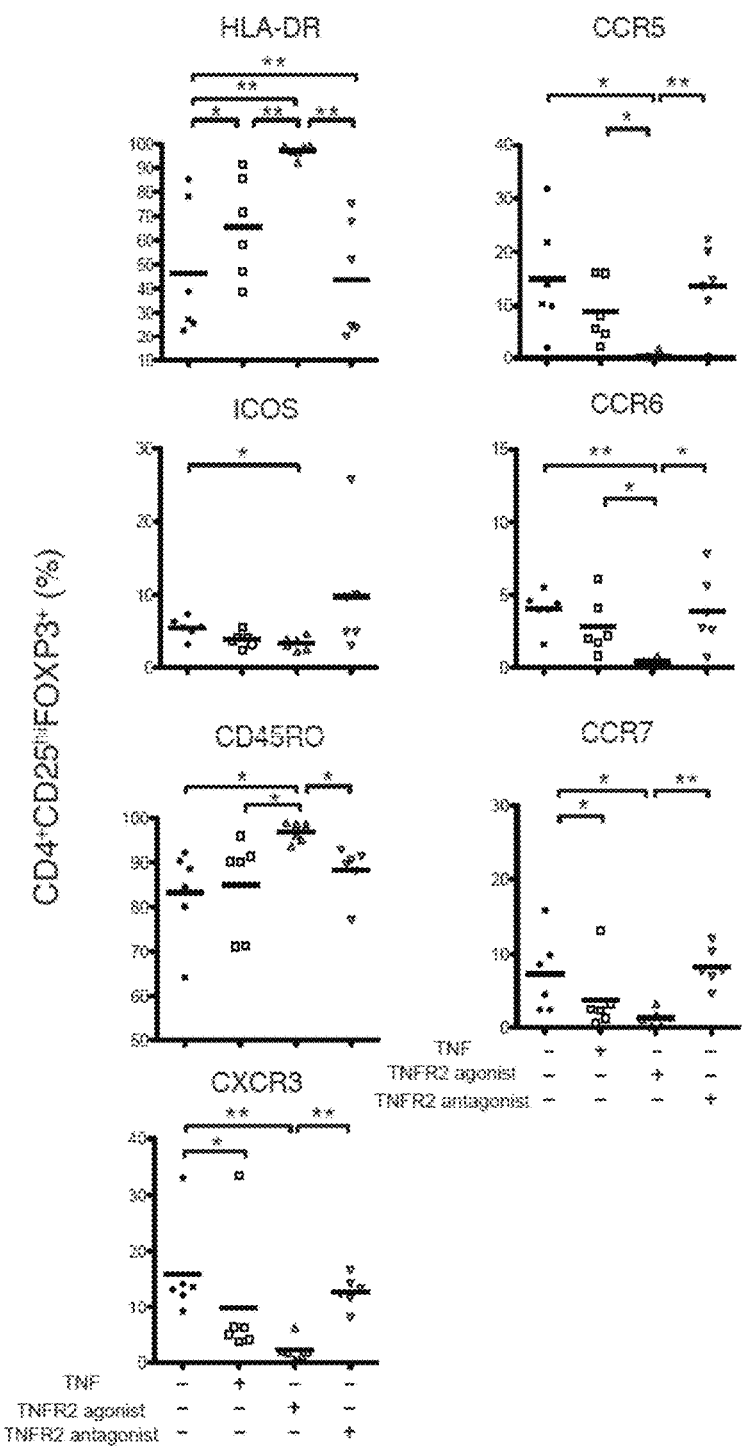
FIG. 4B is a set of graphs showing that TNFR2 agonist-treated Tregs almost uniformly express HLA-DR and CD45RO and almost uniformly lack markers such as ICOS, CXCR3, CCR5, CCR6, CCR7, and CXCR3.
Figure 4C:
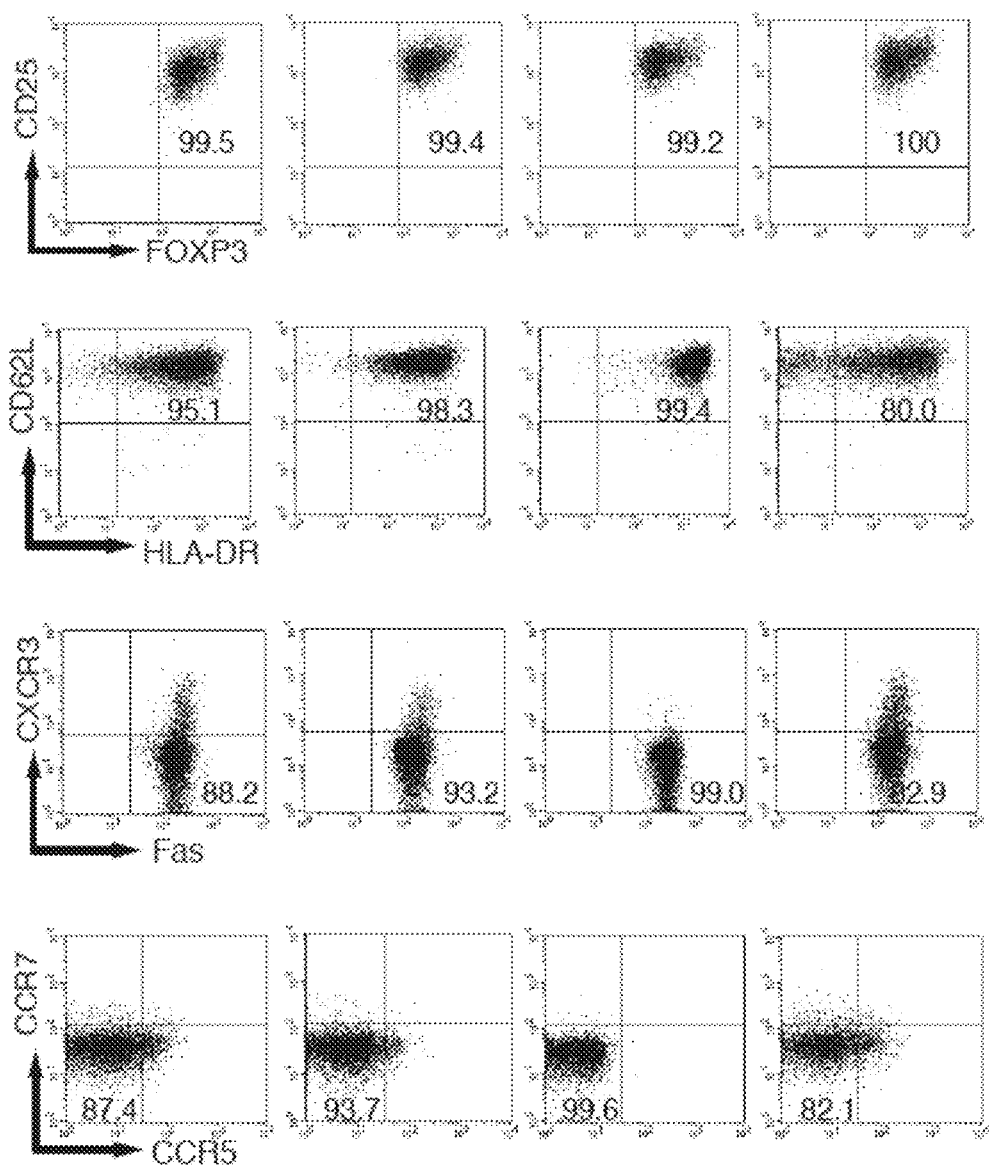
FIG. 4C is a set of representative flow diagrams showing that TNFR2 agonist-treated Tregs have greater uniformity of Treg markers than do other groups (*$p<0.05$, **$p<0.01$ by t-test).
Figure 10A:
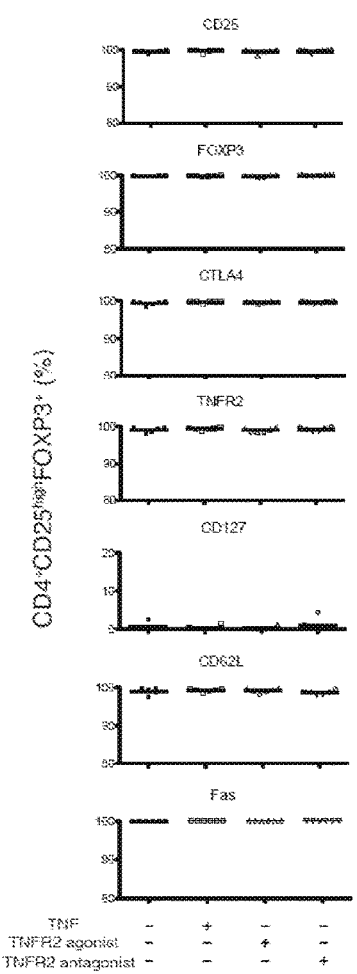
FIG. 10A is a set of graphs showing that all cells were positive for Fas.
Figure 10B:
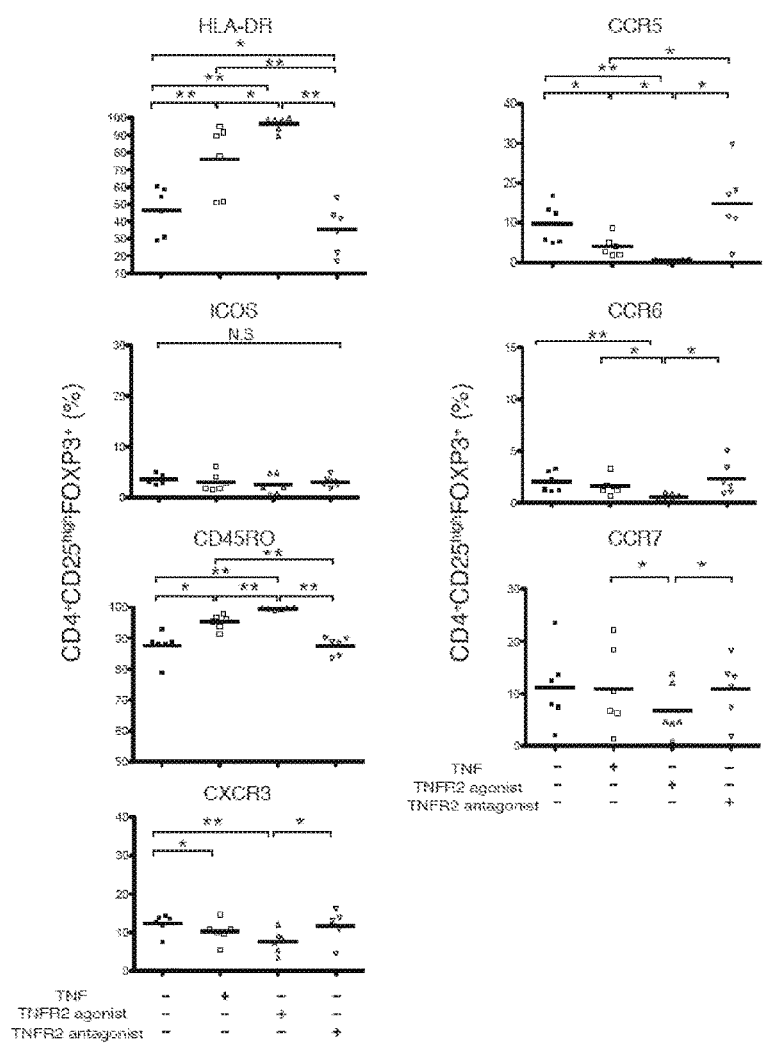
FIG. 10B is a set of graphs showing that some surface markers showed diverse patterns of expression according to the way the cells were expanded with a similar trend compared to cells expanded using rapamycin. (*; $p<0.05$, **; $p<0.01$) determined by paired t test). Data are from 6 subjects.
Figure 11A:
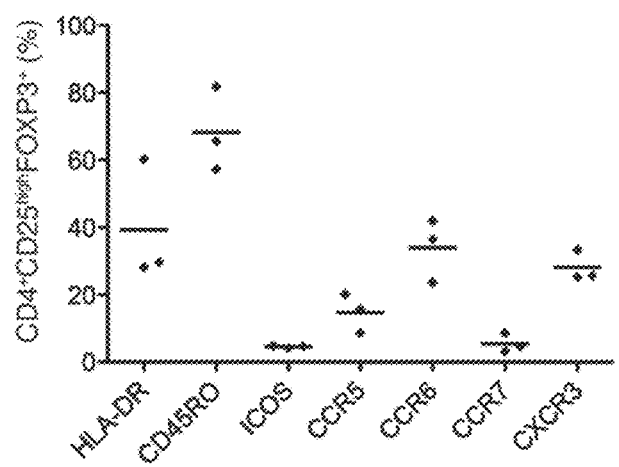
FIG. 11A is a graph showing the phenotypes of freshly separated Tregs before expansion (N=3, samples from 3 subjects).
Figure 11B:
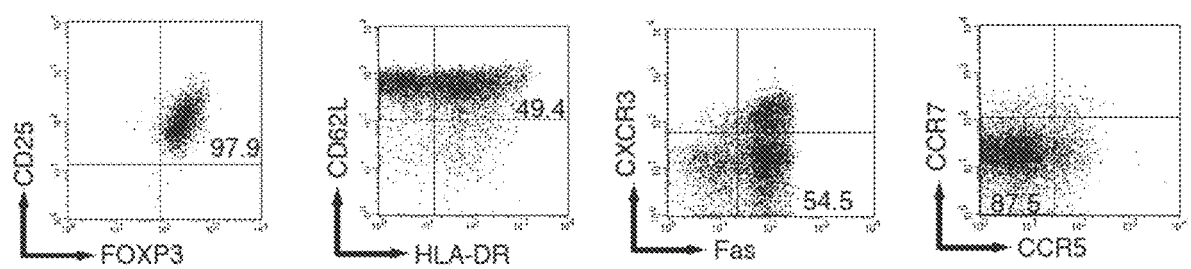
FIG. 11B is a set of graphs showing representative flow diagrams of Tregs markers before expansion.
Figure 12:
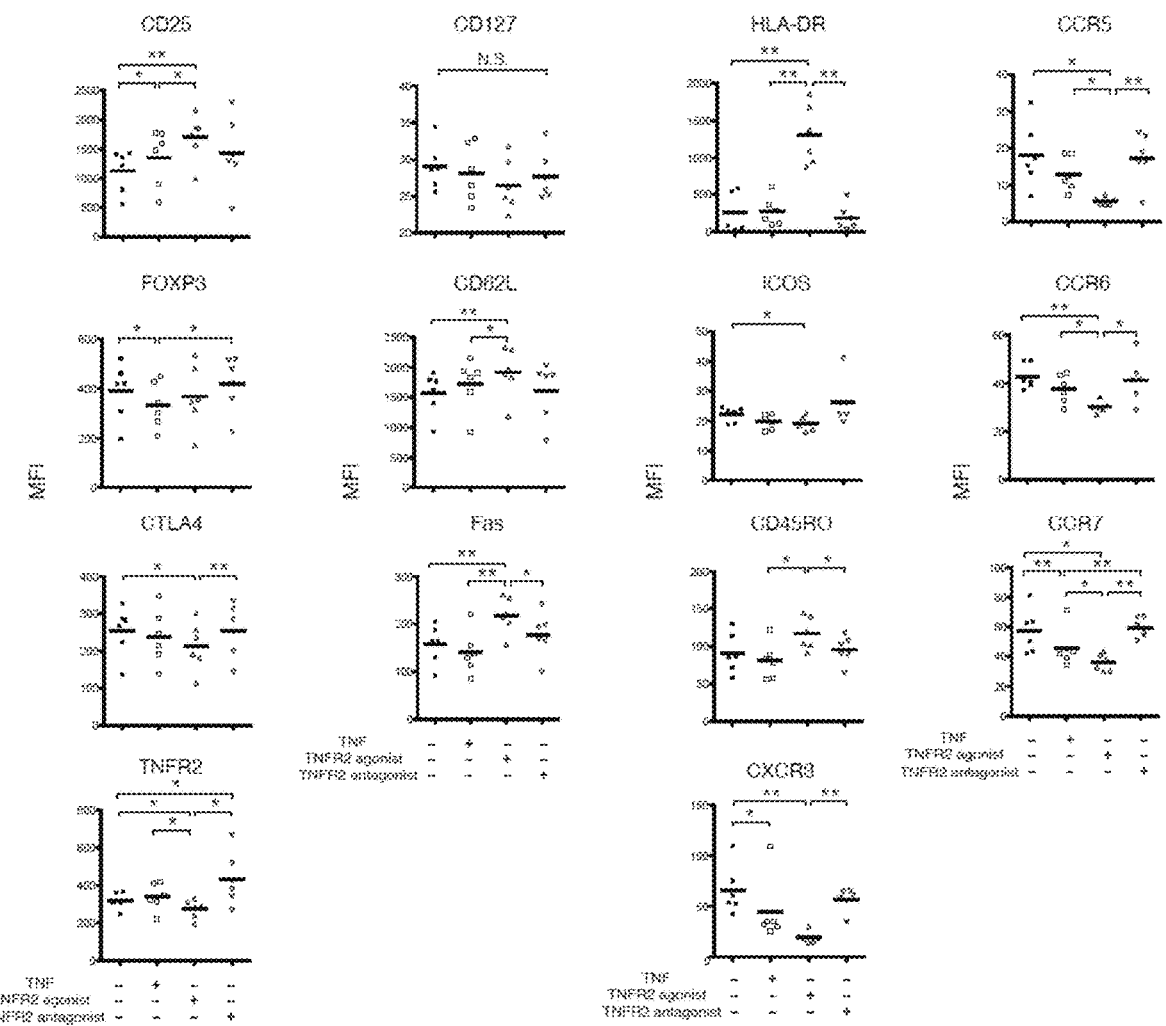
FIG. 12 is a set of graphs showing the density of cell surface markers measured by Mean Fluorescence Intensity (MFI). MFI of Tregs demonstrates clear differences between TNFR2 agonist expanded cells and TNFR2 antagonist expanded cells. (*$p<0.05$, **$p<0.01$ determined by paired t test).

I next investigated whether in vitro Tregs, treated by TNFR2 agonist, possessed more homogeneous Treg cell surface markers than those treated by the antagonist. Comparing phenotypes for 14 cell surface markers, all treatment groups highly expressed Treg signature markers FOXP3 and CD25 (FIG. 4A). The expression levels of FOXP3 were similar to levels before treatment. However, CD25+ expression was much higher after agonist treatment, which can be considered an expansion effect rather than an antagonist effect (data not shown). Nearly 100% of expanded $CD25^{hi}$ Tregs in each group were positive for CTLA4, TNFR2, CD62L, Fas, and negative for CD127 (FIG. 4A). Tregs treated with TNFR2 antagonist also maintained expression for these markers. In contrast, several other surface markers, such as HLA-DR, ICOS, CD45RO and chemokine receptors, were differentially expressed between the agonist vs. antagonist treatment (FIGS. 4B and 4C and FIG. 10). Similar results were observed in Tregs expanded without rapamycin (FIG. 10). Tregs expanded by TNFR2 agonist—relative to most other comparator groups, especially the TNFR2 antagonist—yielded a surprisingly homogeneous population of cells with this phenotype: CD4+ $CD25^{hi}FOXP3^+CTLA4^+TNFR2^+CD127^-CD62L^+Fas^+$ $HLA-DR^+CD45RO^+CCR5^-CCR6^-CCR7^-CXCR3^-ICOS^-$. The mean fluorescence intensity (MFI), a direct measure of the average density of the protein per cell, similarly revealed that for most surface markers, the TNFR2-agonist treated cells showed opposing expression levels compared to TNFR2-antagonist treated cells (FIG. 12). Further investigation should define whether these expanded cells maintain phenotypic homogeneity over time but the evidence from this conventional expansion protocol shows that they were more homogeneous than other groups. Before treatment, Treg markers were more heterogeneous (FIG. 11). Unexpanded, naturally occurring human Tregs are heterogeneous populations. In vitro studies of mixed Treg populations, which include $CD45RO^+FOXP3^{low}$ T cells, produce pro-inflammatory cytokines. This particular phenotype is found in up to 50% of FOXP3+ T cells.

One of the most upregulated markers by TNFR2 agonist-treated Tregs was HLA-DR, which is reported to have higher suppressive activity against CD8 T+ cells, suggestive of an effector Treg. In contrast to HLA-DR, all four chemokine receptors were strongly down-regulated. Although the lack of chemokine receptors might result in failure to migrate to the site of inflammation, another homing receptor, CD62L, which was highly expressed in all treatment groups (FIG. 4), is crucial for entering the site of pathogenic T cell presence in acute GVHD. The fact that agonist-treated Tregs were CD45RO+ and CCR7− and displayed significantly higher expression levels of Fas, measured by MFI (FIG. 12), contributes to the view that they are activated effector Tregs.

Example 4

TNFR2 Agonist-Treated Tregs and CD8+ Suppression

Figure 5A:
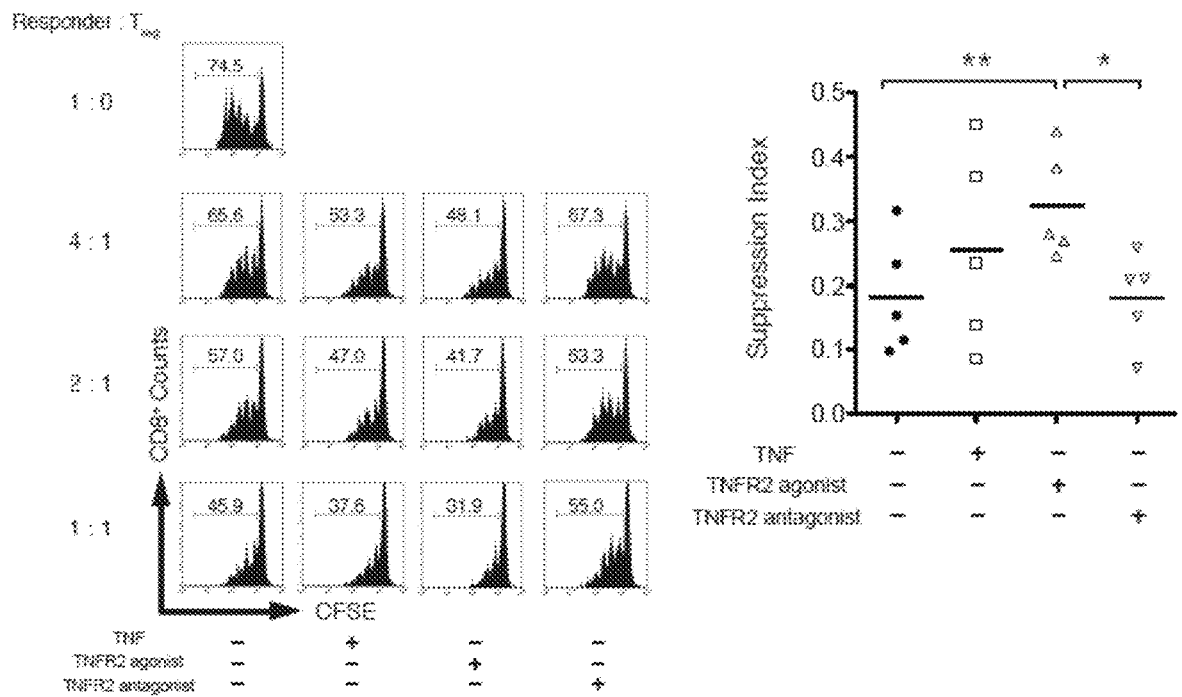
FIG. 5A is a set of graphs showing that in a representative case, TNFR2 agonist-treated Tregs exerted stronger and dose-dependent suppression of CD8+ cell numbers, compared to other groups, at all dilutions or suppression ratios (left panel, third column). Using a suppression index of 2:1 (CD8+ Responders to Tregs), TNFR2 agonist suppression of CD8+ cells is greater than no treatment and TNFR2 antagonist treatment (right panel). Data in FIG. 5A (right panel) are samples from 5 subjects and data in FIG. 5B (lower panel) are from 8 subjects.
Figure 13A:
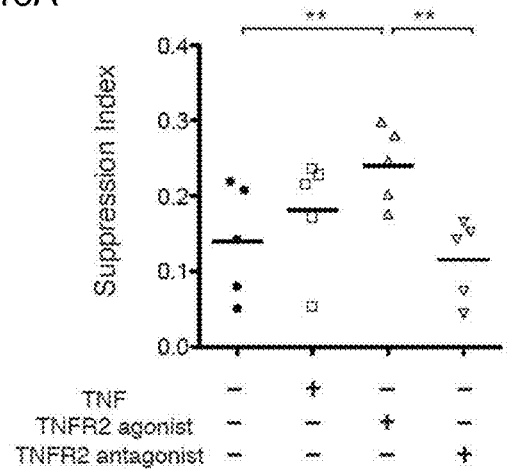
FIG. 13A is a graph showing that the suppression capacity of expanded CD4+CD25+ cells was determined by CFSE dilution of CD8+ T responder cells. Flow cytometric figures of a typical result and summary of suppression index calculated based upon Responder:Treg of 2:1 from four independent experiments is also shown in FIG. 13A.

One key function of Tregs, especially in autoimmunity, is to suppress the function of autoreactive cytotoxic CD8+ T cells. I assessed this capacity by mixing Tregs from each treatment group with CFSE-stained autologous PBMC, after having stimulated them with anti-CD3mAb and IL-2 for 4 days. Autologous CD8+ T cells, the responder cells, were tested for suppression by observing the ratios of responders to Tregs. Ratios of dilution enable study of dose-dependence. All groups of Tregs displayed suppressive function on CD8+ T cells, but the degree varied by treatment group (FIG. 5A, left panel). TNFR2 agonist-treated Tregs, for example, showed the strongest suppressive capacity at 1:1 ratio (by leaving the fewest number of CD8+ cells) and then became progressively weaker at higher ratios. However, the antagonist-treated cells displayed weaker suppressive capacity that was essentially no different from that of no treatment. With a suppression index of 2:1, the TNFR2 agonist-treated group showed greater suppression than did the antagonist and no treatment groups (FIG. 5A, right panel). Similar results were observed with Tregs treated without rapamycin (FIG. 13A). The results are consistent with known phenotypes and expansion capacity of functional Tregs.

Example 5

TNFR2 Agonist-Treated Tregs and Cytokine Production

Figure 5B:
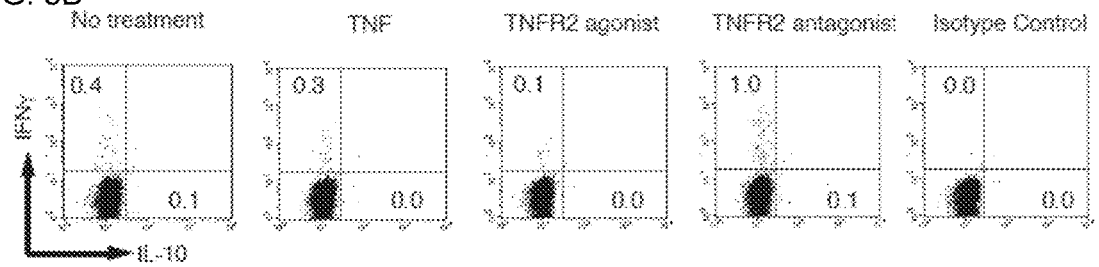
FIG. 5B is a set of graphs showing that TNFR2 agonist-treated Tregs produce a lower percentage of IFNγ+ cells.
Figure 5B:
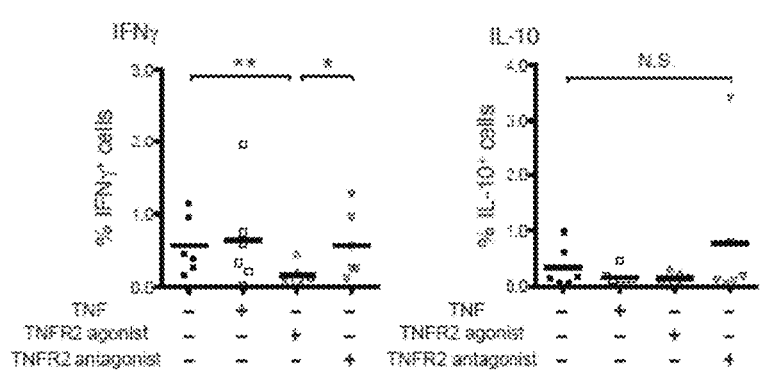
Figure 5C:
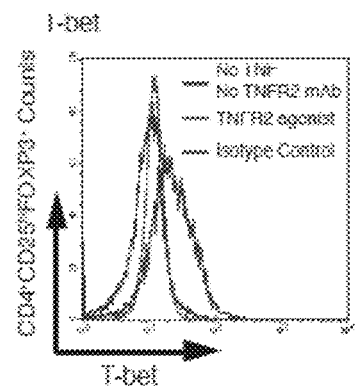
FIG. 5C is a graph showing lower numbers of T-bet+ cells after stimulation with PMA and ionomycin for 24 hours.
Figure 6:
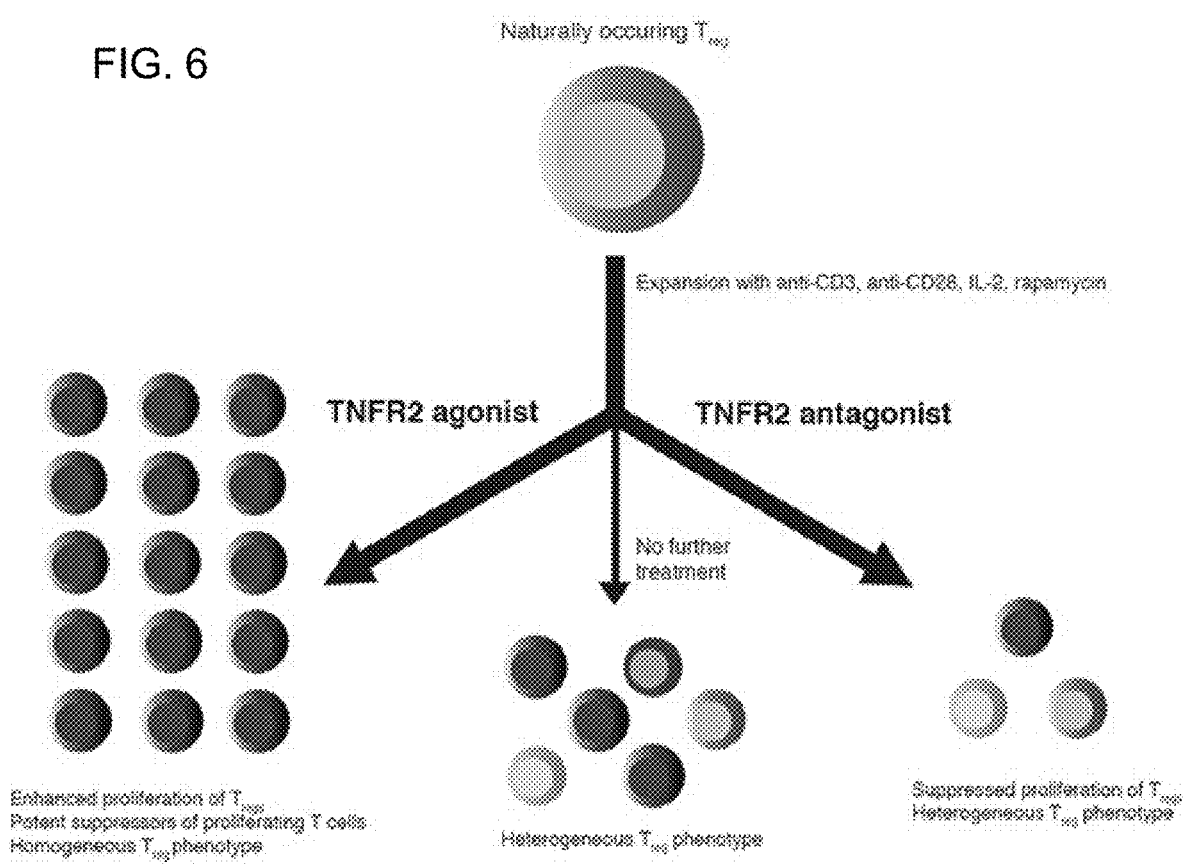
FIG. 6 is a schematic showing the summary of findings with TNFR2 agonist versus antagonist. After purification and expansion, the TNFR2 agonist is better than TNFR2 antagonist at proliferating and yielding more phenotypically homogeneous Tregs (CD4+ CD25$^{hi}$ FOXP3+ CTLA4+ TNFR2+ CD45RO+ CD62L+ CD127−, HLA-DR$^{hi}$ CCR5− CCR7− CXCR3− ICOS−), with higher suppression capacity for CD8+ cells, and lower cytokine-producing capability.
Figure 13B:
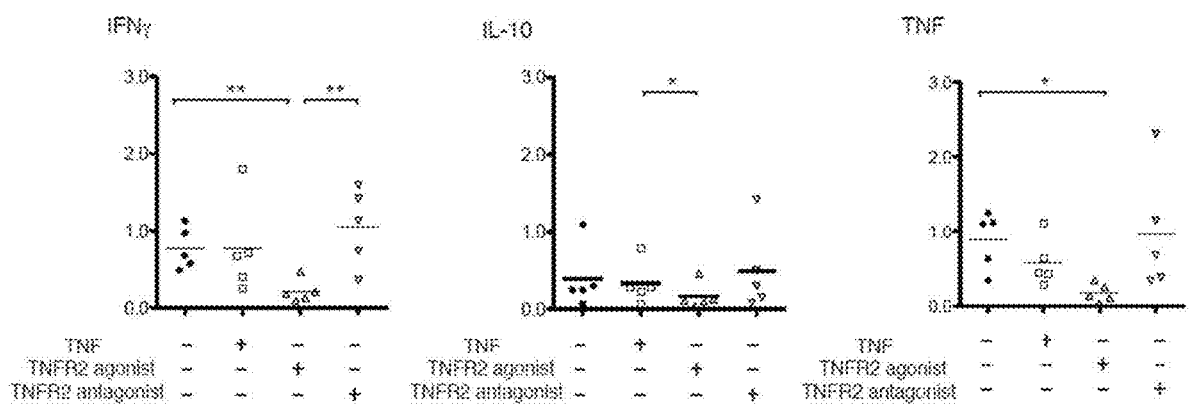
FIG. 13B is a set of graphs showing that CD4+CD25+ cells expanded with TNFR2 agonist exhibited significant enhanced suppression capacity (N=5). Those cells showed lowest cytokine producing capacity. (IFN, IL-10 and TNF after stimulation with PMA and ionomycin for 24 hours (*; $p<0.05$, **; $p<0.01$, by paired t test).

I found that all treatment groups had relatively limited ability to produce intracellular IFNγ and IL-10 after PMA and ionomycin stimulation. But TNFR2 agonist and the TNF only-treated Tregs produced the lowest percentages of IFNγ+cells (FIG. 5B, lowest left panel). The antagonist-treated Tregs showed significantly higher IFNγ production than the agonist (FIG. 5b, lower left panel). In similar experiments without rapamycin, the TNFR2 agonist-treated group not only produced lower IFNγ, but also lower IL-10 and TNF production relative to TNF or no treatment, respectively (FIG. 13B). Agonist-treated Tregs also showed the fewest number of TH1 Transcription Factor (T-bet)+Tregs (FIG. 5C), which is consistent with lower IFNγ production (FIG. 5C). One of the reasons for these Tregs showing high suppression capacity over CD8+ T cells may be due to Tregs lacking the ability to produce IFNγ.

Other Embodiments

The disclosures of U.S. Provisional Patent Application No. 61/762,136, filed on Feb. 7, 2013, and U.S. Provisional Patent Application No. 61/763,217, filed on Feb. 11, 2013, are hereby incorporated by reference in their entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety.

Other embodiments are in the claims.

---

The invention claimed is:

1. A method of treating a proliferative disorder or an infectious disease in a subject comprising administering to said subject an isolated human, humanized, or chimeric antibody, or antigen-binding fragment thereof, that selectively binds to an epitope of TNFR2 that is bound by antibody clone MAB726 or by antibody clone M1.

2. The method of claim 1, wherein said proliferative disorder is a cancer selected from the group consisting of Acute Lymphoblastic Leukemia, Acute Lymphoblastic Leukemia, Acute Myeloid Leukemia, Adrenocortical Carcinoma, AIDS-Related Lymphoma, AIDS-Related Malignancies, Anal Cancer, Astrocytoma, Bile Duct Cancer, Bladder Cancer, Bone Cancer, Osteosarcoma/Malignant Fibrous Histiocytoma, Brain Stem Glioma, Visual Pathway and Hypothalamic Glioma, Breast Cancer, Bronchial Adenomas/Carcinoids, Chronic Lymphocytic Leukemia, Chronic Myelogenous Leukemia, Chronic Myeloproliferative Disorders, Clear Cell Sarcoma of Tendon Sheaths, Colon Cancer, Colorectal Cancer, Cutaneous T-Cell Lymphoma, Endometrial Cancer, Epithelial Cancer, Esophageal Cancer, Ewing's Family of Tumors, Extracranial Germ Cell Tumor, Extragonadal Germ Cell Tumor, Extrahepatic Bile Duct Cancer, Eye Cancer, Intraocular Melanoma, Retinoblastoma, Gallbladder Cancer, Gastric (Stomach) Cancer, Hairy Cell Leukemia, Head and Neck Cancer, Hepatocellular (Liver) Cancer, Hodgkin's Lymphoma, Hypopharyngeal Cancer, Kaposi's Sarcoma, Kidney Cancer, Laryngeal Cancer, Pituitary Cancer, Plasma Cell Neoplasm/Multiple Myeloma, Pleuropulmonary Blastoma, Skin Cancer, Small Cell Lung Cancer, Small Intestine Cancer, Soft Tissue Sarcoma, Squamous Neck Cancer, Testicular Cancer, Thyroid Cancer, Urethral Cancer, Uterine Sarcoma, and Vaginal Cancer, or wherein said proliferative disorder is a solid tumor of the brain, lung, breast, lymphoid, gastrointestinal tract, genitourinary tract, pharynx, prostate, or ovary.

3. The method of claim 1, wherein said infectious disease is selected from the group consisting of a bacterial infection, a viral infection, a fungal infection, and a parasitic infection.

4. The method of claim 1, wherein said epitope comprises amino acids 135-147 of SEQ ID NO: 1.

5. The method of claim 1, wherein said proliferative disorder is a cancer selected from the group consisting of breast cancer, T-cell lymphoma, endometrial cancer, esophageal cancer, gastric cancer, hepatocellular cancer, Hodgkin's lymphoma, kidney cancer, multiple myeloma, skin cancer, lung cancer, and ovarian cancer.

6. The method of claim 1, wherein said subject is a mammal.

7. The method of claim 6, wherein said mammal is a human.

8. The method of claim 1, wherein said method comprises treating the proliferative disorder.

9. The method of claim 1, wherein said proliferative disorder is a cancer.

10. The method of claim 1, wherein said method comprises treating the infectious disease.

* * * * *